(12) United States Patent
Lionberger et al.

(10) Patent No.: US 11,789,016 B2
(45) Date of Patent: *Oct. 17, 2023

(54) METHODS, SYSTEMS AND KITS FOR IN-PEN ASSAYS

(71) Applicant: Berkeley Lights, Inc., Emeryville, CA (US)

(72) Inventors: Troy A. Lionberger, Berkeley, CA (US); Phillip J. M. Elms, Oakland, CA (US); Anupam Singhal, Berkeley, CA (US); Randall D. Lowe, Jr., Emeryville, CA (US); Volker L. S. Kurz, Oakland, CA (US); Paul M. Lebel, Redwood City, CA (US)

(73) Assignee: PHENOMEX INC., Emeryville, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 16/849,811

(22) Filed: Apr. 15, 2020

(65) Prior Publication Data
US 2020/0408751 A1    Dec. 31, 2020

Related U.S. Application Data

(63) Continuation of application No. PCT/US2018/055918, filed on Oct. 15, 2018.
(Continued)

(51) Int. Cl.
*B01L 3/00* (2006.01)
*G01N 33/543* (2006.01)
*G01N 33/68* (2006.01)

(52) U.S. Cl.
CPC .. *G01N 33/54366* (2013.01); *B01L 3/502761* (2013.01); *G01N 33/6854* (2013.01);
(Continued)

(58) Field of Classification Search
None
See application file for complete search history.

(56) References Cited

U.S. PATENT DOCUMENTS

| | | | |
|---|---|---|---|
| 6,294,063 B1 | 9/2001 | Becker et al. | |
| 6,462,254 B1 | 10/2002 | Vernachio et al. | |

(Continued)

FOREIGN PATENT DOCUMENTS

| | | |
|---|---|---|
| CN | 1668913 | 9/2005 |
| CN | 101275114 | 10/2008 |

(Continued)

OTHER PUBLICATIONS

International Search Report and Written Opinion dated Mar. 22, 2019 in PCT/US2018/055918.

(Continued)

*Primary Examiner* — Rebecca M Giere
(74) *Attorney, Agent, or Firm* — NORTON ROSE FULBRIGHT US LLP

(57) ABSTRACT

Methods, systems and kits are described herein for detecting the results of an assay. In particular, the methods, systems and devices of the present disclosure rely on a difference between the diffusion rates of a reporter molecule and an analyte of interest in order to quantify an amount of analyte in a microfluidic device. The analyte may be a secreted product of a biological micro-object.

23 Claims, 44 Drawing Sheets

Specification includes a Sequence Listing.

Related U.S. Application Data

(60) Provisional application No. 62/572,525, filed on Oct. 15, 2017.

(52) U.S. Cl.
CPC .......... B01L 2200/0668 (2013.01); B01L 2300/0654 (2013.01); B01L 2300/0864 (2013.01); B01L 2300/165 (2013.01); B01L 2300/1822 (2013.01); B01L 2400/0424 (2013.01); B01L 2400/0457 (2013.01); B01L 2400/0472 (2013.01); B01L 2400/086 (2013.01)

(56) References Cited

U.S. PATENT DOCUMENTS

| | | |
|---|---|---|
| 6,942,776 B2 | 9/2005 | Medoro |
| 7,090,759 B1 | 8/2006 | Seul |
| 2003/0008364 A1 | 1/2003 | Wang et al. |
| 2003/0044870 A1 | 6/2003 | Sehr et al. |
| 2003/0199671 A1 | 10/2003 | Rondon et al. |
| 2004/0072278 A1 | 4/2004 | Chou et al. |
| 2004/0191789 A1 | 9/2004 | Manaresi et al. |
| 2004/0197905 A1 | 10/2004 | Hafeman |
| 2005/0112548 A1 | 5/2005 | Segawa et al. |
| 2005/0129581 A1 | 6/2005 | McBride et al. |
| 2005/0175981 A1 | 8/2005 | Voldman et al. |
| 2005/0266571 A1 | 12/2005 | Stout et al. |
| 2006/0091015 A1 | 5/2006 | Lau |
| 2006/0154361 A1 | 7/2006 | Wikswo et al. |
| 2006/0263612 A1 | 11/2006 | Chen et al. |
| 2007/0095669 A1 | 5/2007 | Lau et al. |
| 2007/0183934 A1 | 8/2007 | Diercks et al. |
| 2007/0225231 A1 | 9/2007 | Bodie et al. |
| 2007/0242105 A1 | 10/2007 | Srinivasan et al. |
| 2008/0013092 A1 | 1/2008 | Maltezos et al. |
| 2008/0038755 A1* | 2/2008 | Kauvar .......... G01N 33/6842 435/7.1 |
| 2008/0223721 A1 | 9/2008 | Cohen et al. |
| 2008/0302732 A1 | 12/2008 | Soh et al. |
| 2009/0023608 A1 | 1/2009 | Hung et al. |
| 2009/0170186 A1 | 7/2009 | Wu et al. |
| 2009/0197326 A1 | 8/2009 | Gamal et al. |
| 2010/0003666 A1 | 1/2010 | Lee et al. |
| 2010/0009335 A1 | 1/2010 | Joseph et al. |
| 2010/0101960 A1 | 4/2010 | Ohta et al. |
| 2010/0273681 A1 | 10/2010 | Cerrina et al. |
| 2011/0053151 A1 | 3/2011 | Hansen et al. |
| 2011/0117634 A1 | 5/2011 | Halamish et al. |
| 2011/0143964 A1 | 6/2011 | Zhou et al. |
| 2011/0262906 A1 | 10/2011 | Dimov et al. |
| 2012/0009671 A1 | 1/2012 | Hansen et al. |
| 2012/0015347 A1 | 1/2012 | Singhal et al. |
| 2012/0015382 A1 | 1/2012 | Weitz et al. |
| 2012/0091059 A1 | 4/2012 | Beer et al. |
| 2012/0118740 A1 | 5/2012 | Garcia et al. |
| 2012/0149128 A1 | 6/2012 | Manneh |
| 2012/0156675 A1 | 6/2012 | Lueerssen et al. |
| 2012/0258474 A1 | 10/2012 | Tatnell et al. |
| 2012/0325665 A1 | 12/2012 | Chiou et al. |
| 2013/0115606 A1 | 5/2013 | Hansen et al. |
| 2013/0118905 A1 | 5/2013 | Morimoto et al. |
| 2013/0130232 A1 | 5/2013 | Weibel et al. |
| 2013/0146459 A1 | 6/2013 | Bazant et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0261021 A1 | 10/2013 | Bocchi et al. |
| 2014/0116881 A1 | 5/2014 | Chapman et al. |
| 2014/0124370 A1 | 5/2014 | Short et al. |
| 2015/0018226 A1 | 1/2015 | Hansen et al. |
| 2015/0037890 A1 | 2/2015 | Mershin et al. |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2015/0352547 A1 | 12/2015 | Breinlinger et al. |
| 2016/0171686 A1 | 6/2016 | Du et al. |
| 2016/0184821 A1 | 6/2016 | Hobbs et al. |
| 2016/0199837 A1 | 7/2016 | Breinlinger et al. |
| 2016/0252495 A1 | 9/2016 | Ricicova et al. |
| 2016/0312165 A1 | 10/2016 | Lowe, Jr. et al. |
| 2016/0312298 A1 | 10/2016 | Ting et al. |
| 2017/0184583 A1 | 6/2017 | Beaumont et al. |
| 2017/0216842 A1 | 8/2017 | Khattak et al. |
| 2018/0298318 A1 | 10/2018 | Kurz et al. |
| 2019/0240665 A1 | 8/2019 | Lionberger et al. |
| 2019/0275516 A1 | 9/2019 | Lowe, Jr. et al. |

FOREIGN PATENT DOCUMENTS

| | | |
|---|---|---|
| CN | 102460181 | 5/2012 |
| CN | 104838273 | 8/2015 |
| EP | 0643306 A2 | 9/1995 |
| JP | H06288895 | 10/1994 |
| JP | 2007537729 | 12/2007 |
| JP | 2011000079 | 1/2011 |
| JP | 2011000079 A | 1/2011 |
| JP | 2012034641 | 2/2012 |
| JP | 2012034641 A | 2/2012 |
| JP | 2015532443 | 11/2015 |
| KR | 20100008222 | 1/2010 |
| WO | WO 2002/088702 | 11/2002 |
| WO | WO 2003/095995 | 11/2003 |
| WO | WO 2004/089810 | 10/2004 |
| WO | WO 2005/100541 | 10/2005 |
| WO | WO 2007/008609 | 1/2007 |
| WO | WO 2007/024701 | 3/2007 |
| WO | WO 2008/119066 | 10/2008 |
| WO | WO 2009/130694 | 10/2009 |
| WO | WO 2010/040851 | 4/2010 |
| WO | WO 2010/115167 | 10/2010 |
| WO | WO 2010/132741 | 11/2010 |
| WO | WO 2010/147078 | 12/2010 |
| WO | WO 2010/147942 | 12/2010 |
| WO | WO 2011/149032 | 12/2011 |
| WO | WO 2011/160430 | 12/2011 |
| WO | WO 2012/037030 | 3/2012 |
| WO | 2012072823 A1 | 6/2012 |
| WO | WO 2012/072823 | 6/2012 |
| WO | 2012162779 A1 | 12/2012 |
| WO | WO 2012/162779 | 12/2012 |
| WO | WO 2013/019491 | 2/2013 |
| WO | 2013130714 A1 | 9/2013 |
| WO | WO 2013/130714 | 9/2013 |
| WO | WO 2014/036915 | 3/2014 |
| WO | WO 2014064438 | 5/2014 |
| WO | 2014153651 A1 | 11/2014 |
| WO | WO 2014/153651 | 11/2014 |
| WO | 2015188171 A1 | 12/2015 |
| WO | WO 2015/188171 | 12/2015 |
| WO | 2017091601 A1 | 6/2017 |
| WO | 2017181135 A2 | 10/2017 |
| WO | 2017181135 A3 | 1/2019 |

OTHER PUBLICATIONS

Alonzo, Luis F., et al. "Microfluidic device to control interstitial flow-mediated homotypic and heterotypic cellular communication" Lab on a Chip, vol. 15, No. 17, pp. 3521-3529, Sep. 7, 2015.

Delano, Warren L. et al. "Convergent solutions to binding at a protein-protein interface" Science vol. 18, No. 5456, pp. 1279-1283, Feb. 18, 2000.

Lubbeck, Jennifer L., et al. "Microfluidic flow cytometer for quantifying photobleaching of fluorescent proteins in cells" Analytical chemistry, vol. 84, No. 9, pp. 3929-3937, May 1, 2012.

Moledina, Faisal et al. "Predictive microfluidic control of regulatory ligand trajectories in individual pluripotent cells" Proceedings of the National Academy of Sciences, vol. 109, No. 9, pp. 3264-3269, Feb. 28, 2012.

Son, Kyung Jin et al. "Microfluidic compartments with sensing microbeads for dynamic monitoring of cytokine and exosome

(56) References Cited

OTHER PUBLICATIONS release from single cells" Analyst, vol. 141, No. 2, pp. 679-688, 2016.
Chiou et al., "Massively parallel manipulation of single cells and microparticles using optical images," Nature, vol. 436 (Jul. 21, 2005), pp. 370-372.
Chiou, Pei-Yu, Massively Parallel Optical Manipulation of Cells, Micro- and Nano-Particles on Optoelectronic devices, Dissertation, University of California at Berkeley, 2005 (147 pages).
Chung et al., Imaging Single-Cell Signaling Dynamics with a Deterministic High-Density Single-Cell Trap Array, Anal. Chem. 83(18):7044-7052 (2011).
Hsu, HY et al., "Sorting of Differentiated Neurons Using Phototransistor-Based Optoelectronic Tweezers for Cell Replacement Therapy of Neurodegenerative Diseases", Transducers 2009, Denver, CO USA Jun. 2009, download dated Nov. 23, 2009 from IEEE Xplore, 4 pages.
Hung et al., Continuous Perfusion Microfluidic Cell Culture Array for High-Throughput Cell-Based Assays, Biotech and Bioengineering 89(1): 1-8 (2004). Dec. 3, 2004.
Iliescu et al., Continuous Field-Flow Separation of Particle Populations in a Dielectrophoretic Chip with Three Dimensional Electrodes, Applied Physics Letters 90:234104 (2007).
Lynn et al. Mapping Spatiotemporal Molecular Distributions Using a Microfluidic Array, Nov. 2011, Analytical Chemistry, vol. 84, pp. 1360-1366. (Year: 2011).
Nevill et al., Integrated microfluidic cell culture and lysis on a chip, Lab on a Chip 7:1689-95 (2007).
Somaweera H et al., Generation of a Chemical Gradient Across an Array of 256 Cell Cultures in a Single Chip. Analyst, Oct. 7, 2013, vol. 138, No. 19, pp. 5566-5571.
Torres et al., "Nanowell-Based Immunoassays for Measuring Single-Cell Secretion: Characterization of Transport and Surface Binding" Oct. 2014, Analytical Chemistry, vol. 86, p. 11562-11569. (Year: 2014).
Valley et al., Optoelectronic Tweezers as a Tool for Parallel Single-Cell Manipulation and Simulation, IEEE Transactions on Biomedical Circuits and Systems, vol. 3, No. 6 (Dec. 2009), pp. 424-431.
Xu, Guoling et al,. Recent Trends in Dielectrophoresis, Informacije MIDEM, 2010, vol. 40, Issue No. 4, pp. 253-262.
Yi et al., "Microfluidics technology for manipulation and analysis of biological cells," Analytica Chimica Acta 560 (2006), pp. 1-23.
Fritze et al., "Epitope Tagging: General Method for Tracking Recombinant Proteins," Methods in Enzymology, 2000, pp. 3-16,vol. 327, Academic Press, 14 pages.
DiCarlo et al., "Dynamic Single Cell Analysis for Quantitative Biology," Analytical Chemistry (Dec. 1, 2006), pp. 7918-7925.
Li, Y. et al. "AxonQuant: A Microfluidic Chamber Culture-Coupled Algorithm that Allows High-Throughput Quantification of Axonal Damage;" Neurosignals, Feb. 28, 2014, vol. 22, pp. 14-29.
Wu, L et al., "Fluctuations of DNA mobility in nanofluidic entropic traps;" Biomicrofluidics, Jul. 8, 2014, vol. 8, pp. 1-14.
Office Action issued in corresponding Japanese Application No. 2021191279, dated Jan. 5, 2023.
ISA/US—Notification and Corrected International Search Report and Written Opinion for related International Application No. PCT/US2017/027795 dated Dec. 18, 2018, 15 pages.
ISA/US—Notification and International Search Report for related International Application No. PCT/US2017/027795 dated Sep. 2017, 7 pages.
ISA/US—Notification and International Preliminary report and Patentability for related International Application No. PCT/US2017/027795 dated Dec. 27, 2018, 1 pages.
Office Action dated Mar. 13, 2020 in Singapore Patent Application No. 11201808914U (BI001553-SG) (12 pages).
WO 2010147078, University of Toyko, Machine Translation , Dec. 23, 2010, 12 pages.

\* cited by examiner

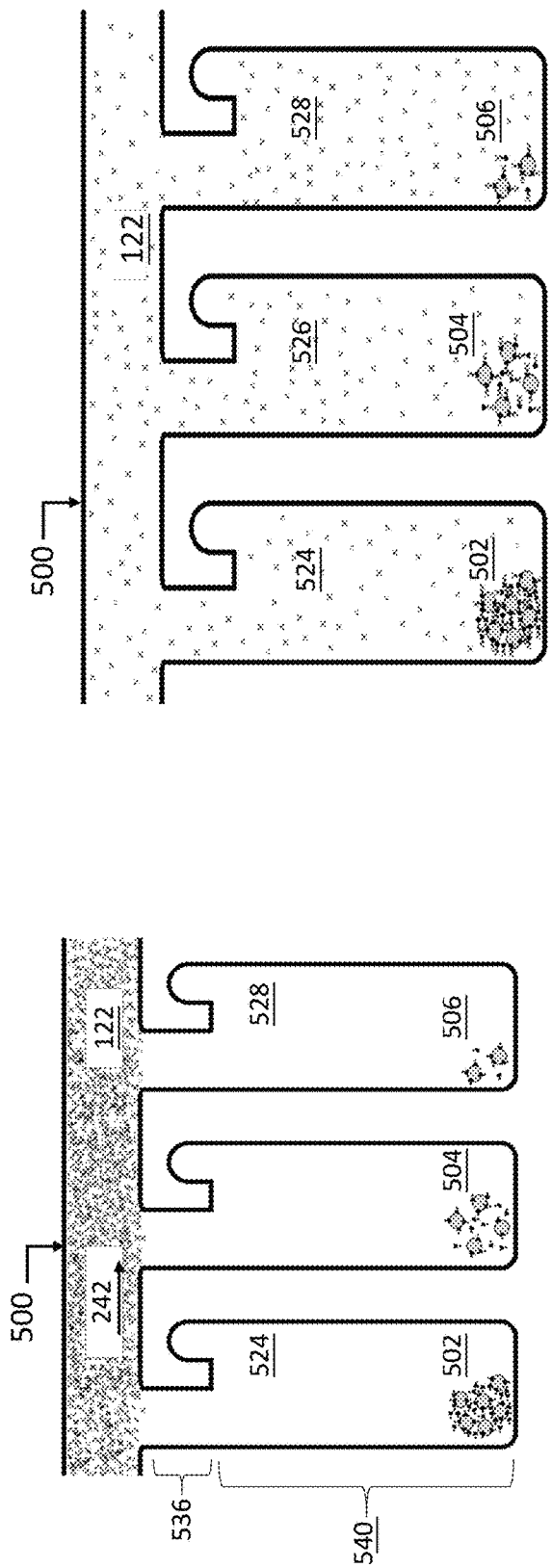
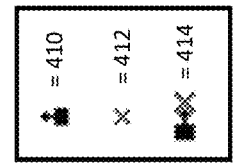
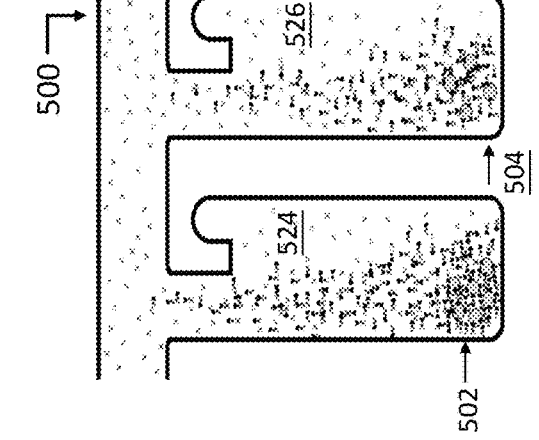
FIG. 5A
FIG. 5B
FIG. 5C

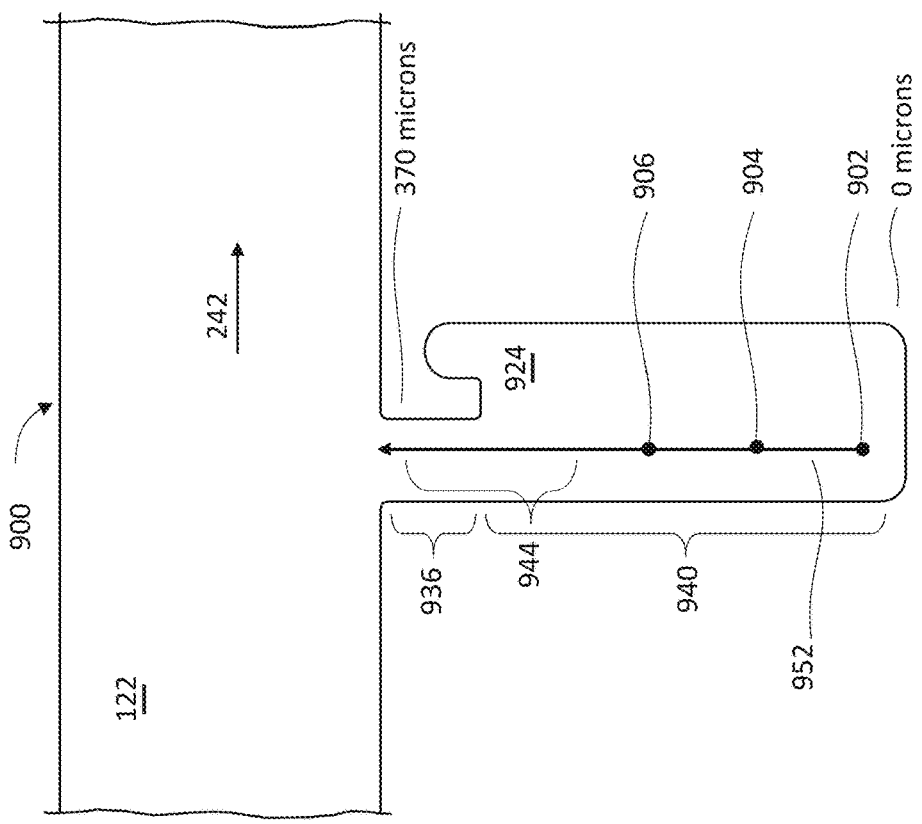
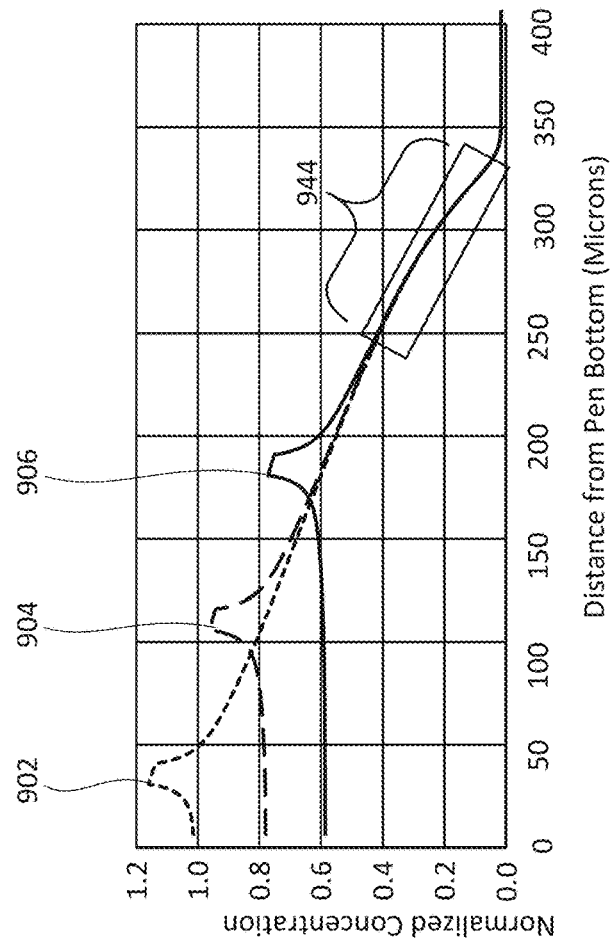
FIG. 9B
FIG. 9A

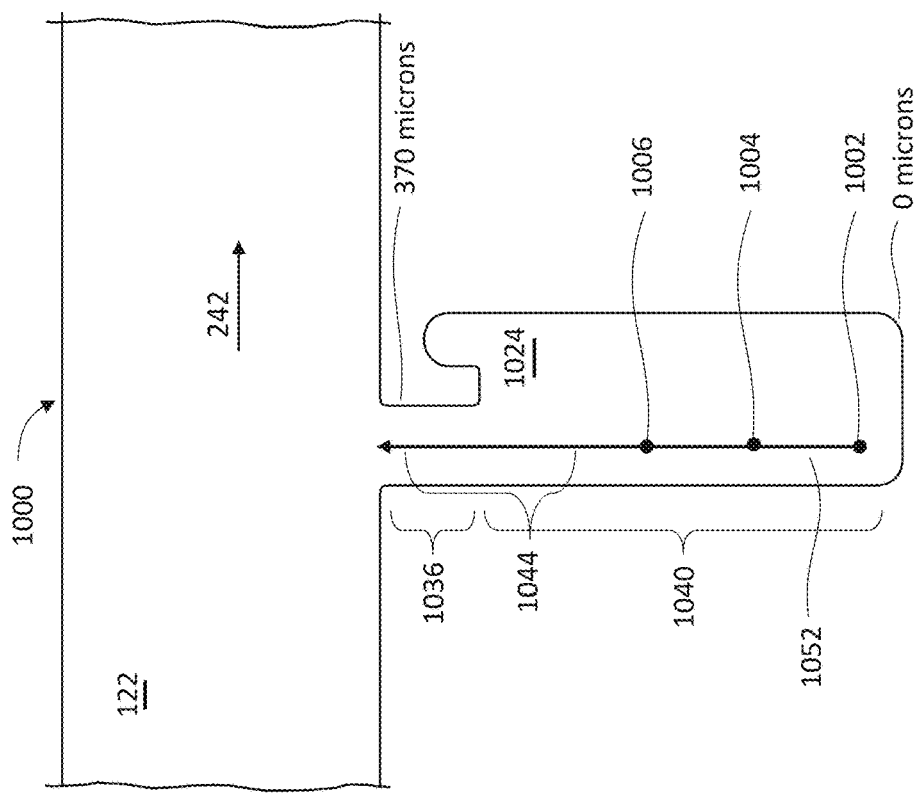
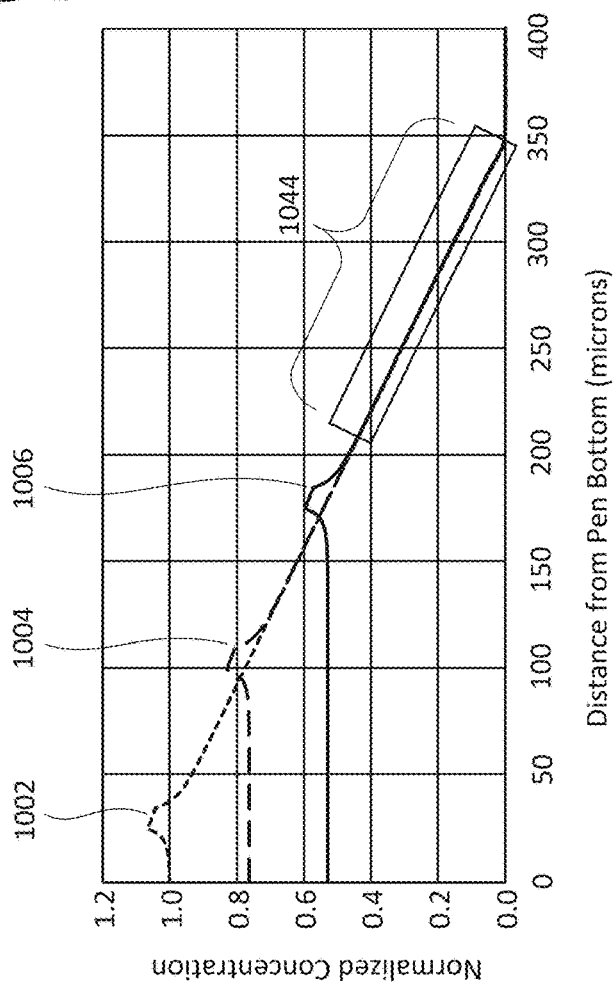
FIG. 10B
FIG. 10A

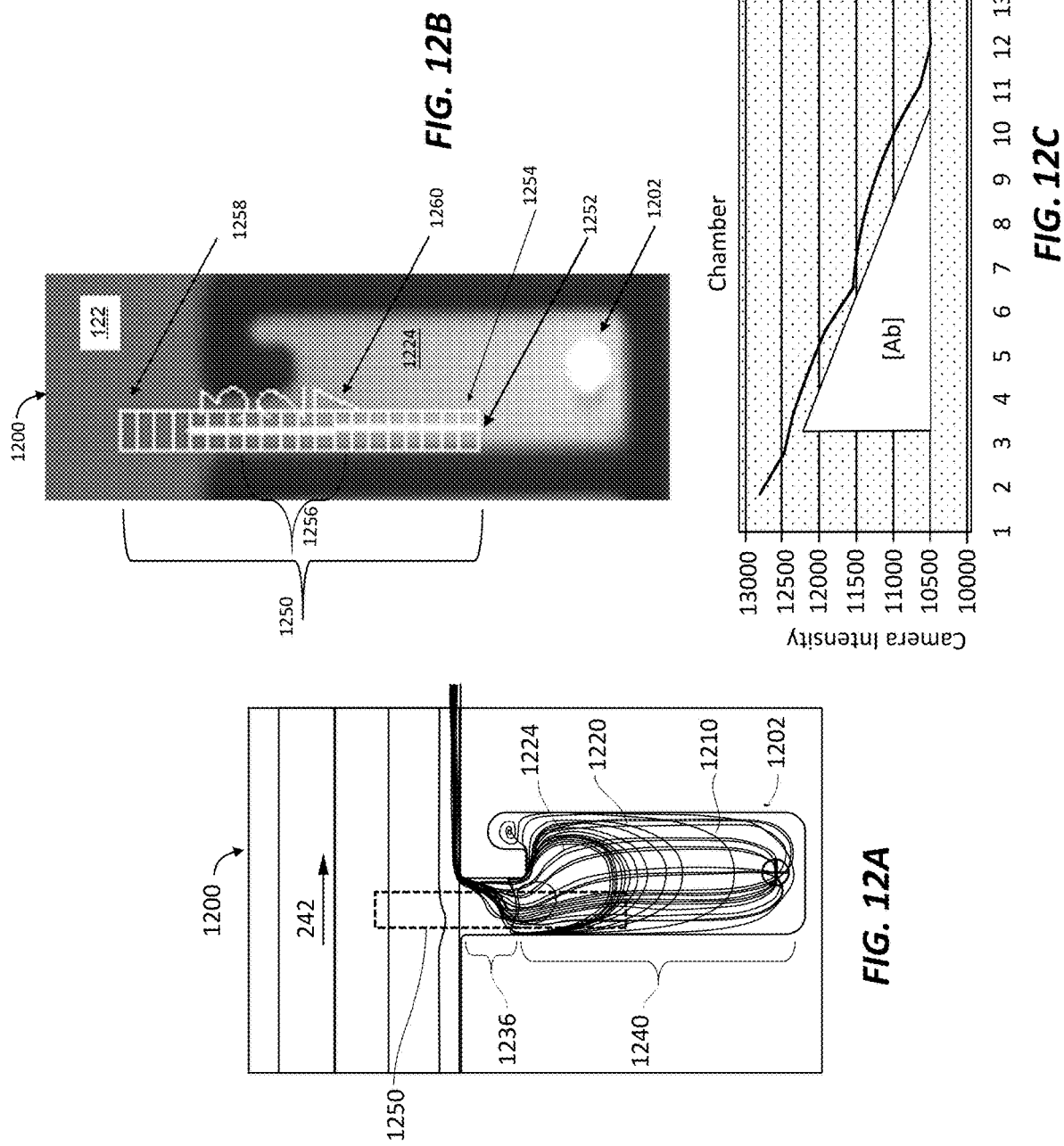

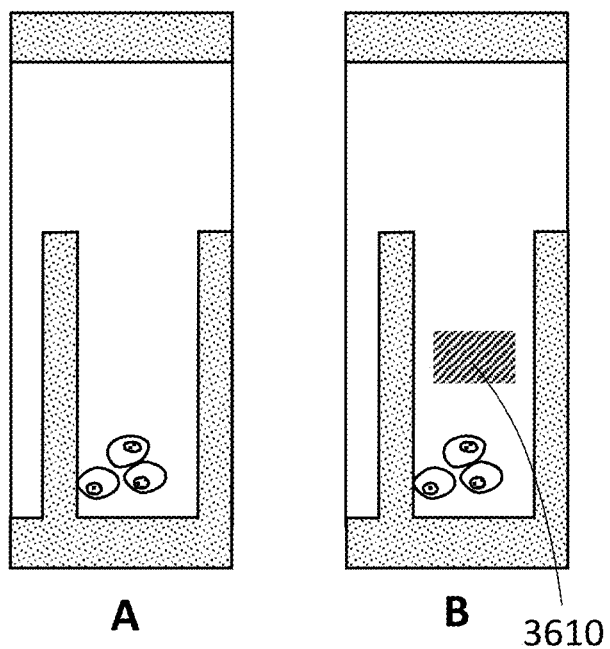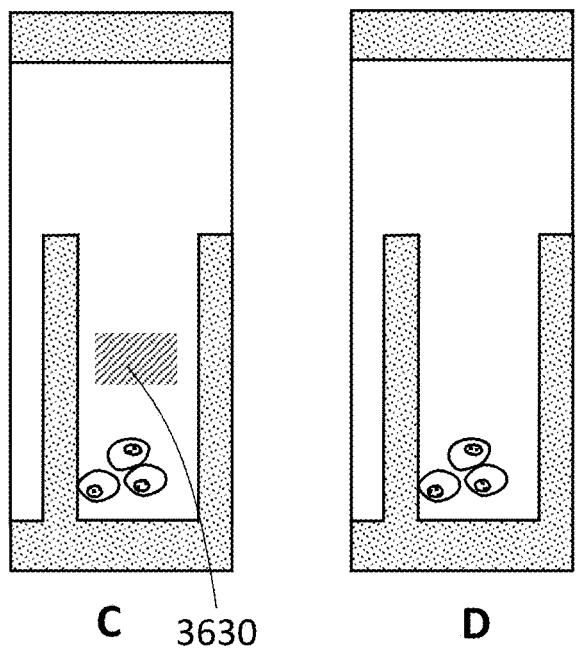
FIG. 32

SEQUENCE LISTING

<160> NUMBER OF SEQ ID NOS: 13

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      IgG binding peptide
<220> FEATURE:
<221> NAME/KEY: MOD_RES
<222> LOCATION: (1)..(4)
<223> OTHER INFORMATION: Any amino acid or absent

```
<220> FEATURE:
<221> NAME/KEY: MOD_RES
<222> LOCATION: (5)..(5)
<223> OTHER INFORMATION: Cys or Ser
<220> FEATURE:
<221> NAME/KEY: MOD_RES
<222> LOCATION: (6)..(11)
<223> OTHER INFORMATION: Any amino acid
<220> FEATURE:
<221> NAME/KEY: MOD_RES
<222> LOCATION: (16)..(20)
<223> OTHER INFORMATION: Any amino acid or absent

<400> SEQUENCE: 1

Xaa Xaa Xaa Xaa Xaa Xaa Xaa Xaa Xaa Xaa Xaa Leu Val Trp Cys Xaa
1               5                   10                  15

Xaa Xaa Xaa Xaa
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      IgG binding peptide
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (5)..(5)
<223> OTHER INFORMATION: Cys or Ser
<220> FEATURE:
<221> NAME/KEY: MOD_RES
<222> LOCATION: (6)..(9)
<223> OTHER INFORMATION: Any amino acid
<220> FEATURE:
<221> NAME/KEY: MOD_RES
<222> LOCATION: (16)..(20)
<223> OTHER INFORMATION: Any amino acid or absent

<400> SEQUENCE: 2

Xaa Xaa Xaa Xaa Xaa Xaa Xaa Xaa Xaa Gly Glu Leu Val Trp Cys Xaa
1               5                   10                  15

Xaa Xaa Xaa Xaa
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      IgG binding peptide
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (5)..(5)
<223> OTHER INFORMATION: Cys or Ser
<220> FEATURE:
<221> NAME/KEY: MOD_RES
<222> LOCATION: (6)..(6)
<223> OTHER INFORMATION: Ala, Ser or Thr
<220> FEATURE:
<221> NAME/KEY: MOD_RES
<222> LOCATION: (7)..(7)
<223> OTHER INFORMATION: Trp or Tyr
<220> FEATURE:
```

```
<221> NAME/KEY: MOD_RES
<222> LOCATION: (8)..(8)
<223> OTHER INFORMATION: His or Trp
<220> FEATURE:
<221> NAME/KEY: MOD_RES
<222> LOCATION: (9)..(9)
<223> OTHER INFORMATION: Leu or Met
<220> FEATURE:
<221> NAME/KEY: MOD_RES
<222> LOCATION: (16)..(20)
<223> OTHER INFORMATION: Any amino acid or absent

<400> SEQUENCE: 3

Xaa Xaa Xaa Xaa Xaa Xaa Xaa Xaa Xaa Gly Glu Leu Val Trp Cys Xaa
1               5                   10                  15

Xaa Xaa Xaa Xaa
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      IgG binding peptide
<220> FEATURE:
<221> NAME/KEY: MOD_RES
<222> LOCATION: (1)..(3)
<223> OTHER INFORMATION: Any amino acid or absent
<220> FEATURE:
<221> NAME/KEY: MOD_RES
<222> LOCATION: (4)..(4)
<223> OTHER INFORMATION: Ser, Arg or Asp
<220> FEATURE:
<221> NAME/KEY: MOD_RES
<222> LOCATION: (5)..(5)
<223> OTHER INFORMATION: Cys or Ser
<220> FEATURE:
<221> NAME/KEY: MOD_RES
<222> LOCATION: (6)..(6)
<223> OTHER INFORMATION: Ala, Ser or Thr
<220> FEATURE:
<221> NAME/KEY: MOD_RES
<222> LOCATION: (7)..(7)
<223> OTHER INFORMATION: Trp or Tyr
<220> FEATURE:
<221> NAME/KEY: MOD_RES
<222> LOCATION: (8)..(8)
<223> OTHER INFORMATION: His or Trp
<220> FEATURE:
<221> NAME/KEY: MOD_RES
<222> LOCATION: (9)..(9)
<223> OTHER INFORMATION: Leu or Met
<220> FEATURE:
<221> NAME/KEY: MOD_RES
<222> LOCATION: (16)..(16)
<223> OTHER INFORMATION: Glu, Ser, Thr or Val
<220> FEATURE:
<221> NAME/KEY: MOD_RES
<222> LOCATION: (17)..(20)
<223> OTHER INFORMATION: Any amino acid or absent

<400> SEQUENCE: 4

Xaa Xaa Xaa Xaa Xaa Xaa Xaa Xaa Xaa Gly Glu Leu Val Trp Cys Xaa
1               5                   10                  15

Xaa Xaa Xaa Xaa
            20

<210> SEQ ID NO 5
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      IgG binding peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (2)..(2)
<223> OTHER INFORMATION: Cys or Ser
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (13)..(13)
<223> OTHER INFORMATION: Any amino acid or absent

<400> SEQUENCE: 5

Xaa Xaa Xaa Xaa Xaa Xaa Xaa Xaa Leu Val Trp Cys Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG binding peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (2)..(2)
<223> OTHER INFORMATION: Cys or Ser
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (13)..(13)
<223> OTHER INFORMATION: Any amino acid

<400> SEQUENCE: 6

Xaa Xaa Xaa Xaa Xaa Xaa Gly Glu Leu Val Trp Cys Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG binding peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (2)..(2)
<223> OTHER INFORMATION: Cys or Ser
<220> FEATURE:
<221> NAME/KEY: MOD_RES
<222> LOCATION: (3)..(3)
<223> OTHER INFORMATION: Ala, Ser or Thr
<220> FEATURE:
<221> NAME/KEY: MOD_RES
<222> LOCATION: (4)..(4)
<223> OTHER INFORMATION: Trp or Tyr
<220> FEATURE:
```

```
<221> NAME/KEY: MOD_RES
<222> LOCATION: (5)..(5)
<223> OTHER INFORMATION: His or Trp
<220> FEATURE:
<221> NAME/KEY: MOD_RES
<222> LOCATION: (6)..(6)
<223> OTHER INFORMATION: Leu or Met
<220> FEATURE:
<221> NAME/KEY: MOD_RES
<222> LOCATION: (13)..(13)
<223> OTHER INFORMATION: Any amino acid or absent

<400> SEQUENCE: 7

Xaa Xaa Xaa Xaa Xaa Xaa Gly Glu Leu Val Trp Cys Xaa
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG binding peptide
<220> FEATURE:
<221> NAME/KEY: MOD_RES
<222> LOCATION: (1)..(1)
<223> OTHER INFORMATION: Ser, Arg or Asp
<220> FEATURE:
<221> NAME/KEY: MOD_RES
<222> LOCATION: (2)..(2)
<223> OTHER INFORMATION: Cys or Ser
<220> FEATURE:
<221> NAME/KEY: MOD_RES
<222> LOCATION: (3)..(3)
<223> OTHER INFORMATION: Ala, Ser or Thr
<220> FEATURE:
<221> NAME/KEY: MOD_RES
<222> LOCATION: (4)..(4)
<223> OTHER INFORMATION: Trp or Tyr
<220> FEATURE:
<221> NAME/KEY: MOD_RES
<222> LOCATION: (5)..(5)
<223> OTHER INFORMATION: His or Trp
<220> FEATURE:
<221> NAME/KEY: MOD_RES
<222> LOCATION: (6)..(6)
<223> OTHER INFORMATION: Leu or Met
<220> FEATURE:
<221> NAME/KEY: MOD_RES
<222> LOCATION: (13)..(13)
<223> OTHER INFORMATION: Glu, Ser, Thr or Val

<400> SEQUENCE: 8

Xaa Xaa Xaa Xaa Xaa Xaa Gly Glu Leu Val Trp Cys Xaa
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG binding peptide

<400> SEQUENCE: 9

Asp Ser Ala Trp His Leu Gly Glu Leu Val Trp Cys Thr
1               5                   10

<210> SEQ ID NO 10
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      IgG binding peptide

<400> SEQUENCE: 10

Asp Cys Ala Trp His Leu Gly Glu Leu Val Trp Cys Thr
1               5                   10

<210> SEQ ID NO 11
<211> LENGTH: 23
<212> TYPE: RNA
<213> ORGANISM: Artificial Sequence
<220> FEATURE:
<223> OTHER INFORMATION: Description of Artificial Sequence: Synthetic
      IgG binding aptamer
<220> FEATURE:
<221> NAME/KEY: misc_feature
<222> LOCATION: (6)..(6)
<223> OTHER INFORMATION: 2'-F-RNA nucleotide
<220> FEATURE:
<221> NAME/KEY: misc_feature
<222> LOCATION: (8)..(11)
<223> OTHER INFORMATION: 2'-F-RNA nucleotide
<220> FEATURE:
<221> NAME/KEY: misc_feature
<222> LOCATION: (20)..(23)
<223> OTHER INFORMATION: 2'-F-RNA nucleotide

<400> SEQUENCE: 11
ggaggugcuc cgaaaggaac ucc                                                23

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      Flag epitope

<400> SEQUENCE: 12

Asp Tyr Lys Asp Asp Asp Asp Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5
```

METHODS, SYSTEMS AND KITS FOR IN-PEN ASSAYS

CROSS-REFERENCES TO RELATED APPLICATIONS

The present application claims the benefit of U.S. Provisional Patent Application Ser. No. 62/572,525, titled "METHODS, SYSTEMS AND KITS FOR IN-PEN ASSAYS", filed on Oct. 15, 2017, which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Dec. 7, 2018, is named 104199-0034_BLOO2222-PCT_SL.txt and is 7,093 bytes in size.

FIELD

The embodiments disclosed herein generally relates to methods for detecting the results of an assay within a microfluidic device. In particular, the embodiments are generally directed towards, systems, apparatuses and methods for measuring a quantity of an analyte produced by a micro-object confined in a chamber within a microfluidic assembly.

BACKGROUND

The embodiments disclosed herein are generally directed towards, systems, apparatuses and methods for optically measuring a quantity or quality parameter of a micro-object confined within a defined area. More specifically, there is a need for imaging systems or methods that can accurately determine the quantity of an analyte produced by a micro-object confined in a chamber within a microfluidic assembly.

SUMMARY

In one aspect, a system is provided for determining a quantity of analyte produced by a biological micro-object. The system can comprise an image acquisition unit. The image acquisition unit can comprise a microfluidic device holder capable of securing a microfluidic device, wherein the microfluidic device includes a flow region and a plurality of sequestration pens that are fluidically connected to the flow region. Each of the plurality of sequestration pens can hold one or more biological micro-objects. The image acquisition unit can further comprise an imaging element configured to capture one or more assay images of the plurality of sequestration pens and the flow region of the microfluidic device. The system can further comprise an image processing unit communicatively connected to the image acquisition unit. The image processing unit can comprise an area of interest determination engine configured to receive each captured assay image and define an area of interest for each sequestration pen depicted in the assay image. The area of interest can include an image area corresponding to an area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region. The image processing unit can further comprise a scoring engine configured to analyze at least a portion of the image area within the area of interest of each sequestration pen, to determine scores that are indicative of the quantity of analyte in each sequestration pen.

In another aspect, a method is provided for determining a quantity of analyte produced by a biological micro-object. The method can comprise the step of receiving imaging data of a microfluidic device that includes a flow region and a plurality of sequestration pens that are fluidically connected to the flow region. The imaging data can include an analyte assay image and one or both of a background noise image and a signal reference image. The method can further comprise defining an area of interest for each sequestration pen. The area of interest can include an image area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region. The method can even further comprise determining scores that are indicative of the quantity of analyte in each sequestration pen by analyzing at least a portion of the image area of the area of interest for each sequestration pen.

In another aspect, a non-transitory computer-readable medium is provided in which a program is stored for causing a computer to perform an image processing method for determining a quantity of analyte produced by a biological micro-object. The method can comprise receiving imaging data of a microfluidic device that includes a flow region and a plurality of sequestration pens that are fluidically connected to the flow region. The imaging data can include an analyte assay image and one or both of a background noise image and a signal reference image. The method can further comprise defining an area of interest for each sequestration pen. The area of interest can include an image area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region. The method can even further comprise determining scores that are indicative of the quantity of analyte in each sequestration pen by analyzing at least a portion of the image area of the area of interest for each sequestration pen.

In another aspect, a method of assessing a level of secretion of an analyte by a biological micro-object, or a population of biological micro-objects generated therefrom is provided, the method including: introducing the biological micro-object into a sequestration pen of a microfluidic device, wherein the microfluidic device includes an enclosure having a flow region, where the sequestration pen is fluidically connected to the flow region, and wherein sequestration pen contains a first fluidic medium; allowing the biological micro-object, or the population of biological micro-objects generated therefrom, to secrete the analyte into the first fluidic medium within the sequestration pen; introducing a second fluidic medium into the flow region, wherein the second fluidic medium contains a plurality of reporter molecules, and where each reporter molecule includes: a binding component configured to bind the secreted analyte; and a detectable label; allowing a portion of the plurality of reporter molecules to diffuse into the sequestration pen and bind to the analyte secreted therein, thereby producing a plurality of reporter molecule: secreted analyte (RMSA) complexes; and detecting reporter molecules located within an area of interest within the microfluidic device, wherein the area of interest includes at least a portion of the sequestration pen.

In another aspect, a method of clonal line development is provided, the method including: introducing an individual biological micro-object into each of a plurality of sequestration pens of a microfluidic device, where the microfluidic device further includes an enclosure having a flow region, and where each of the sequestration pens of the plurality is fluidically connected to the flow region and contains a first fluidic medium; allowing each biological micro-object, or a clonal population of biological micro-objects generated therefrom, to secrete an analyte into the first fluidic medium contained in the corresponding sequestration pen; introducing a second fluidic medium into the flow region, where the second fluidic medium includes a plurality of reporter molecules, where each reporter molecule includes a binding component configured to bind the secreted analyte; and a detectable label; allowing a portion of the plurality of reporter molecules to diffuse into each sequestration pen of the plurality and bind to at least a portion of the analyte secreted therein, thereby producing a plurality of reporter molecule:secreted analyte (RMSA) complexes in each of the plurality of sequestration pens; detecting, for each sequestration pen of the plurality, an intensity of a signal emanating from a corresponding area of interest, where the area of interest includes at least a portion of the corresponding sequestration pen, and where at least a portion of the signal emanating from the area of interest emanates from the detectable label of reporter molecules located within the area of interest; determining, for each sequestration pen of the plurality, a score based upon the detected signal intensity emanating from the corresponding area of interest; selecting a set of sequestration pens from the plurality of sequestration pens, where each sequestration pen of the set has a score indicating that the biological micro-object, or clonal population, contained therein is a top analyte producer; exporting from the microfluidic device one or more biological micro-objects contained within each sequestration pen of the set of selected sequestration pens; expanding the exported one or more biological micro-objects from each sequestration pen of the set of selected sequestration pens in corresponding reaction vessels; and determining a level of analyte secreted in each corresponding reaction vessel, thereby determining a level of secretion for each biological micro-object or clonal population.

In yet another aspect, a kit for evaluation of secretion levels of analyte of a biological micro-object or a population of biological micro-objects generated therefrom is provided, including: a microfluidic device including an enclosure having a flow region; and a sequestration pen, where the sequestration pen is fluidically connected to the flow region, and where the flow region and the sequestration pen is configured to contain a fluidic medium; and a reporter molecule comprising a detectable label and a binding component configured to bind the analyte.

Additional methods are provided in the claims attached hereto.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIGS. 5A-5C are graphical illustrations of an assay according to some other embodiments of the disclosure.

FIGS. 9A-9B are graphical representation of diffusion characteristics within a chamber of a microfluidic device according to some embodiments of the disclosure.

FIGS. 10A-10B are graphical representation of diffusion characteristics within a chamber of a microfluidic device according to some other embodiments of the disclosure.

FIGS. 12A-12C are graphical and photographic representations of diffusion characteristics within a chamber of a microfluidic device and an area of interest for assessing levels of secretion of a product from a biological micro-object, according to some embodiments of the disclosure.

FIG. 32 illustrate sequestration pens with photobleaching, in accordance with various embodiments.

Figure 1A:
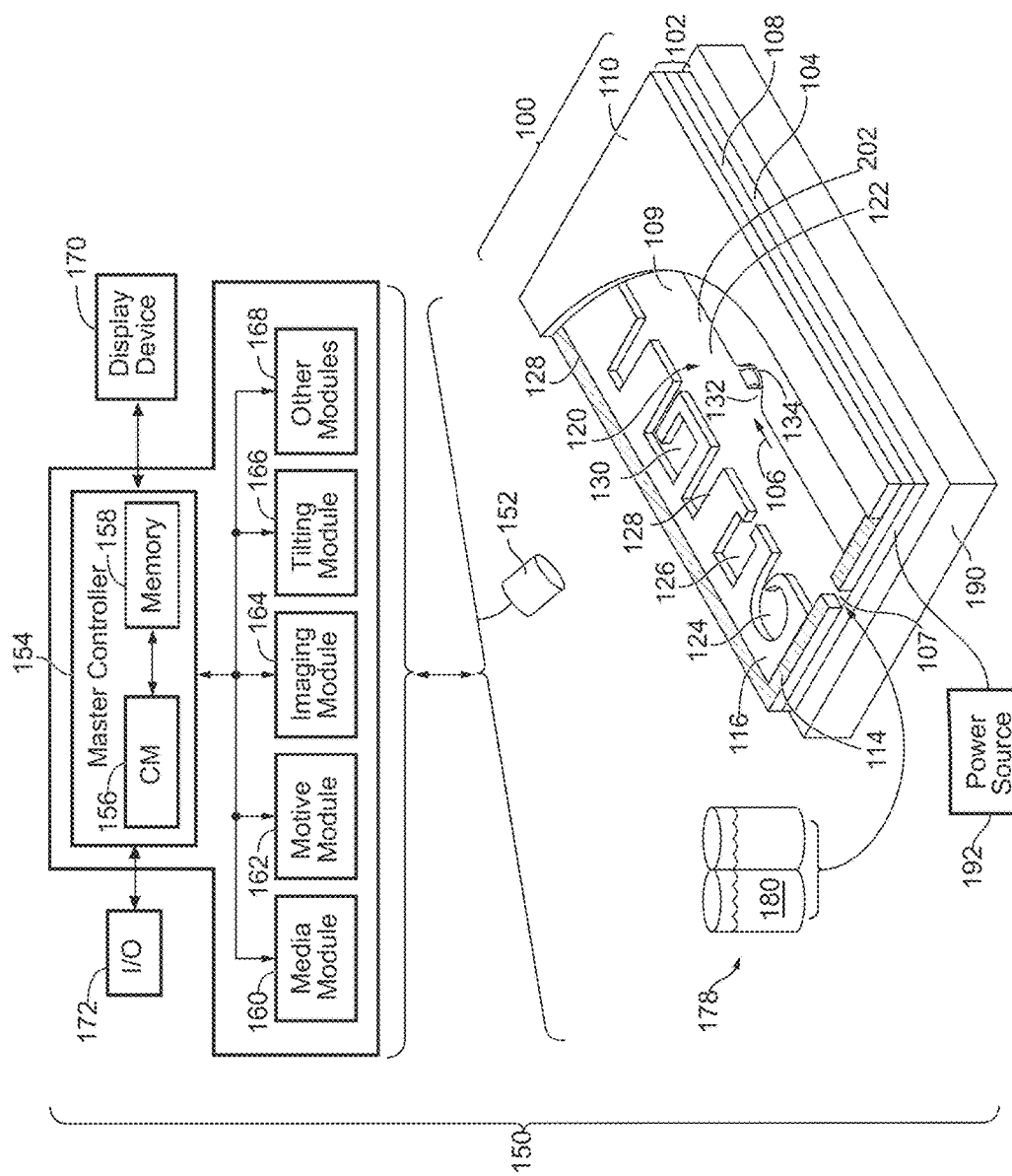
FIG. 1A illustrates an example of a system for use with a microfluidic device and associated control equipment according to some embodiments of the disclosure.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 μL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 μL. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 µL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A microfluidic device or a nanofluidic device may be referred to herein as a "microfluidic chip" or a "chip"; or "nanofluidic chip" or "chip".

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is about 100,000 microns to about 500,000 microns, including any value therebetween. In some embodiments, the horizontal dimension is about 100 microns to about 1000 microns (e.g., about 150 to about 500 microns) and the vertical dimension is about 25 microns to about 200 microns, (e.g., from about 40 to about 150 microns). It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, the connection region and the isolation region of a microfluidic sequestration pen.

As used herein, the term "constriction" refers generally to a narrowing of a width of a circuit element (or an interface between two circuit elements) in a microfluidic device. The constriction can be located, for example, at the interface between the isolation region and the connection region of a microfluidic sequestration pen of the instant disclosure.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein, "capture moiety" is a chemical or biological species, functionality, or motif that provides a recognition site for a micro-object. A selected class of micro-objects may recognize the in situ-generated capture moiety and may bind or have an affinity for the in situ-generated capture moiety. Non-limiting examples include antigens, antibodies, and cell surface binding motifs.

As used herein, "flowable polymer" is a polymer monomer or macromer that is soluble or dispersible within a fluidic medium (e.g., a pre-polymer solution). The flowable polymer may be input into a microfluidic flow region and flow with other components of a fluidic medium therein.

As used herein, "photoinitiated polymer" refers to a polymer (or a monomeric molecule that can be used to generate the polymer) that upon exposure to light, is capable of crosslinking covalently, forming specific covalent bonds, changing regiochemistry around a rigidified chemical motif, or forming ion pairs which cause a change in physical state, and thereby forming a polymer network. In some instances, a photoinitiated polymer may include a polymer segment bound to one or more chemical moieties capable of crosslinking covalently, forming specific covalent bonds, changing regiochemistry around a rigidified chemical motif, or forming ion pairs which cause a change in physical state. In some instances, a photoinitiated polymer may require a photoactivatable radical initiator to initiate formation of the polymer network (e.g., via polymerization of the polymer).

As used herein, "antibody" refers to an immunoglobulin (Ig) and includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'2 fragments), or multimers or aggregates of intact molecules and/or fragments; and may occur in nature or be produced, e.g., by immunization, synthesis or genetic engineering. An "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'2, scFv, light chain variable region (VL), heavy chain variable region (VH), and combinations thereof.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device.

Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to assess which, if any, of the biological micro-objects in the unswept region are sufficient producers of the analyte of interest.

Microfluidic devices and systems for operating and observing such devices. FIG. 1A illustrates an example of a microfluidic device 100 and a system 150 which can be used for maintaining, isolating, assaying or culturing biological micro-objects. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 can be at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device 194 (incorporated within imaging module 164, where device 194 is not illustrated in FIG. 1A, per se), and a tilting device 190 (part of tilting module 166, where device 190 is not illustrated in FIG. 1A).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 (part of imaging module 164, discussed below) can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device 194 may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for maintaining, isolating, assaying or culturing biological micro-objects. In some embodiments, the microfluidic circuit 120 comprises a plurality of identical microfluidic sequestration pens.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
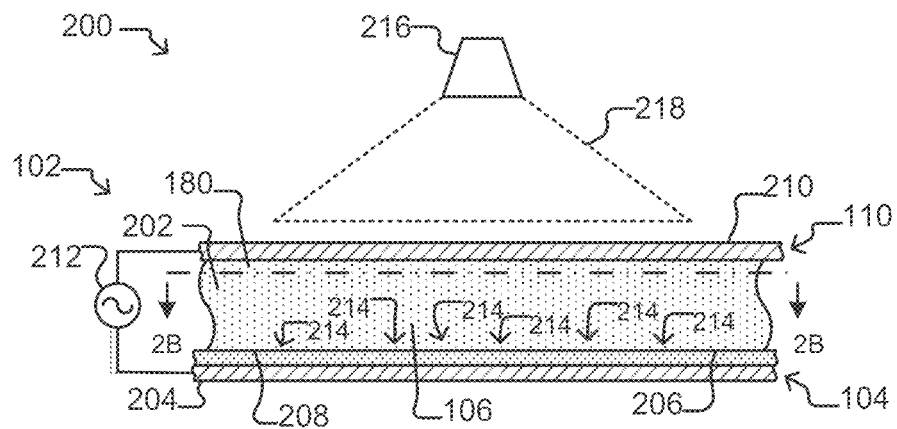
FIGS. 1B and 1C illustrate a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which biological micro-objects can be placed, cultured, and/or monitored have been described, for example, in US 2014/0116881 (application Ser. No. 14/060,117, filed Oct. 22, 2013), US 2015/0151298 (application Ser. No. 14/520,568, filed Oct. 22, 2014), and US 2015/0165436 (application Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

Microfluidic device motive configurations. As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
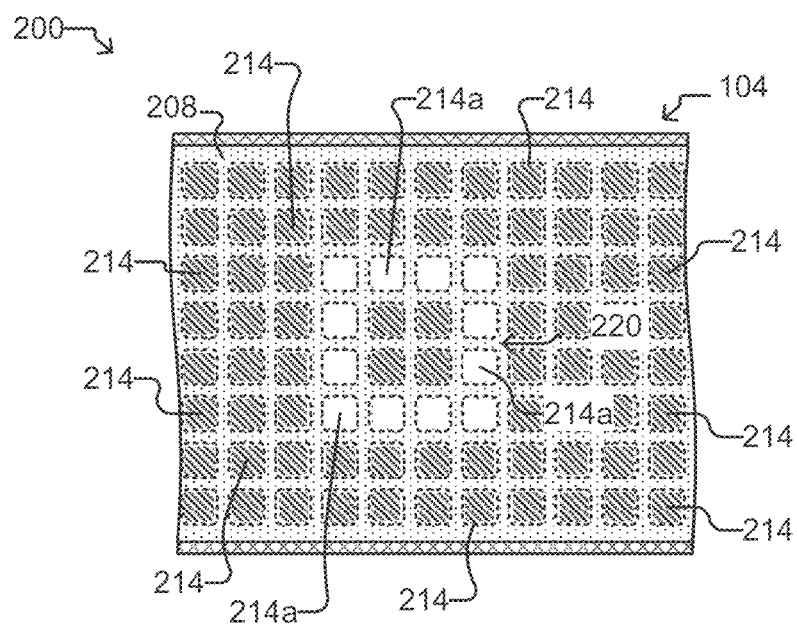

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having a region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 μm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration pens. Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

Figure 2A:
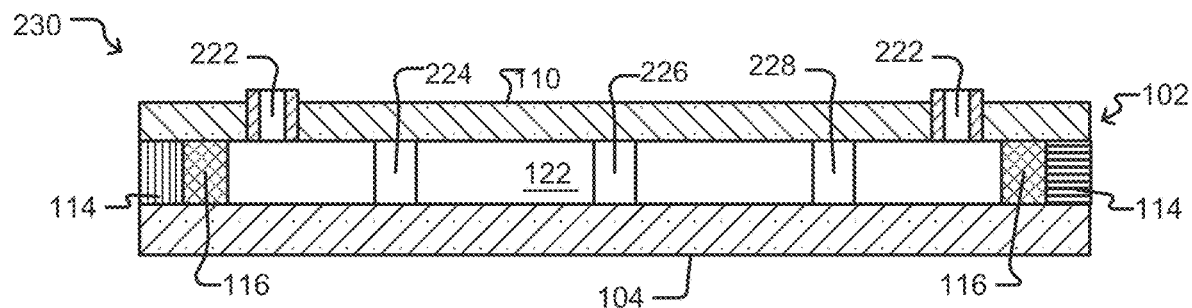
FIGS. 2A and 2B illustrate isolation pens according to some embodiments of the disclosure.
Figure 2B:
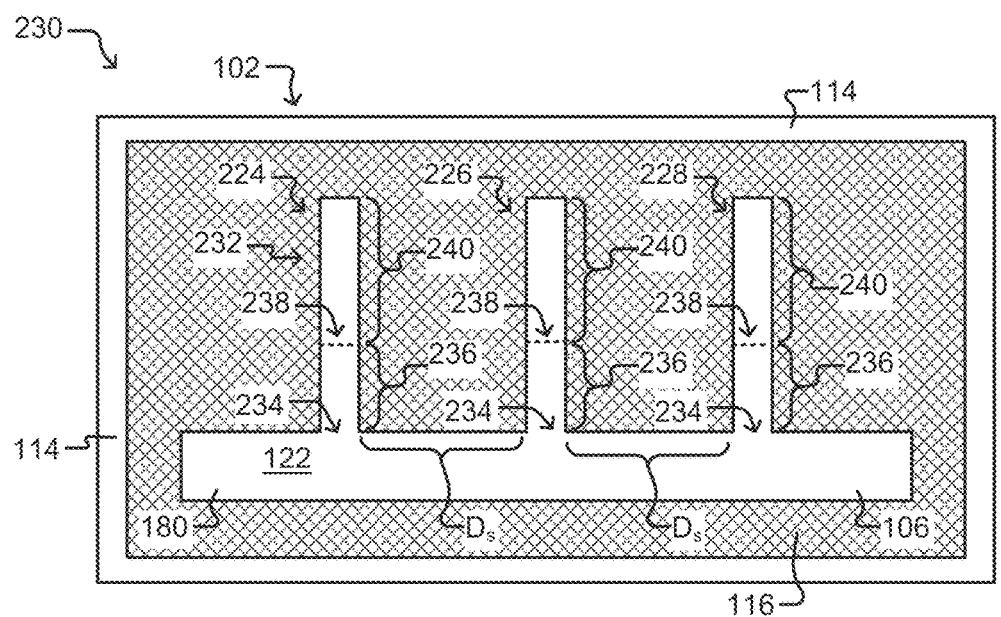
Figure 2C:
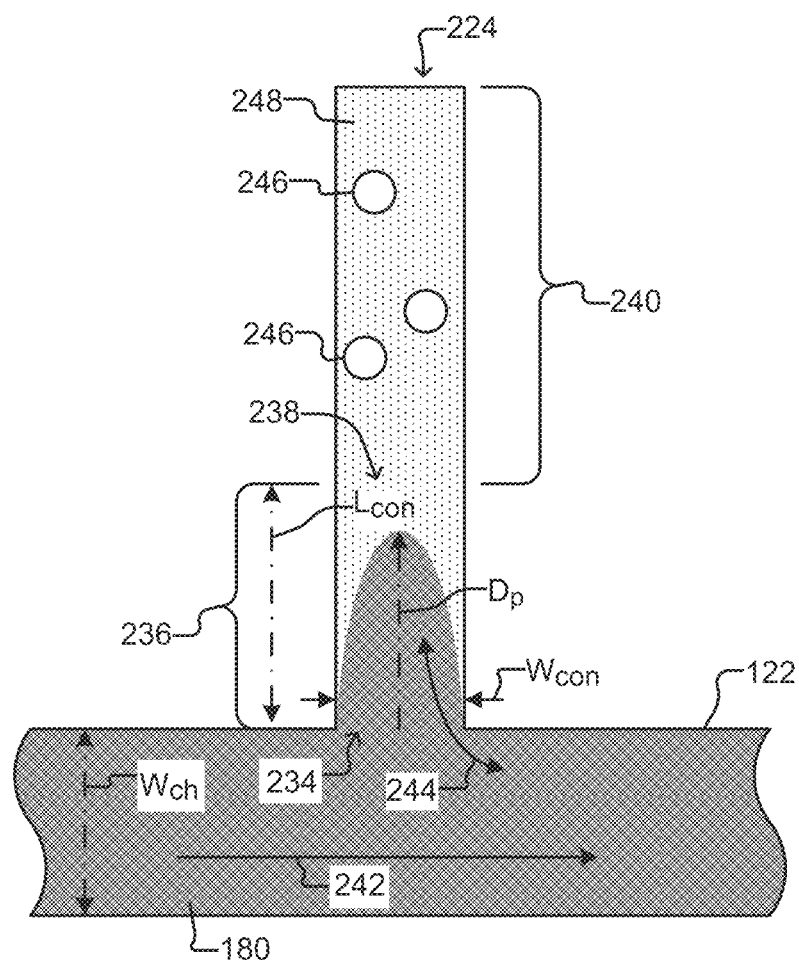
FIG. 2C illustrates a detailed sequestration pen according to some embodiments of the disclosure.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290, 300, 400, 500, 900, 1000, 1100, 1200 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width con of $W_{con}$ the connection region 236 can be uniform from the proximal opening 234 to the distal opening 238. The width $W_{con}$ of the connection region 236 at the distal opening 238 can thus be any of the values identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be any of the values identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
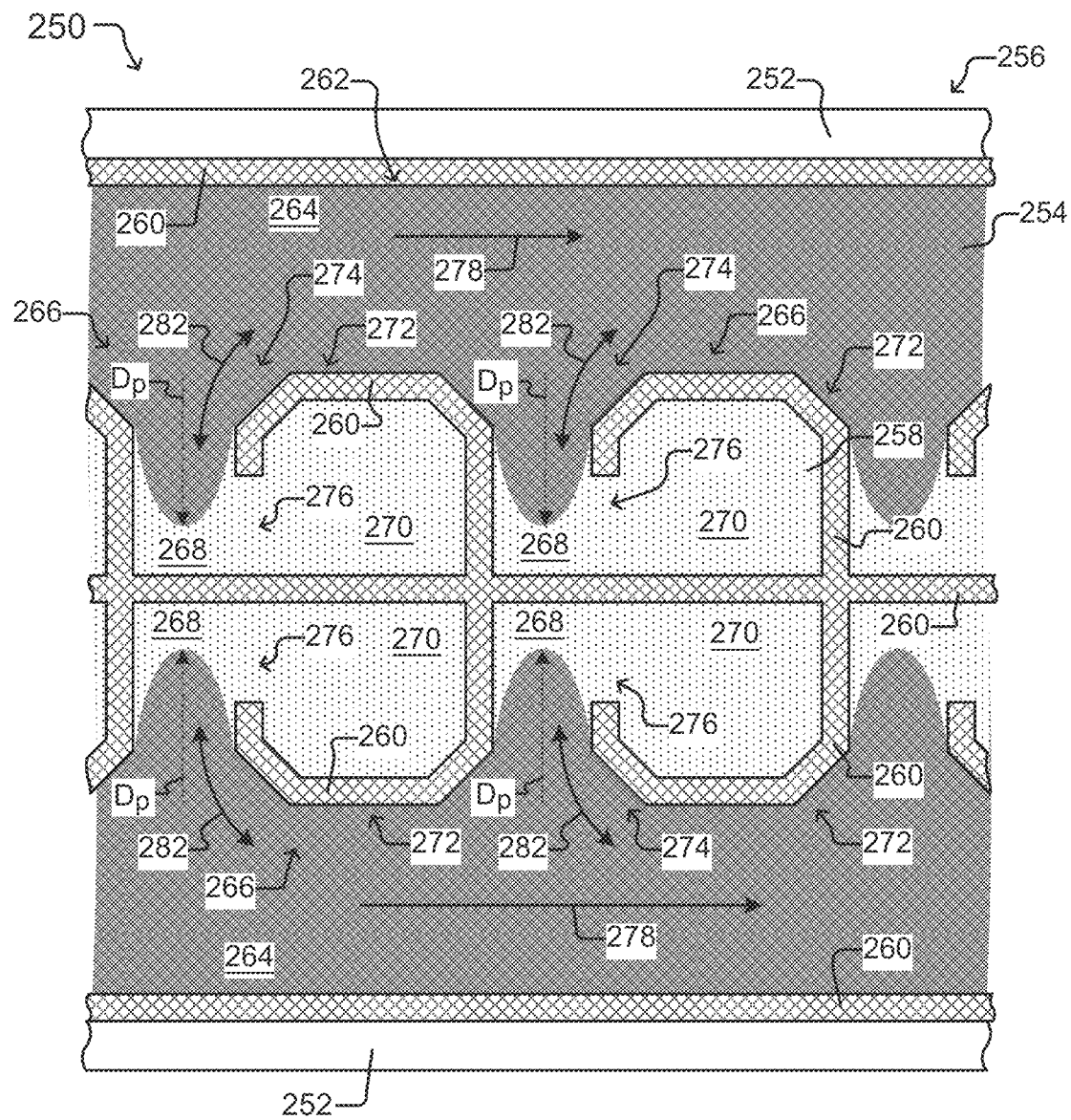
FIGS. 2D-F illustrate sequestration pens according to some other embodiments of the disclosure.
Figure 2E:
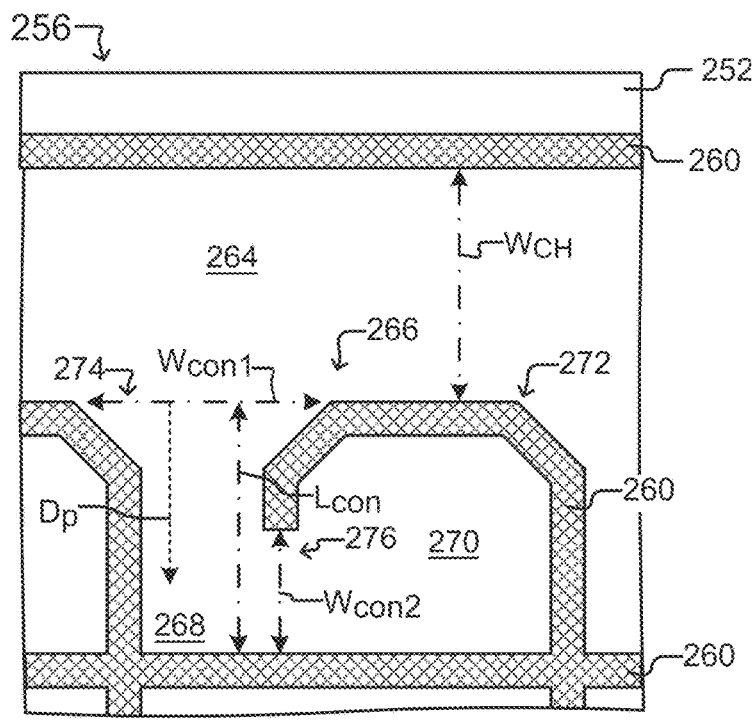
Figure 2F:
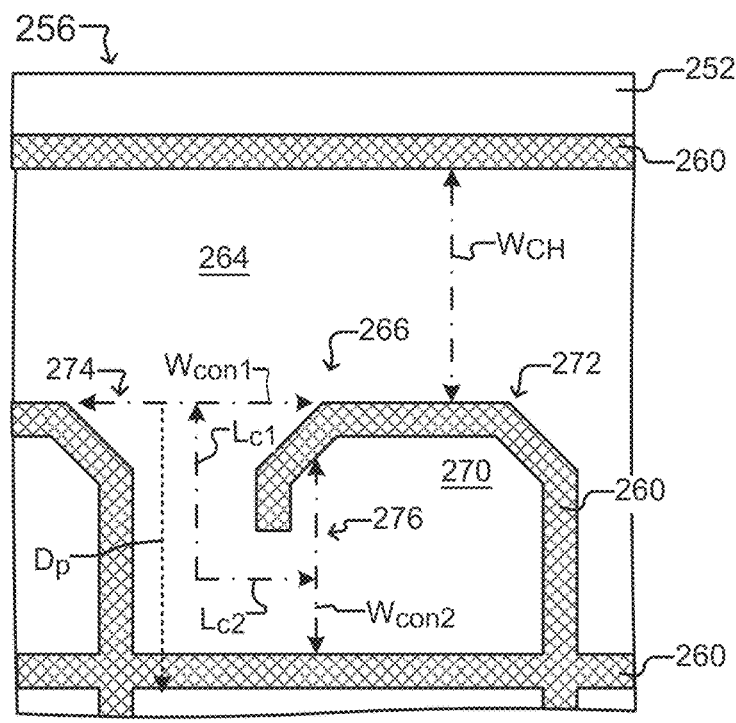

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290, 300 400, 500, 900, 1000, 1100, 1200. Likewise, the microfluidic device 250 is another variant of the microfluidic device 100, and may also have the same or a different DEP configuration as the above-described microfluidic device 100, 200, 230, 280, 290, 300, 400, 500, 900, 1000, 1100, 1200 as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles of: about 30° to about 90°, about 45° to about 90°, about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1\times10^6$, $2\times10^6$, $4\times10^6$, $6\times10^6$ cubic microns, or more.

In various embodiments of sequestration pens, the width $W_{ch}$ of the microfluidic channel (e.g., 122) at a proximal opening (e.g. 234) can be about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, or 100-120 microns. In some other embodiments, the width $W_{ch}$ of the microfluidic channel (e.g., 122) at a proximal opening (e.g. 234) can be about 200-800 microns, 200-700 microns, or 200-600 microns. The foregoing are examples only, and the width $W_{ch}$ of the microfluidic channel 122 can be any width within any of the endpoints listed above. Moreover, the $W_{ch}$ of the microfluidic channel 122 can be selected to be in any of these widths in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1\times10^4$-$3\times10^6$ square microns, $2\times10^4$-$2\times10^6$ square microns, $4\times10^4$-$1\times10^6$ square microns, $2\times10^4$-$5\times10^5$ square microns, $2\times10^4$-$1\times10^5$ square microns or about $2\times10^5$-$2\times10^6$ square microns.

In various embodiments of sequestration pens, the height $H_{ch}$ of the microfluidic channel (e.g., 122) at a proximal opening (e.g., 234) can be a height within any of the following heights: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be a height within any of the endpoints listed above. The height $H_{ch}$ of the microfluidic channel 122 can be selected to be in any of these heights in regions of the microfluidic channel other than at a proximal opening of a sequestration pen.

In various embodiments of sequestration pens a cross-sectional area of the microfluidic channel (e.g., 122) at a proximal opening (e.g., 234) can be about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be any area within any of the endpoints listed above.

In various embodiments of sequestration pens, the length $L_{con}$ of the connection region (e.g., 236) can be about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in any length within any of the endpoints listed above.

In various embodiments of sequestration pens, the width $W_{con}$ of a connection region (e.g., 236) at a proximal opening (e.g., 234) can be about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, or 80-100 microns. The foregoing are examples only, and the width $W_{con}$ of a connection region (e.g., 236) at a proximal opening (e.g., 234) can be different than the foregoing examples (e.g., any value within any of the endpoints listed above).

In various embodiments of sequestration pens, the width $W_{con}$ of a connection region (e.g., 236) at a proximal opening (e.g., 234) can be at least as large as the largest dimension of a micro-object (e.g., biological cell which may be a T cell, B cell, or an ovum or embryo) that the sequestration pen is intended for. The foregoing are examples only, and the width $W_{con}$ of a connection region (e.g., 236) at a proximal opening (e.g., 234) can be different than the foregoing examples (e.g., a width within any of the endpoints listed above).

In various embodiments of sequestration pens, the width $W_{pr}$ of a proximal opening of a connection region may be at least as large as the largest dimension of a micro-object (e.g., a biological micro-object such as a cell) that the sequestration pen is intended for. For example, the width $W_{p}r$ may be about 50 microns, about 60 microns, about 100 microns, about 200 microns, about 300 microns or may be about 50-300 microns, about 50-200 microns, about 50-100 microns, about 75-150 microns, about 75-100 microns, or about 200-300 microns.

In various embodiments of sequestration pens, a ratio of the length $L_{con}$ of a connection region (e.g., 236) to a width $W_{con}$ of the connection region (e.g., 236) at the proximal opening 234 can be $W_{con}$ greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 236 to a width $W_{con}$ of the connection region 236 at the proximal opening 234 can be different $W_{con}$ than the foregoing examples.

In various embodiments of microfluidic devices 100, 200, 23, 250, 280, 290, 300, 400, 500, 900, 1000, 1100, 1200, $V_{max}$ can be set around 0.2, 0.5, 0.7, 1.0, 1.3, 1.5, 2.0, 2.5, 3.0, 3.5, 4.0, 4.5, 5.0, 5.5, 6.0, 6.7, 7.0, 7.5, 8.0, 8.5, 9.0, 10, 11, 12, 13, 14, or 15 microliters/sec.

In various embodiments of microfluidic devices having sequestration pens, the volume of an isolation region (e.g., 240) of a sequestration pen can be, for example, at least $5\times10^5$, $8\times10^5$, $1\times10^6$, $2\times10^6$, $4\times10^6$, $6\times10^6$, $8\times10^6$, $1\times10^7$, $5\times10^7$, $1\times10^8$, $5\times10^8$, or $8\times10^8$ cubic microns, or more. In various embodiments of microfluidic devices having sequestration pens, the volume of a sequestration pen may be about $5\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some other embodiments, the volume of a sequestration pen may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, about 1000 to about 3500 sequestration pens, about 3000 to about 7000 sequestration pens, about 5000 to about 10,000 sequestration pens, about 9,000 to about 15,000 sequestration pens, or about 12,000 to about 20,000 sequestration pens. The sequestration pens need not all be the same size and may include a variety of configurations (e.g., different widths, different features within the sequestration pen).

In various embodiments, sequestration pens 424, 426, 428, 524, 526, 528, 624, 924, 1024, 1124, 1126, 1424, 1426 may have any of the features, dimensions or components as described herein, in any combination.

Figure 2G:
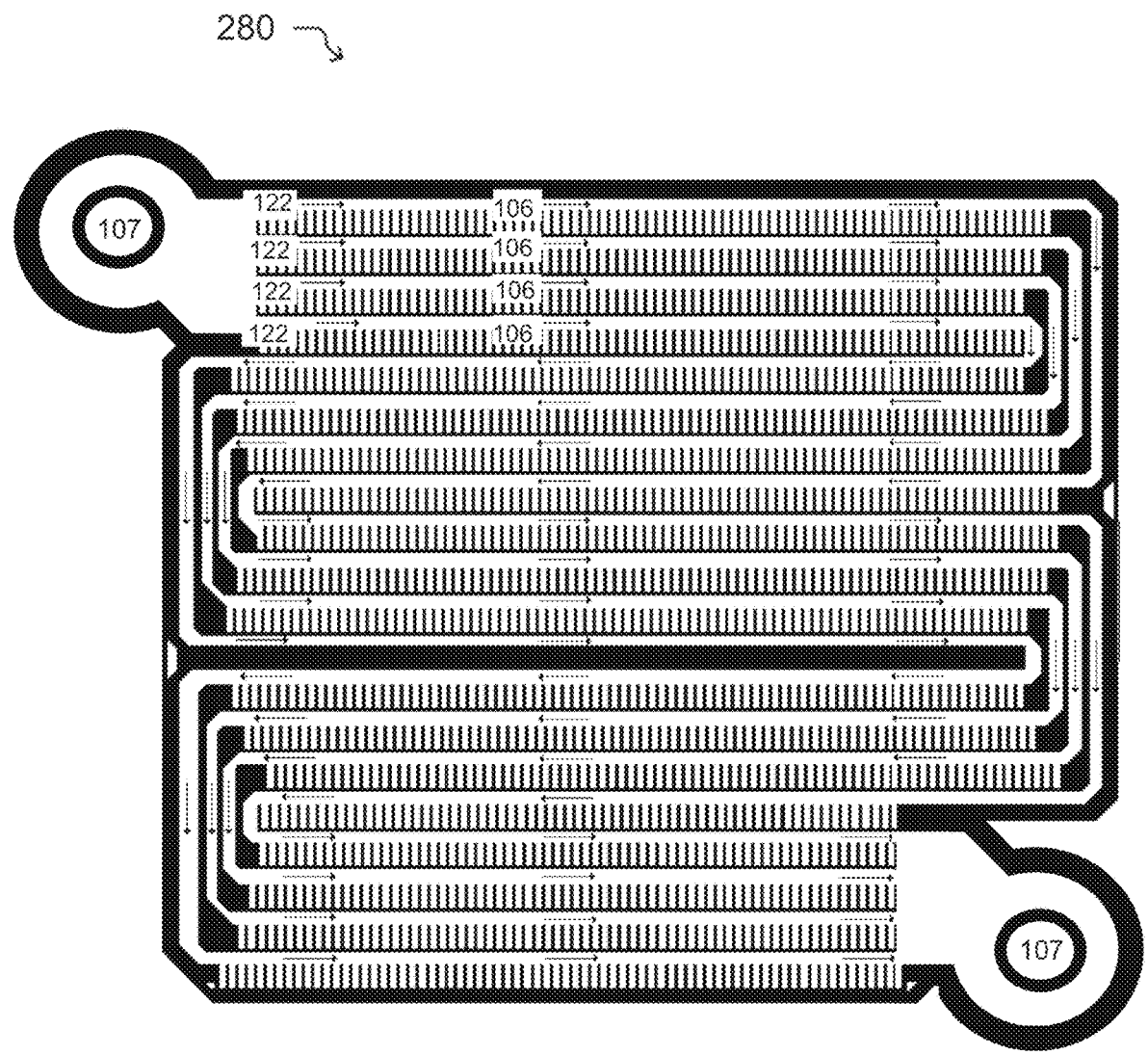
FIG. 2G illustrates a microfluidic device according to an embodiment of the disclosure.

FIG. 2G illustrates a microfluidic device 280 according to one embodiment. The microfluidic device 280 illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Figure 3A:
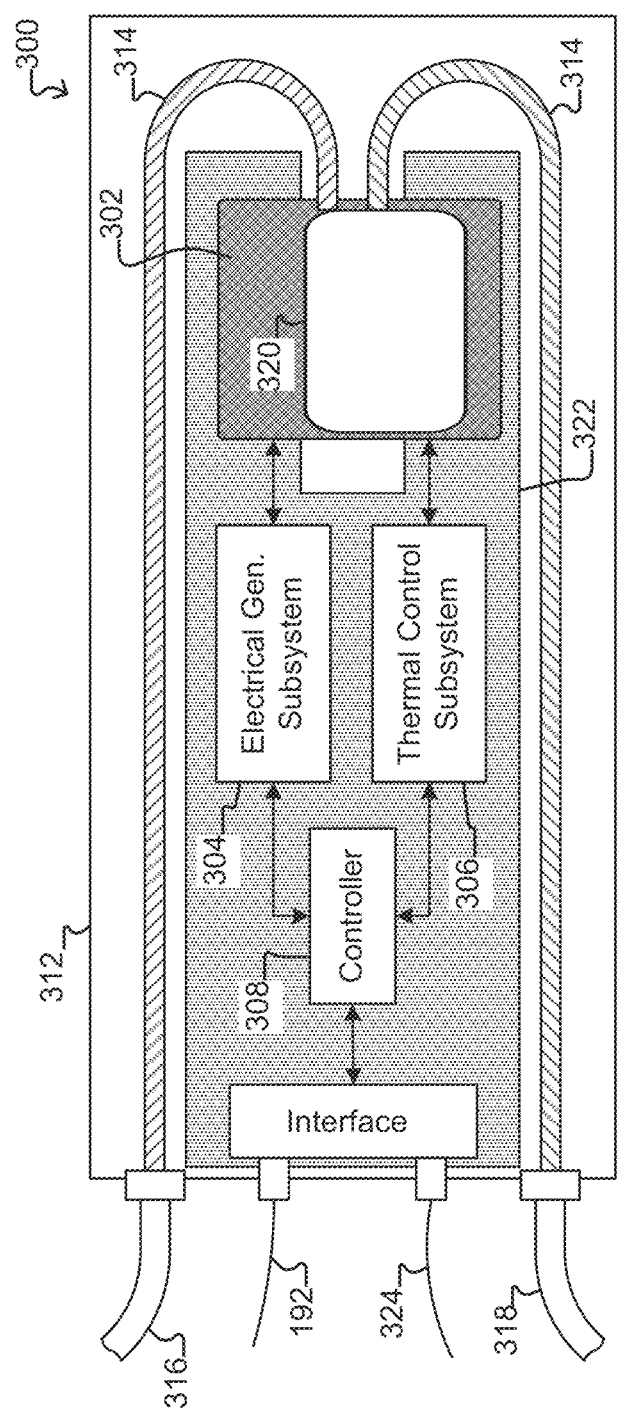
FIG. 3A illustrates a specific example of a system for use with a microfluidic device and associated control equipment according to some embodiments of the disclosure.
Figure 3B:
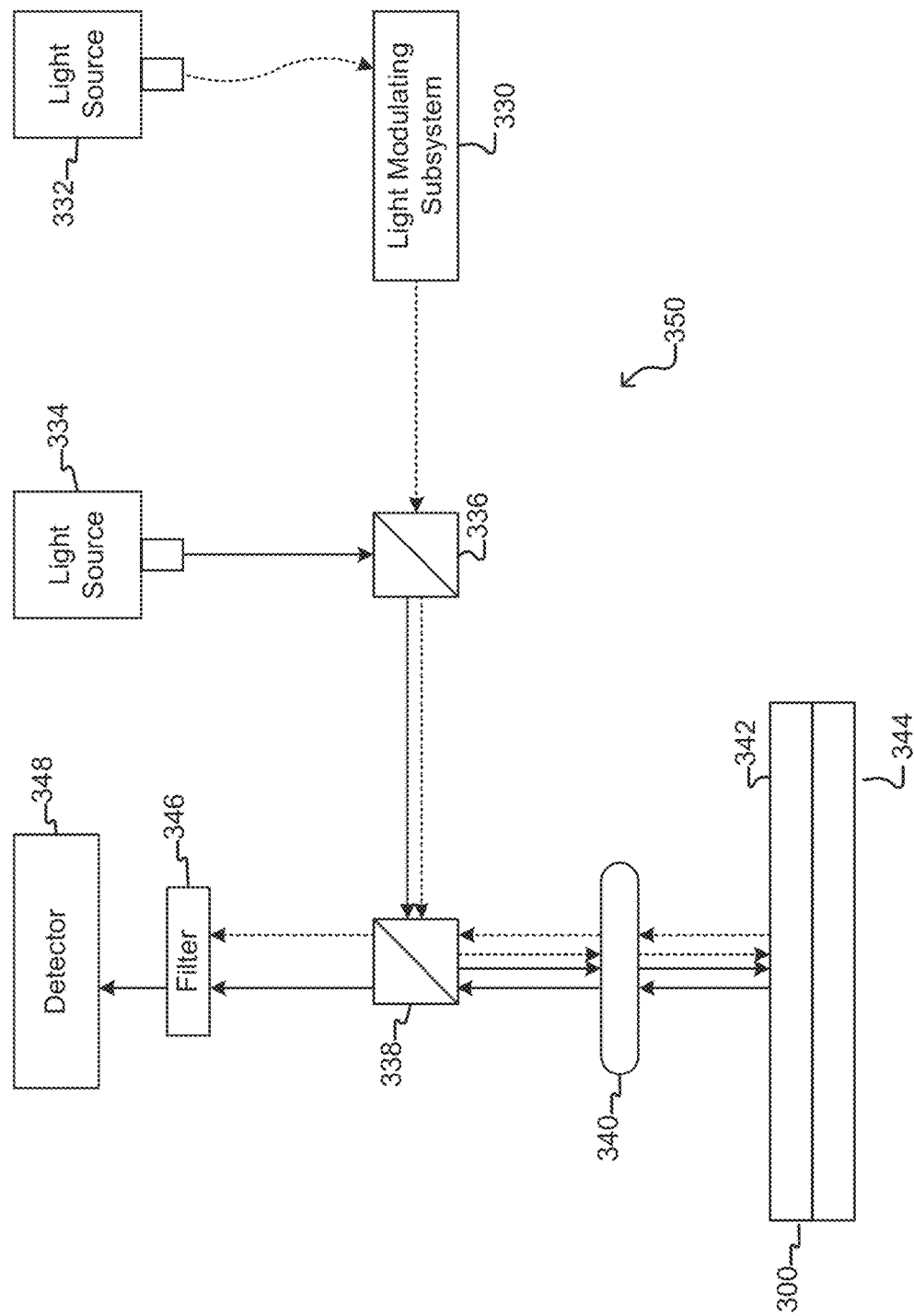
FIG. 3B illustrates an imaging device according to some embodiments of the disclosure.

FIGS. 3A through 3B shows various embodiments of system 150 which can be used to operate and observe microfluidic devices (e.g. 100, 200, 230, 250, 280, 290, 300, 400, 500, 900, 1000, 1100, 1200) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/C0) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. In certain embodiments, imaging module 164 and/or motive module 162 of system 150 can control the light modulating subsystem 330.

In certain embodiments, the imaging device 194 further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device 194 is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region. In other embodiments, the second light source 334 may additionally or alternatively include a laser, which may have any suitable wavelength of light. The representation of the optical system shown in FIG. 3B is a schematic representation only, and the optical system may include additional filters, notch filters, lenses and the like. When the second light source 334 includes one or more light source(s) for brightfield and/or fluorescent excitation, as well as laser illumination the physical arrangement of the light source(s) may vary from that shown in FIG. 3B, and the laser illumination may be introduced at any suitable physical location within the optical system. The schematic locations of light source 334 and light source 332/light modulating subsystem 330 may be interchanged as well.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Coating solutions and coating agents. Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating agent/Solution. Any convenient coating agent/coating solution can be used, including but not limited to: serum or serum factors, bovine serum albumin (BSA), polymers, detergents, enzymes, and any combination thereof.

Polymer-based coating materials. The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a concentration from about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a concentration of about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently linked coating materials. In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprise carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned surface properties. Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). In some embodiments, the conditioned surface has a thickness of about 1 nm to about 10 nm; about 1 nm to about 7 nm; about 1 nm to about 5 nm; or any individual value therebetween. In other embodiments, the conditioned surface formed by the covalently linked moieties may have a thickness of about 10 nm to about 50 nm. In various embodiments, the conditioned surface prepared as described herein has a thickness of less than 10 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). These values are in contrast to that of a surface prepared by spin coating, for example, which may typically have a thickness of about 30 nm. In some embodiments, the conditioned surface does not require a perfectly formed monolayer to be suitably functional for operation within a DEP-configured microfluidic device.

In various embodiments, the coating material providing a conditioned surface of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-part conditioned surface. The covalently linked coating material may be formed by reaction of a molecule which already contains the moiety configured to provide a layer of organic and/or hydrophilic molecules suitable for maintenance/expansion of biological micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of biological micro-object(s) to a surface modifying ligand that itself has been covalently linked to the surface.

Methods of preparing a covalently linked coating material. In some embodiments, a coating material that is covalently linked to the surface of a microfluidic device (e.g., including at least one surface of the sequestration pens and/or flow regions) has a structure of Formula 1 or Formula 2. When the coating material is introduced to the surface in one step, it has a structure of Formula 1, while when the coating material is introduced in a multiple step process, it has a structure of Formula 2.

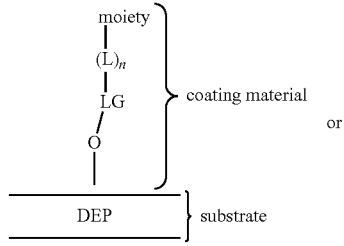

Formula 1

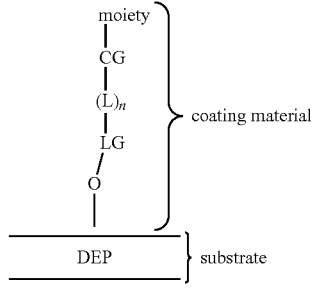

Formula 2

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and/or phosphorus atoms, subject to chemical bonding limitations as is known in the art. It may be interrupted with any combination of one or more moieties, which may be chosen from ether, amino, carbonyl, amido, and/or phosphonate groups, arylene, heteroarylene, or heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of biological micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of biological micro-object(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate), by exposure to a solvent bath, sonication or a combination thereof. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Without intending to be limited by theory, depositing such a coating material on a fully-assembled microfluidic circuit 120 may be beneficial in preventing delamination caused by a weakened bond between the microfluidic circuit material 116 and the electrode activation substrate 206 dielectric layer and/or the cover 110. In embodiments where a two-step process is employed the surface modifying ligand may be introduced via vapor deposition as described above, with subsequent introduction of the moiety configured provide a layer of organic and/or hydrophilic molecules suitable for maintenance/expansion of biological micro-object(s). The subsequent reaction may be performed by exposing the surface modified microfluidic device to a suitable coupling reagent in solution.

Figure 2H:
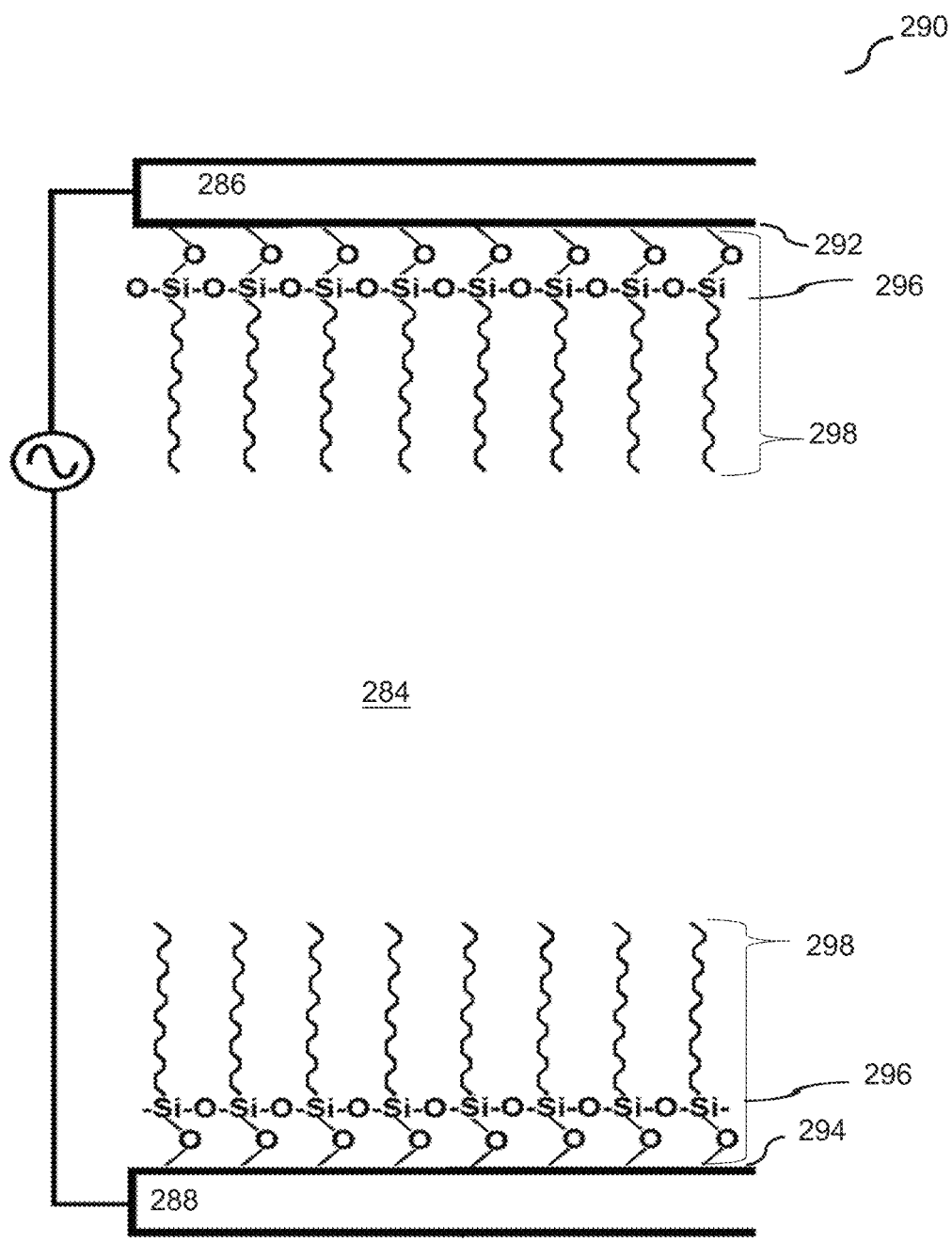
FIG. 2H illustrates a coated surface of the microfluidic device according to an embodiment of the disclosure.

FIG. 2H depicts a cross-sectional view of a microfluidic device 290 having an exemplary covalently linked coating material providing a conditioned surface. As illustrated, the coating materials 298 (shown schematically) can comprise a monolayer of densely-packed molecules covalently bound to both the inner surface 294 of a base 286, which may be a DEP substrate, and the inner surface 292 of a cover 288 of the microfluidic device 290. The coating material 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the coating material 298 can be disposed on only one or some of the inner surfaces of the microfluidic device 290.

In the embodiment shown in FIG. 2H, the coating material 298 can include a monolayer of organosiloxane molecules, each molecule covalently bonded to the inner surfaces 292, 294 of the microfluidic device 290 via a siloxy linker 296. Any of the above-discussed coating materials 298 can be used (e.g. an alkyl-terminated, a fluoroalkyl terminated moiety, a PEG-terminated moiety, a dextran terminated moiety, or a terminal moiety containing positive or negative charges for the organosiloxy moieties), where the terminal moiety is disposed at its enclosure-facing terminus (i.e. the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the coating material 298 can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 can form ionic bonds with the charged portions of non-covalent coating agents (e.g. proteins in solution) that are present in a medium 180 (e.g. a coating solution) in the enclosure 284.

In still other embodiments, the coating material may comprise or be chemically modified to present a hydrophilic coating agent at its enclosure-facing terminus. In some embodiments, the coating material may include an alkylene ether containing polymer, such as PEG. In some embodiments, the coating material may include a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the biological micro-objects from interactions with non-biological molecules (e.g., the silicon and/or silicon oxide of the substrate).

Further details of appropriate coating treatments and modifications may be found at U.S. application Ser. No. 15/135,707, filed on Apr. 22, 2016, and is incorporated by reference in its entirety.

Additional system components for maintenance of viability of cells within the sequestration pens of the microfluidic device. In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

Assaying an analyte secreted by a biological micro-object. In some embodiments, the disclosure provides methods, systems and devices for quantifying a biological molecule present in sequestration pens. In some embodiments, the biological molecule is a secreted analyte of a biological cell or any other biological micro-organism capable of producing a secreted analyte.

In the bioproduction industry, one severe problem is the expense, time and difficulty in identifying clonal populations having desired levels of production and growth habits when employing the currently available instrumentation and workflows. For example, developing a new antibody production line can take many months of work and cost millions of dollars in personnel, equipment and materials. The ability to screen and identify promising clones within a microfluidic device, very early in expanding populations, such as 3, 4, 5, 6, or 7 days after seeding individual founding cells, as described herein, can offer significant time and cost advantages. It has been discovered by Applicant, that the nanofluidic environment, particularly one based on sequestration pens, as described herein, provides exemplary isolation of clonal populations from each other, permitting the ability to obtain assay results from each individual clonal population without contamination from other clonal populations located within the microfluidic device. It has also been discovered that assays to determine the relative or absolute amount of a secreted analyte using the methods described herein, even when performed at an early stage of clonal expansion, can be correlated to production of the desired secreted analyte at more typical macroscale of expansion (e.g. shake flasks, etc.). Further, the ability to screen individual clones at such an early stage can also permit identification of desired clones meeting specific requirements of growth rate and/or more robust production (for example, highly productive clones which are more resistant to levels of a material in the culturing environment such as metabolic waste products or exhausted nutrients).

Another advantage discovered by Applicant is that more complete exploration of a plurality of cells as potential founding cells for a clonal population can be made without use of excessive resources because the nanofluidic chambers (e.g., sequestration pens) described here permit simultaneous growth/assay for up to thousands of individual founding cells at the same time in extremely small volumes.

Additionally, the nanofluidic environment described here permits examination of the effects of specific conditions upon cells, with feedback from repeated assays. For example, conditions and materials, such as culture medium, more closely related to large scale production of a secreted product of a cell (an analyte in the methods herein) may be used to find and characterize the most suitable clones for further examination. In another example, diverse stimulation protocols for B-cell antibody stimulation may be examined in a more reproducible manner, and may be assayed in order to more comparably assess the benefits of one protocol over another.

Detection and quantification using diffusion profiles. As described herein, the amount of a secreted analyte of a biological micro-object may be quantified using a reporter molecule that binds to the secreted analyte. The reporter molecule includes a binding component that binds the secreted analyte to be quantified and a signal component that is used to detect a quantity of the reporter molecule. The reporter molecule has a higher diffusion rate in its unbound state (e.g., not bound to a secreted analyte) than in its bound state (e.g., bound to one or more molecules of the secreted analyte). In some embodiments, the difference in the diffusion rate between the unbound and bound reporter molecules will be a function of the size of secreted analyte molecule(s) that the reporter molecule binds to. In some embodiments, the reporter molecule may bind the secreted analyte in a conformation that slows the rate of diffusion. For example, the reporter molecule may bind multiple copies of the secreted analyte in a conformation in which the secreted analyte is aggregated and diffuses slowly due, in part, to its conformation. The methods described herein exploit the differences in the rate of diffusion between the reporter molecule (unbound) and the bound reporter molecule:analyte complex (RMSA) to quantify the amount of the secreted analyte.

Figure 4A:
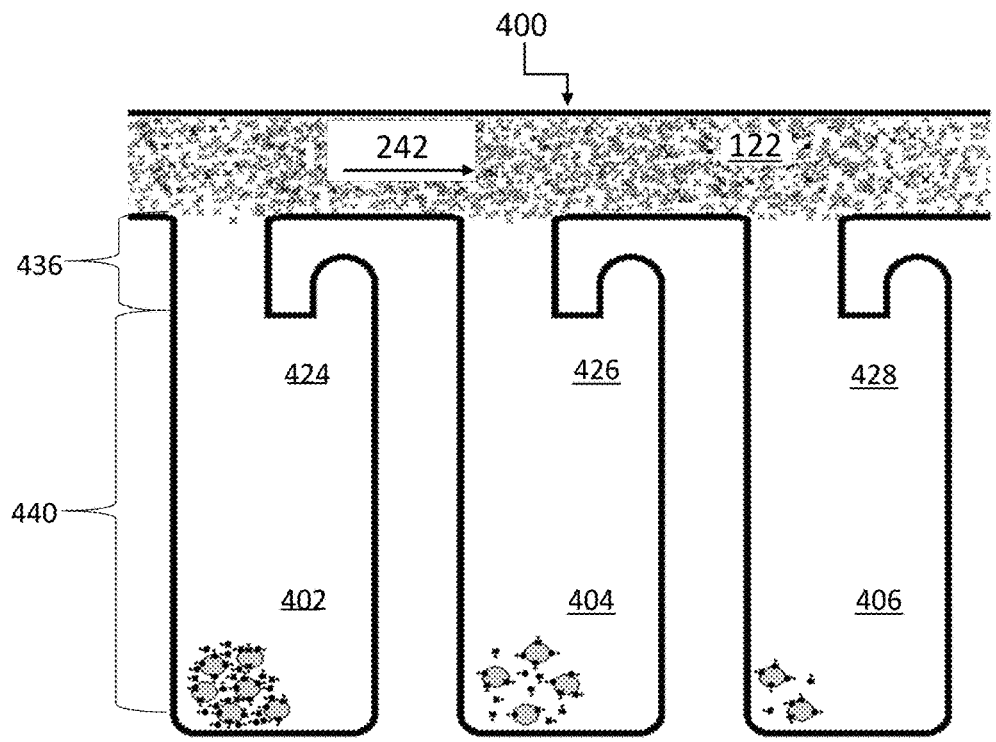
FIGS. 4A-4C are graphical representations of an assay according to some embodiments of the disclosure.
Figure 4B:
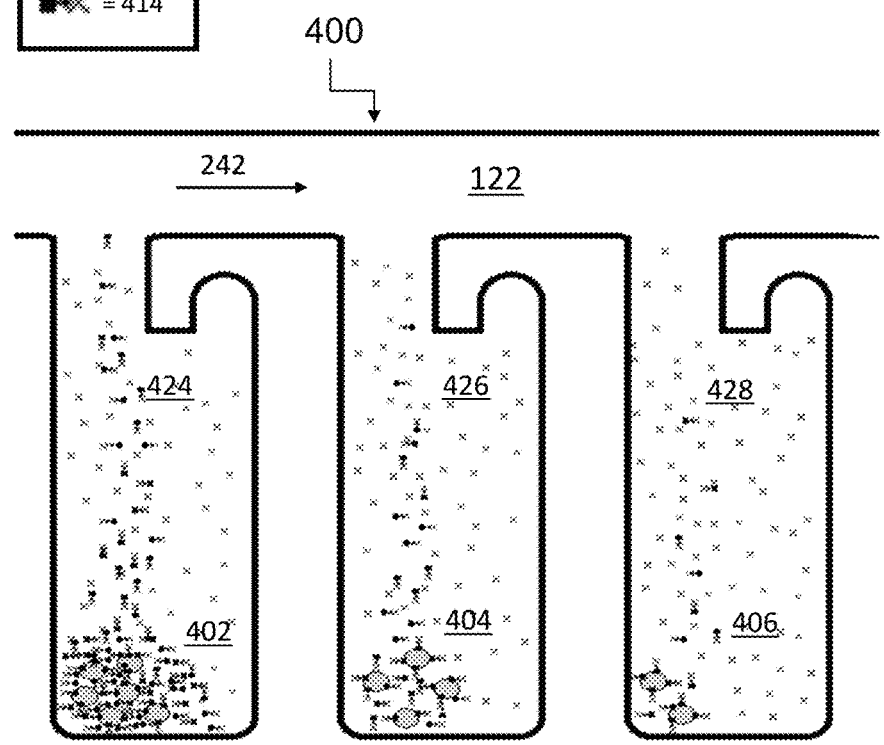
Figure 4C:
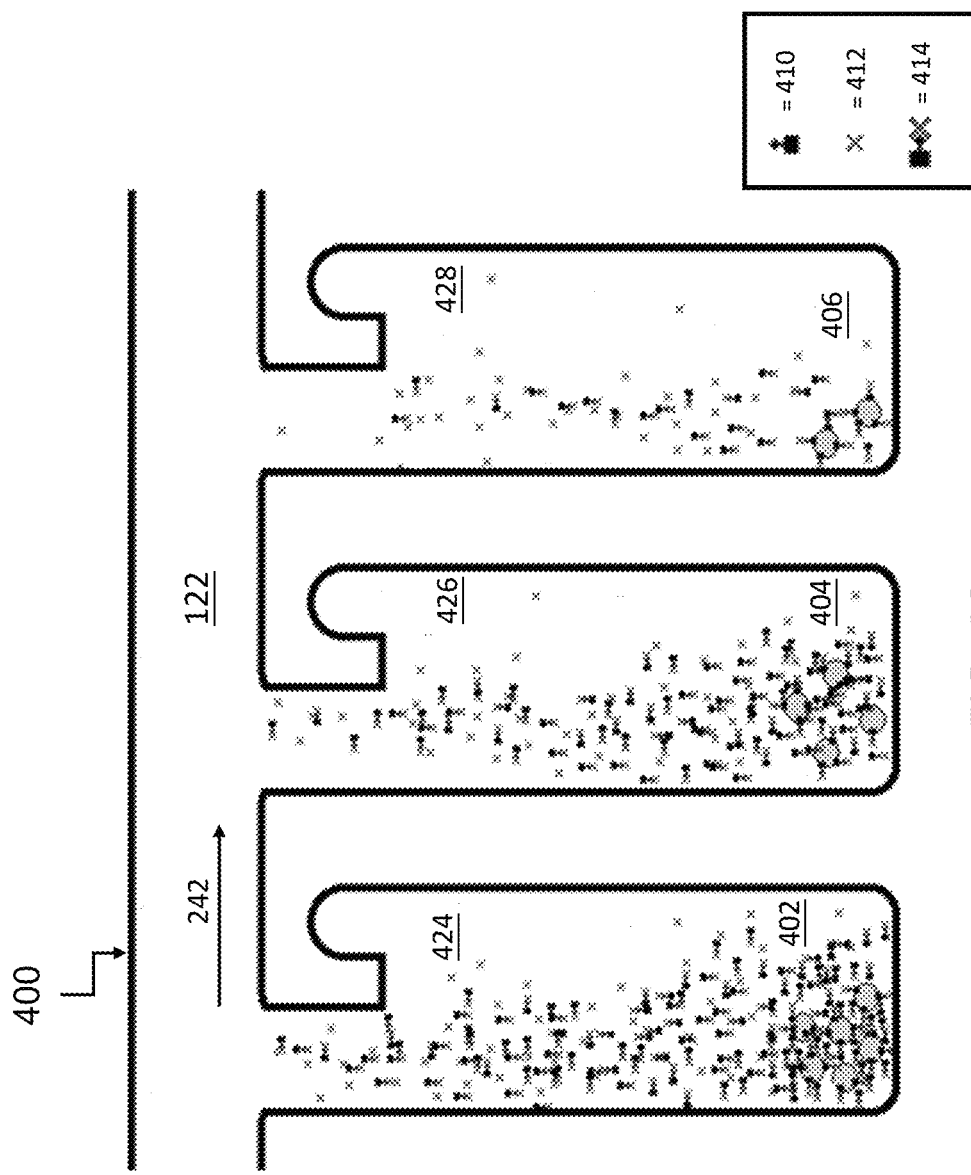

Diffusion assay under flow conditions in the microfluidic channel. FIGS. 4A-4C illustrate an assay according to some embodiments of the disclosure. In FIG. 4A, reporter molecules 412, each having a detectable label, are introduced into the microfluidic channel 122 by flowing a fluid containing a concentration of the reporter molecules 412 within flow 242 into the channel 122 of microfluidic device 400. Sequestration pens 424, 426, 428 are each fluidically connected to the microfluidic channel 122 containing various numbers of cells 402, 404, 406 secreting a biological analyte 410. Each of sequestration pens 424, 426, 428 include a connection region 436 and an isolation region 440 (sequestration pen 424 is the only pen so labeled, just for clarity). The connection region 436 and isolation region 440 have properties as described above, and limit the contact of materials introduced into the channel 122 (e.g., within isolation region 440, materials flowing within the channel 122 may enter the isolation region only by diffusion, not by flow directly into the isolation region.) At the time point illustrated in FIG. 4A, the molecules of the secreted analyte 410 are proximal to the cells.

FIG. 4B illustrates the same region of the microfluidic device as in FIG. 4A at a later time point. The reporter molecules 412 can rapidly diffuse within the channel 122 and sequestration pens 424, 426, 428 such that the concentration of the reporter molecules 412 equilibrate between the channel 122 and the interiors of the sequestration pens 424, 426, 428. As illustrated in FIG. 4B, the reporter molecules 412 have reached a steady-state concentration to be substantially uniform within the sequestration pens 424, 426, 428. The flow 242 of medium containing reporter molecule 412 is replaced by flow 242 of medium containing no reporter molecule 412, and the channel 122 does not contain significant amounts of reporter molecule.

As the reporter molecules 412 within each sequestration pen 424, 426, 428 contact the molecules of secreted analyte 410, the reporter molecules 412 can bind to the analyte 410, forming a reporter molecule:analyte complex 414, and providing a localized detectable signal that is related to the quantity of the secreted analyte 410. As flow 242 continues, reporter molecules diffuse out of the sequestration pen, entering the channel 122 and are exported out of the microfluidic device. However, as shown in FIG. 4B, diffusion of reporter molecule:analyte complex 410 is slower than that of unbound reporter molecule 412, due to its greater molecular weight (and effective size) and differentially does not diffuse as rapidly out of the sequestration pens 424, 426, 428.

FIG. 4C illustrates the same region of the microfluidic device as in FIGS. 4A and 4B at yet a later time point at which the secreted analyte 410 and reporter molecule:analyte complexes 414 are diffusing from the source of the secreted analyte 410 (e.g., cells 402, 404, 406) to the channel 122. Flow 242 continues within the channel 122, thereby permitting reporter molecule 412 to diffuse out of each sequestration pen 424, 426, 428 more rapidly than reporter molecule:analyte complex 410.

The reporter molecule:analyte complex diffuses more slowly because secreted analyte molecules 410 may have a greater molecular weight (and associated effective size in solution) than the reporter molecules 412. In embodiments where the secreted analyte is an antibody and the reporter molecule is a peptide or aptamer, the difference in molecular weight is significant. In any case, the weight (and accordingly, the size) of the bound reporter molecule:analyte complex 414 is greater than that of the unbound reporter molecule 412 and, therefore, the reporter molecule:analyte complex 414 can diffuse more slowly than the unbound reporter molecule 412, providing a distinct diffusion profile and associated detectable signal, relative to the uniform signal provided by the unbound reporter molecules 412. Additionally, the biological micro-objects 502, 504, 506 continue to secrete the analyte 410, providing more targets for binding with reporter molecules 412 which are still disposed within the sequestration pens 524,526,528. A time point can be selected where the percentage of unbound reporter molecules diffusing or already diffused out of the sequestration pen exceeds a threshold value, permitting imaging of detectable signal from substantially or predominately only reporter molecule:analyte complex 414 within each sequestration pen 424, 426, 428. In some embodiments, an assay image is acquired when the amount of unbound reporter molecules 412 that have diffused out of the sequestration pen is about 10%, 15%, 20%, 25%, 30%, 35%, 40%, 45%, 50%, 55%, 60%, 65%, 70%, 75%, 80%, 85%, 90%, or any range defined by two of the foregoing values. Alternatively, or in addition, in some embodiments an assay image is acquired when the amount of unbound reporter molecules 412 that have diffused out of the sequestration pen is about 1.25×, 1.5×, 2.0×, 2.5×, 3.0×, 3.5×, 4.0×, 4.5×, 5.0×, 7.5×, 10×, 25×, 50×, or 100× greater than an amount of bound reporter molecule:analyte complexes 414 that have diffused out of the sequestration pen The detectable signals obtained in the assay image may be proportional to the number of biological micro-objects in the pens. Sequestration pen 424 is illustrated as containing 6 biological micro-objects, sequestration pen 426 is illustrated as containing 4 biological micro-objects and sequestration pen 428 is illustrated as containing 2 biological micro-objects, and in some embodiments, the assay signal from the respective sequestration pens may be proportional to those numbers of cells. In some embodiments, secretion of the analyte may depend on the cell cycle state at the assay signal acquisition time, and the signal from each of a plurality of sequestration pens may not be substantially proportional to the number of cells within each sequestration pen. Additionally, as illustrated in FIG. 4C, while all of the cells 402, 404, 406 are secreting the analyte 410, different populations of cells (e.g., different clones) may secrete the biological analyte 410 at varying rates. Therefore the amount of analyte 410 produced (and the resulting intensity of the diffusion profile signal detected from the reporter molecule:analyte complex 414) may not be the same, pen to pen, even when normalized for the number of cells 402, 404, 406 present in each pen. One or more assay images may be obtained during this period of time, which may be used to characterize the amount of secreted analyte 410 within the imaged sequestration pens 424, 426, 428. Description of the analysis performed to arrive at relative or absolute quantification of the amount of secreted analyte 410 produced follows below.

As stated above, the reporter molecule:secreted analyte (RMSA) complex diffuses more slowly because secreted analyte molecules may have a greater molecular weight (and associated effective size in solution) than the reporter molecules. In embodiments where the secreted analyte is an antibody and the reporter molecule is a peptide or aptamer, the difference in molecular weight is significant. In any case, the weight (and accordingly, the size) of the bound RSMA complex is greater than that of the unbound reporter molecule and, therefore, the RSMA complex can diffuse more slowly than the unbound reporter molecule, providing a distinct diffusion profile and associated detectable signal, relative to the uniform signal provided by the unbound reporter molecules.

The keying in on molecular weight differences between unbound reporter and RMSA complex may impact the compatibility of some assay methods discussed herein for workflows that involve the production of small molecular weight molecules (secreted analytes of small molecular weight). Since rate of diffusion is naturally a product of weight/size of the component in question, and distinct diffusion profiles allows for valuable detectable signals to be gathered, it is seemingly not apparent how to slow the diffusion of an assay reagent when binding a small molecular weight molecule that is secreted by cells. Hence, this may result in no discernable difference in diffusion rate between the bound and free fluorescent species, and thus seemingly no clear path to obtain the necessary diffusion profiles to gather the necessary detectable signals. By overcoming this problem, the various embodiments disclosed herein can be implemented in relation to secretion of, for example, small metabolites, biofuels, or other small molecules-of-interest.

Measuring the production of small molecules can be accomplished, for example, by inverting the cell line development assay in accordance with various embodiments, wherein the brighter fluorescing pens will indicate not the highest producing cell lines, but rather the weaker producing lines. In one example, a molecule (e.g., large molecular weight protein or protein complex, referred to as an "anchor") that is known to bind to small molecule targets, will first be bound off-chip with a fluorescent version of the target-of-interest. This fluorescent complex (anchor+fluorescent target) will be equilibrated throughout the chip, including within the pens containing cells that could be secreting non-fluorescence versions of the target. In the presence of these unlabeled targets, binding kinetics will drive the exchange of the labeled targets with unlabeled targets at much higher concentration within the pens. After flushing the channels clear for some time, the fluorescent targets not bound by an anchor will diffuse rapidly from the pen. As a result, when reading fluorescence levels subsequent to this flush, the dimmer observed pens will equate to those secreting more small molecular weight target.

In accordance with various embodiments, therefore, a method is provided for assessing a level of secretion of an analyte by a biological micro-object, or a population of biological micro-objects generated therefrom. The method can comprise introducing the biological micro-object into a sequestration pen of a microfluidic device, wherein the microfluidic device comprises an enclosure having a flow region, wherein the sequestration pen is fluidically connected to the flow region, and wherein the sequestration pen contains a first fluidic medium. The method can further comprise allowing the biological micro-object, or the population of biological micro-objects generated therefrom, to secrete an analyte into the first fluidic medium within the sequestration pen, and introducing a second fluidic medium into the flow region for a first period of time, wherein the second fluidic medium comprises a plurality of reporter complexes. The reporter complex can comprise a first complex component configured to bind the secreted analyte, and a second complex component bound to the first complex. The second complex component can comprise a detectable label. The binding of the first complex component to the secreted analyte can reduce or eliminate binding of the second complex component to the first complex component. The method can further allow a portion of the plurality of reporter complexes to diffuse into the sequestration pen and bind to the analyte secreted therein, thereby producing a plurality of first complex component:secreted analyte (FCCSA) complexes. The method can also comprise detecting second complex components located within an area of interest within the microfluidic device, wherein the area of interest includes at least a portion of the sequestration pen.

Figure 25:
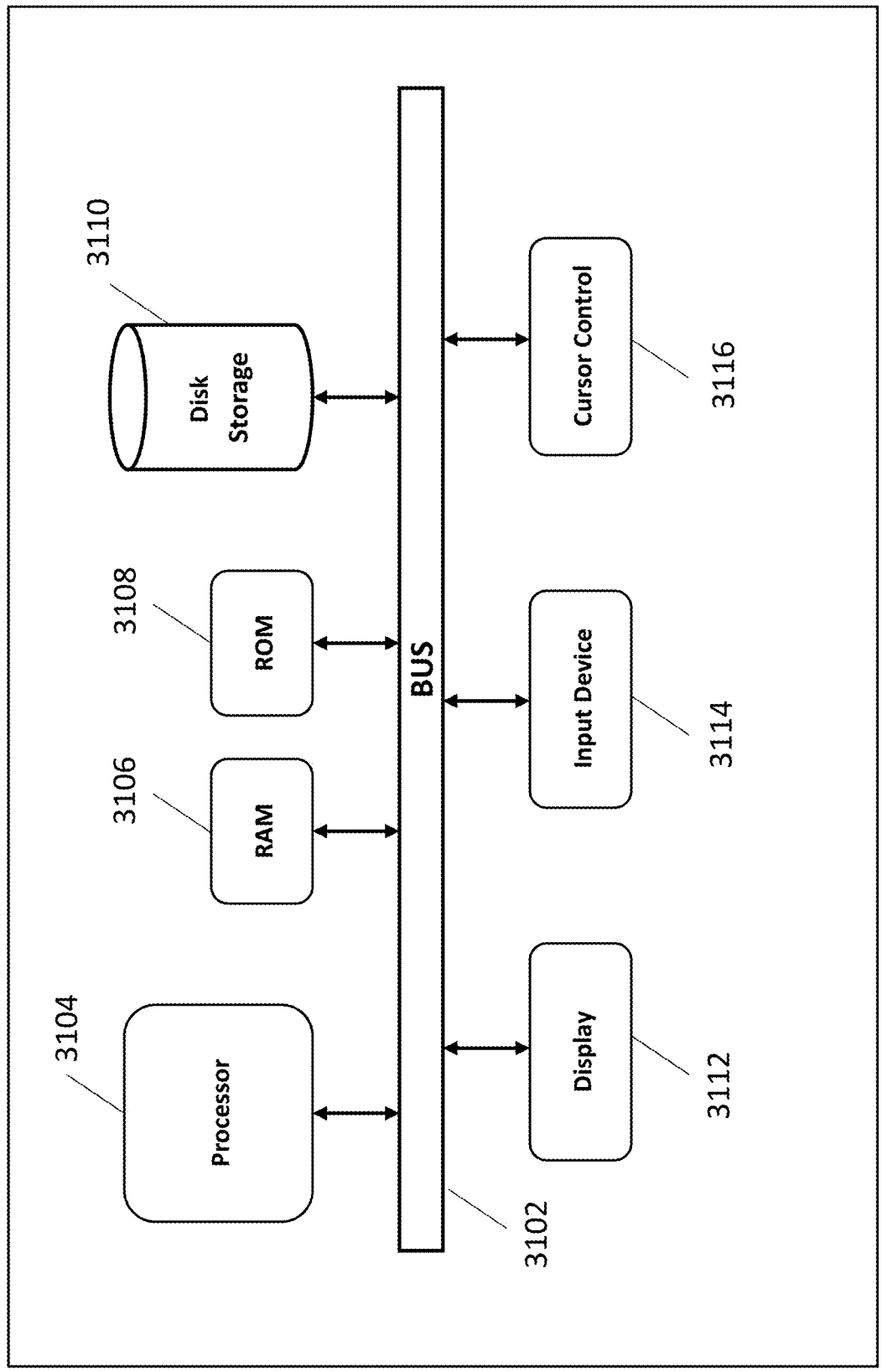
FIG. 25 is a block diagram that illustrates a computer system, in accordance with various embodiments.

In accordance with various embodiments, a non-transitory computer-readable medium is provided in which a program is stored for causing a computer to direct a system to perform a method for determining a quantity of analyte produced by a biological micro-object by producing FCCSA complexes. An example computer system for this is provided by the block diagram of FIG. 25 illustrating a computer system 3100, upon which embodiments of the present teachings may be implemented. Details of computer system 3100 will be provided below.

In accordance with various methods for producing FCCSA complexes, the detectable label can comprise a visible, luminescent, phosphorescent, or fluorescent label. Further, the detectable label of the second complex component can be a fluorescent label, wherein said detecting the second complex components comprises detecting fluorescence emission from the fluorescent label of the second complex components within the area of interest.

In accordance with various methods for producing FCCSA complexes, methods can further include exposing, for a second period of time, a portion of the microfluidic device comprising the sequestration pen to electromagnetic radiation comprising a wavelength which is capable of exciting the fluorescent label of the second complex components. The methods can further include detecting fluorescence emission within the area of interest is performed after the second period of time, detecting fluorescence emission is performed two or more times during a third period of time, and/or detecting fluorescence emission is performed substantially continuously during a third period of time.

In accordance with various methods for producing FCCSA complexes, the sequestration pen can have an isolation region and a connection region fluidically connecting the isolation region to the flow region, wherein the isolation region and the connection region are configured such that components of a fluidic medium in the isolation region are exchanged with components of a fluidic medium in the flow region substantially only by diffusion.

In accordance with various methods for producing FCCSA complexes, the biological micro-object is a biological cell, wherein the method can further comprise expanding the biological cell within the sequestration pen into a clonal population of biological cells.

In accordance with various methods for producing FCCSA complexes, methods can further comprise perfusing the flow region with a culturing medium, wherein the perfusing occurs after introducing the biological micro-object into the sequestration pen and before introducing the second fluidic medium into the flow region.

In accordance with various methods for producing FCCSA complexes, methods can further comprise quantifying the level of secretion of the analyte. The secreted analyte can have a molecular weight less than 5 kD. More specifically, the secreted analyte can have a molecular weight less than 2 kD. Even more particularly, the secreted analyte can have a molecular weight less than 1 kD.

In accordance with various methods for producing FCCSA complexes, the second complex component of the reporter complexes can comprise a peptide having the sequence of any one of SEQ ID NOs: 1 to 10. The second complex component of the reporter complexes can comprise protein A, protein G, or an IgG-binding fragment of protein A or protein G.

In accordance with various methods for producing FCCSA complexes, the secreted analyte competitively inhibits binding of the second complex component to the first complex component. Alternatively, the secreted analyte non-competitively inhibits binding of the second complex component to the first complex component. The secreted analyte can also inhibit binding of the second complex component to the first complex component by an allosteric mechanism.

In accordance with various methods for producing FCCSA complexes, the microfluidic device can comprise a plurality of sequestration pens, wherein a biological micro-object is introduced into at least two sequestration pens of the plurality, and wherein the remainder of the method is carried out with respect to each of the at least two sequestration pens. Methods can further comprise comparing a level of secretion for sequestration pens of the at least two sequestration pens of the plurality of sequestration pens. Methods can further comprise selecting one or more of the at least two sequestration pens, and exporting one or more biological micro-objects from each of the selected sequestration pens.

In accordance with various methods for producing FCCSA complexes, methods can further include applying fluorescence recovery after photobleaching (FRAP) an area (region, area of interest, or region of interest) on a pen for making on-chip concentration measurements (i.e., secretion rate) of secreted molecules. FRAP is discussed in greater detail below.

Figure 34A:
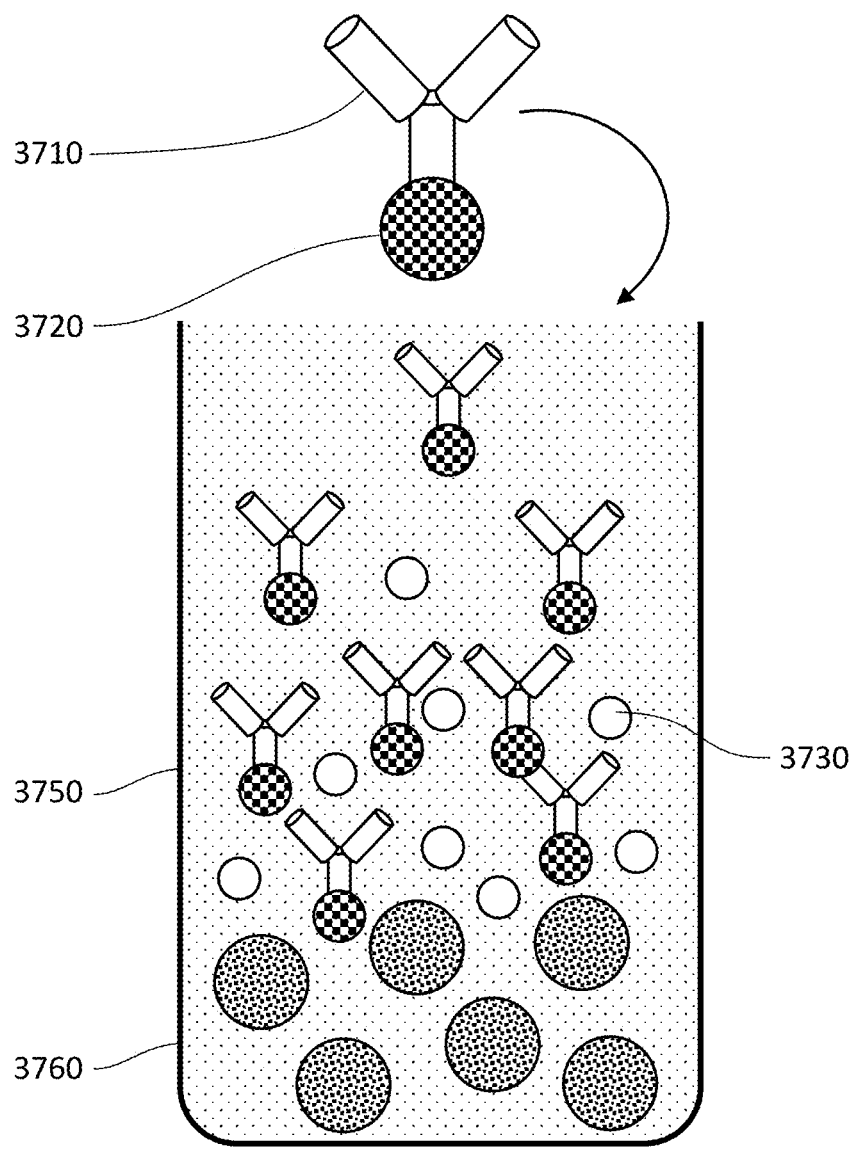
FIGS. 34A-C illustrate examples of cell line development assay for small molecule analytes, in accordance with various embodiments.
Figure 34B:
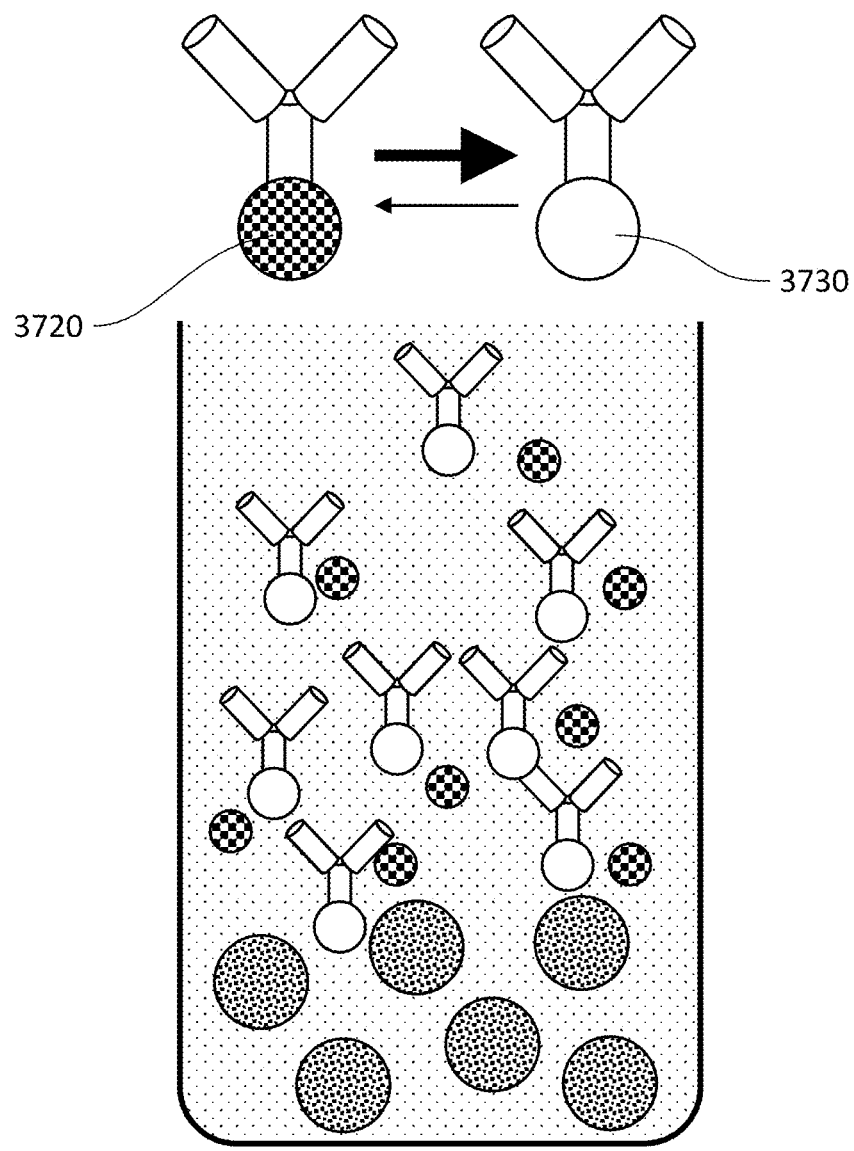
Figure 34C:
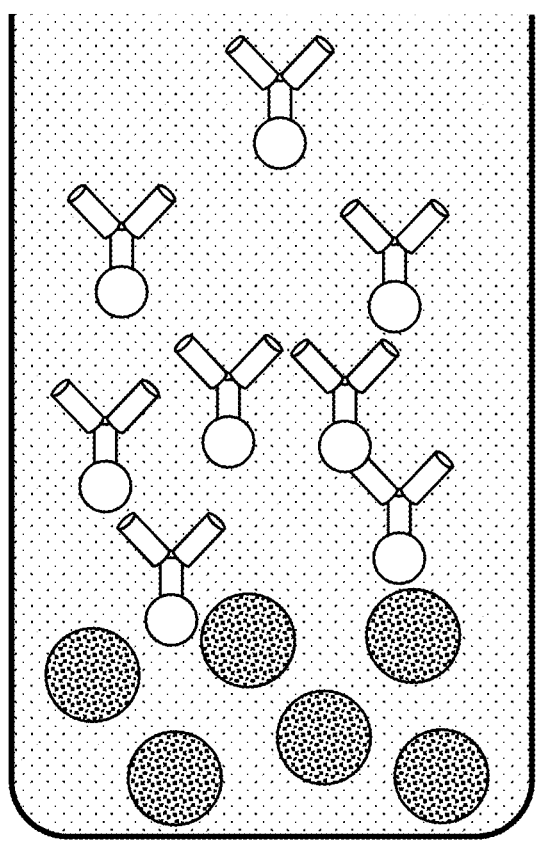

FIGS. 34A-C illustrate an example of this method, in accordance with various embodiments. In FIG. 34A, high-MW anchor protein 3710 (e.g., antibody) with bound fluorescent molecule 3720 (labeled target) is introduced to a pen 3750 containing cells 3760 and secreted unlabeled target 3730. In FIG. 34B, binding kinetics drive the exchange of the labeled targets 3720 with unlabeled targets 3730. Assume, for example, the desire is to find cells producing the highest amount of FcIII peptide. To accomplish this, in view of above, one could add labeled FcIII pre-bound to an anchor off chip. After introduction of this labeled target into pens, over time, an exchange in pens between unlabeled FcIII secreted by cells and labeled FcIII pre-equilibrated onto anchor will occur. Finally, in FIG. 34C, exchange is complete and channels can be flushed to allow unbound fluorescent targets to diffuse out of pen. From there, standard image capture and analysis (as discussed herein) can be used to observe fluorescence levels. However, as opposed to seeking brighter pens as indicative of high secretion levels, since unbound fluorescent targets are removed, the dimmer pens secrete more small molecule target.

Diffusion assay under non-flow conditions in the microfluidic channel. FIGS. 5A through 5C illustrate an assay according to one embodiment of the disclosure. In FIG. 5A, reporter molecules 412, each having a detectable label, are introduced into the microfluidic channel 122 of microfluidic device 500 by flowing a fluid containing a concentration of the reporter molecules 412 into the channel 122. FIG. 5A also shows sequestration pens 524, 526, 528 fluidically connected to the microfluidic channel 122 containing various numbers of cells 502, 504, 506 secreting a biological analyte 410. Each of sequestration pens 524, 526, 528 include a connection region 536 and an isolation region 540 (sequestration pen 524 is the only pen labeled, just for clarity). The connection region 536 and isolation region 540 have properties as described above, and limit the contact of materials introduced into the channel 122 (e.g, within isolation region 540, materials flowing within the channel 122 may enter the isolation region only by diffusion, not by flow directly into the isolation region.) At the time point illustrated in FIG. 5A, the molecules of the secreted analyte 410 are proximal to the cells.

FIG. 5B illustrates the same region of the microfluidic device as in FIG. 5A at a later time point. The reporter molecules 412 can rapidly diffuse within the channel 122 and sequestration pens 524, 526, 528 such that the concentration of the reporter molecules 412 equilibrate between the channel 122 and the interiors of the sequestration pens 524, 526, 528. As illustrated in FIG. 5B, the reporter molecules 412 have reached a steady-state concentration equilibrium such that the concentration of the unbound reporter molecules 412 can be substantially uniform in the sequestration pens 524, 526, 528 and the channel 122. The flow in the channel is stopped when the concentration of reporter molecules 412 is equilibrated into the sequestration pens 524, 526, 528. As the reporter molecules 412 contact the molecules of secreted analyte 410, the reporter molecules 412 can bind to the analyte 410, forming a reporter molecule:analyte complex 414, and providing a localized detectable signal that is related to the quantity of the secreted analyte 410.

FIG. 5C illustrates the same region of the microfluidic device as in FIGS. 5A and 5B at yet a later time point at which the secreted analyte 410 and reporter molecule:analyte complexes 414 are diffusing from the source of the secreted analyte 410 (e.g., cells 502, 504, 506) to the channel 122. There is no flow in the channel 122 at this time point.

As above, the secreted analyte molecules 410 may have a greater molecular weight (and associated effective size in solution) than the reporter molecules 412. Therefore, the reporter molecule:analyte complex 414 can diffuse more slowly than the unbound reporter molecule 412, providing a distinct diffusion profile and associated detectable signal, relative to the uniform signal provided by the unbound reporter molecules 412. Additionally, the biological micro-objects 502, 504, 506 continue to secrete the analyte 410, providing more targets for binding with reporter molecules 412 which are still disposed within the sequestration pens 524,526,528.

The diffusion profiles and/or associated signals may be proportional to the number of biological micro-objects in the pens. Sequestration pen 524 is illustrated as containing 6 biological micro-objects, sequestration pen 526 is illustrated as containing 4 biological micro-objects and t sequestration pen 528 is illustrated as containing 2 biological micro-objects. In some other embodiments, however, the cells 502, 504, 506 in respective sequestration pens 524, 526, 528 may secrete the analyte 410 at about the same rate, and the resulting intensity of detected signal from the reporter molecule:analyte complexes 414 may be proportional to the number of cells 502, 504, 506 present in each sequestration pen. However, secretion of the analyte may depend on the cell cycle state at the assay signal acquisition time. Further, as illustrated in FIG. 5C, while all of the cells 502, 504, 506 are secreting the analyte, different populations of cells (e.g., different clones) may secrete the biological analyte 410 at varying rates. Therefore the amount of analyte 410 produced (and the resulting intensity of the diffusion profile signal detected from the reporter molecule:analyte complex 414) may not be the same, pen to pen, even when normalized for the number of cells 502, 504, 506 present in each pen. One or more assay images may be obtained during this period of time, which may be used to characterize the amount of secreted analyte 410 within the imaged sequestration pens 524, 526, 528. Description of the analysis performed to arrive at relative or absolute quantification of the amount of secreted analyte 410 produced follows below.

Secreted analytes. An analyte secreted by a biological micro-object may be a protein, a saccharide, a nucleic acid, an organic molecule having a molecular weight of less than 3 Kd, a vesicle, a virus, and any combination thereof. A secreted analyte may be a naturally expressed analyte (e.g., natively expressed) or may be a bioengineered analyte (e.g., a product resulting from gene insertion, deletion, modification and the like). A secreted analyte that is a nucleic acid may be a ribonucleic or a deoxynucleic acid, may include natural or unnatural nucleotides. A secreted analyte that is a virus may be a viral particle, a vector or a phage. A secreted analyte that is a saccharide may be a mono-, di- or polysaccharide. Non-limiting examples of saccharides may include glucose, trehalose, mannose, arabinose, fructose, ribose, xanthan or chitosan. A secreted small, organic molecule may include but is not limited to biofuels, oils, polymers, or pharmaceutics such as macrolide antibiotics. A secreted analyte that is a protein can be an antibody or fragment of an antibody. A secreted analyte that is a protein can be a blood protein, such as an albumin, a globulin (e.g., alpha2-macroglobulin, gamma globulin, beta-2 microglobulin, haptoglobulin), a complement protein (e.g., component 3 or 4), transferrin, prothrombin, alpha 1 antitrypsin, and the like; a hormone, such as insulin, glucagon, somatostatin, growth hormone, growth factors (e.g., FGF, HGF, NGF, EGF, PDGF, TGF, Erythropoietin, IGF, TNF), follicle stimulating hormone, luteinizing hormone, leptin, and the like; a fibrous protein, such as a silk or an extracellular matrix protein (e.g., a fibronectin, laminin, collagen, elastin, vitronectin, tenascin, versican, bone sialoprotein); an enzyme, such as a metalloprotease (e.g., matrix metalloproteinase (MMP)) or other type of protease (e.g., serine protease, cysteine protease, threonine protease, aspartic protease, glutamic protease, asparagine peptide lyase), an amylase, a cellulase, a catalase, a pectinase, and the like; a bacterial, yeast, or protozoan protein; a plant protein; o or a viral protein, such as a capsid or envelope protein. A secreted analyte that is a protein can be an antibody, fragment of an antibody, an enzyme (including but not limited to a proteolytic enzyme), an engineered (normally intracellular protein) protein, such as for example, albumin, and/or a structural protein including but not limited to silkworm silk or spider silk). This list is not limiting and any protein that may be engineered to be secreted may be evaluated by the methods. The secreted analyte may be an antibody-drug conjugate. A non-limiting example of a secreted analyte that may have a combination of a protein, a saccharide, a nucleic acid, an organic molecule having a molecular weight of less than 3 Kd, and/or a virus, can include a proteoglycan or glycoprotein.

Reporter molecules and their characteristics. A reporter molecule may include a binding component designed to bind the secreted analyte and also may include a detectable label. The binding component may be any suitable binding partner configured to bind the secreted analyte. The binding component may be a protein, a peptide, a nucleic acid or small organic molecule having a molecular weight less than 3 Kd. For example, the binding component can be a nucleic acid sequence that specifically binds another nucleic acid sequence or a peptide that specifically binds a protein (e.g. an epitope that recognizes a specific antibody). In some embodiments, the binding component can non-specifically bind a family of secreted analytes of a biological micro-object. For example, the binding component can be a peptide that specifically binds to an IgG domain or a nucleic acid that binds to a domain present in a family of nucleic acid sequences. In some embodiments, the reporter molecule may be multi-valent, comprising more than one binding component to bind more than one copy of the secreted analyte or to more than one member of a family of secreted analytes. For ease of discussion, the term secreted analyte as used herein can refer to either a specific secreted analyte molecule or a family of secreted analytes. The stoichiometry of the RMSA complex can therefore vary. For example, a reporter molecule binding one copy of the secreted analyte may have a RMSA complex with a 1:1 stoichiometry. Alternatively, the RMSA complex may have a 2:1, 3:1, 4:1, 2:2, 4:2, or other stoichiometry of the reporter molecule: secreted analyte. The reporter molecule may have any suitable molecular weight, with the provision that the apparent "size", as defined by diffusion characteristics of the reporter molecule:analyte complex which depend upon molecular weight, is sufficiently "larger" than the reporter molecule itself to observe differential diffusion between unbound reporter molecules and the RMSA complexes. The reporter molecule may have a molecular weight that is about 10%, 20%, 30%, 40%, 50%, 60%, 70%, 80%, 90%, or the same as the molecular weight of the secreted analyte. In some embodiments, the molecular weight of the reporter molecule is less than about 50%, 40%, 30%, 20%, 10% of the molecular weight of the secreted analyte. The molecular weight of the RMSA complex may be at least 2×, 4×, 10×, 20×, 30×, 40×, 50× or any number therebetween, greater than the molecular weight of the reporter molecule. The molecular weight of the RMSA complex may be 2-fold, 4-fold or 50-fold greater than the molecular weight of the unbound reporter molecule.

Reporter molecules for one class of secreted analytes: antibodies. Reporter molecules suitable for binding to antibodies include proteins, peptides and aptamers configured to bind regions of an IgG. A non-limiting list of binding components suitable for use within a reporter molecule to detect an antibody is shown in Table 1.

TABLE 1

Compounds as binding components of a reporter molecule to detect antibodies.

| CPD | Affinity for IgG | Molecular Weight (MW) | Identification |
|---|---|---|---|
| 1 | nanomolar | 42 kDa | Protein A-AF594, Pierce ™ Recombinant Protein A (ThermoFisher Cat. # 77674) |
| 2 | nanomolar | 65 kDa | Protein G- AF594, Pierce ™ Recombinant Protein G (ThermoFisher Cat. # 21193) |
| 3 | NA (Fc) | Approx. 2.4 kDa | SEQ. ID NO. 9 |
| 4 | 100 nM (Fc) | Approx. 2.4 kDa | SEQ. ID NO. 10 |
| 5 | 75 nm (Fc of hIgG) | Approx .8 kDa | Aptamer-AF594, Apta-IndexTM (Apt. 8, ID#44, Aptagen, LC.) |
| 6 | 8.6 nm (Fc) | Approx. 12 kDa | Aptamer IgG Fc C02 #369 (Base Pair Technologies ATW0018 |
| 7 | NA, (Fc) | ~2 kDa to about 4.5 kDa | SEQ. ID. NO. 1 |
| 8 | NA, (Fc) | ~2 kDa to about 4.5 kDa | SEQ. ID. NO. 2 |
| 9 | NA, (Fc) | ~2 kDa to about 4.5 kDa | SEQ. ID. NO. 3 |
| 10 | NA, (Fc) | 2 kDa to about 4.5 kDa | SEQ. ID. NO. 4 |
| 11 | NA, (Fc) | ~2 kDa to about 2.4 kDa | SEQ. ID. NO. 5 |
| 12 | NA, (Fc) | ~2 kDa to about 2.4 kDa | SEQ. ID. NO. 6 |
| 13 | NA, (Fc) | ~2 kDa to about 2.4 kDa | SEQ. ID. NO. 7 |
| 14 | NA, (Fc) | ~2.4 kDa | SEQ. ID. NO. 8 |

Any of CPDs 1-14 can be used in the assays described herein. Some of the above listed CPDs are small peptides which are known to bind to the Fc domain of IgG (For CPD 4 and 7-14, see DeLano W L, et al. (2000), Science 287: 1279-1283, and U.S. Pat. No. 7,608,681B2, the disclosure of each of which is incorporated herein by reference in its entirety).

CPD 3 has a structure of Asp Ser Ala Trp His Leu Gly Glu Leu Val Trp Cys Thr (SEQ ID NO: 9).

CPD4 has a structure of Asp Cys Ala Trp His Leu Gly Glu Leu Val Trp Cys Thr (SEQ ID NO: 10).

CPD 7 has a structure of $Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-Leu-Val-Trp-Cys-$Xaa_{16}$-$Xaa_{17}$-$Xaa_{18}$-$Xaa_{19}$-$Xaa_{20}$ (SEQ ID NO: 1), where: $Xaa_1$ is any amino acid or absent; $Xaa_2$ is any amino acid or absent; $Xaa_3$ is any amino acid or absent; $Xaa_4$ is any amino acid or absent; $Xaa_5$ is Cys or Ser; $Xaa_6$ is any amino acid; $Xaa_7$ is any amino acid; $Xaa_8$ is any amino acid; $Xaa_9$ is any amino acid; $Xaa_{10}$ is any amino acid; $Xaa_{11}$ is any amino acid; $Xaa_{16}$ is any amino acid or absent; $Xaa_{17}$ is any amino acid or absent; $Xaa_{18}$ is any amino acid or absent; $Xaa_{19}$ is any amino acid or absent; and $Xaa_{20}$ is any amino acid or absent.

CPD 8 has a structure of $Xaa_1$-$Xaa_2$-$Xaa_3$-$Xaa_4$-$Xaa_5$-$Xaa_6$-$Xaa_7$-$Xaa_8$-$Xaa_9$-Gly-Glu-Leu-Val-Trp-Cys-$Xaa_{16}$-$Xaa_{17}$-$Xaa_{18}$-$Xaa_{19}$-$Xaa_{20}$ (SEQ ID NO: 2), where: $Xaa_1$ is any amino acid or absent; $Xaa_2$ is any amino acid or absent; $Xaa_3$ is any amino acid or absent; $Xaa_4$ is any amino acid or absent; $Xaa_5$ is Cys or Ser; $Xaa_6$ is any amino acid; $Xaa_7$ is any amino acid; $Xaa_8$ is any amino acid; $Xaa_9$ is any amino acid; $Xaa_{16}$ is any amino acid or absent; $Xaa_{17}$ is any amino acid or absent; $Xaa_{18}$ is any amino acid or absent; $Xaa_{19}$ is any amino acid or absent; and $Xaa_{20}$ is any amino acid or absent.

CPD 9 has a structure of $Xaa_1$-$Xaa_2$-$Xaa_3$-$Xaa_4$-$Xaa_5$-$Xaa_6$-$Xaa_7$-$Xaa_8$-$Xaa_9$-Gly-Glu-Leu-Val-Trp-Cys-$Xaa_{16}$-$Xaa_{17}$-$Xaa_{18}$-$Xaa_{19}$-$Xaa_{20}$ (SEQ ID NO: 3), where: $Xaa_1$ is any amino acid or absent; Xaa$_2$ is any amino acid or absent; Xaa$_3$ is any amino acid or absent; Xaa$_4$ is any amino acid or absent; Xaa$_5$ is Cys or Ser; Xaa$_6$ is Ala, Ser, or Thr; Xaa$_7$ is Trp or Tyr; Xaa$_8$ is His or Trp; Xaa$_9$ is Leu or Met; Xaa$_{16}$ is any amino acid or absent; Xaa$_{17}$ is any amino acid or absent; Xaa$_{18}$ is any amino acid or absent; Xaa$_{19}$ is any amino acid or absent; and Xaa$_{20}$ is any amino acid or absent.

CPD 10 has a structure of Xaa$_1$-Xaa$_2$-Xaa$_3$-Xaa$_4$-Xaa$_5$-Xaa$_6$-Xaa$_7$-Xaa$_8$-Xaa$_9$-Gly-Glu-Leu-Val-Trp-Cys-Xaa$_{16}$-Xaa$_{17}$-Xaa$_{18}$-Xaa$_{19}$-Xaa$_{20}$ (SEQ ID NO: 4), where: Xaa$_1$ is any amino acid or absent; Xaa$_2$ is any amino acid or absent; Xaa$_3$ is any amino acid or absent; Xaa$_4$ is Ser, Arg, or Asp; Xaa$_5$ is Cys or Ser; Xaa$_6$ is Ala, Ser, or Thr; Xaa$_7$ is Trp or Tyr; Xaa$_8$ is His or Trp; Xaa$_9$ is Leu or Met; Xaa$_{16}$ is Glu, Ser, Thr, or Val; Xaa$_{17}$ is any amino acid or absent; Xaa$_{18}$ is any amino acid or absent; Xaa$_{19}$ is any amino acid or absent; and Xaa$_{20}$ is any amino acid or absent.

CPD 11 has a structure of Xaa$_1$-Xaa$_2$-Xaa$_3$-Xaa$_4$-Xaa$_5$-Xaa$_6$-Xaa$_7$-Xaa$_8$-Leu-Val-Trp-Cys-Xaa$_{13}$ (SEQ ID NO: 5), where: Xaa$_1$ is any amino acid or absent; Xaa$_2$ is Cys or Ser; Xaa$_3$ is any amino acid; Xaa$_4$ is any amino acid; Xaa$_5$ is any amino acid; Xaa$_6$ is any amino acid; Xaa$_7$ is any amino acid; Xaa$_8$ is any amino acid; and Xaa$_{13}$ is any amino acid or absent.

CPD 12 has a structure of Xaa$_1$-Xaa$_2$-Xaa$_3$-Xaa$_4$-Xaa$_5$-Xaa$_6$-Gly-Glu-Leu-Val-Trp-Cys-Xaa$_{13}$ (SEQ ID NO: 6), where: Xaa$_1$ is any amino acid or absent; Xaa$_2$ is Cys or Ser; Xaa$_3$ is any amino acid; Xaa$_4$ is any amino acid; Xaa$_5$ is any amino acid; Xaa$_6$ is any amino acid; and Xaa$_{13}$ is any amino acid or absent.

CPD 13 has a structure of Xaa$_1$-Xaa$_2$-Xaa$_3$-Xaa$_4$-Xaa$_5$-Xaa$_6$-Gly-Glu-Leu-Val-Trp-Cys-Xaa$_{13}$ (SEQ ID NO: 7), where: Xaa$_1$ is any amino acid or absent; Xaa$_2$ is Cys or Ser; Xaa$_3$ is Ala, Ser, or Thr; Xaa$_4$ is Trp or Tyr; Xaa$_5$ is His or Trp; Xaa$_6$ is Leu or Met; and Xaa$_{13}$ is any amino acid or absent.

CPD 14 has a structure of Xaa$_1$-Xaa$_2$-Xaa$_3$-Xaa$_4$-Xaa$_5$-Xaa$_6$-Gly-Glu-Leu-Val-Trp-Cys-Xaa$_{13}$ (SEQ ID NO: 8), where: Xaa$_1$ is Ser, Arg, or Asp; Xaa$_2$ is Cys or Ser; Xaa$_3$ is Ala, Ser, or Thr; Xaa$_4$ is Trp or Tyr; Xaa$_5$ is His or Trp; Xaa$_6$ is Leu or Met; and Xaa$_{13}$ is Glu, Ser, Thr, or Val.

The binding component is not limited to a material having a high affinity (e.g., nanomolar as is known for CPD 1 and CPD 2 of Table 1) for IgG. In some embodiments, binding components having affinities greater than about 100 millimolar or 1 micromolar may be successfully used in this diffusion based assay to detect antibodies.

For other types of secreted analytes, different types of binding components of reporter molecules may be used. For example, an irreversible protease inhibitor may be used to detect a proteolytic enzyme, such as a fluoromethyl ketone inhibitor for serine or cysteine proteases. Aptamers to engineered analytes such as saccharides or macrolide antibiotics may be used. Antibodies or fragments thereof may be used to detect albumins, structural proteins, or macrolide antibiotics. Any suitable binding component to a secreted analyte may be used as is known in the art.

Reporter molecule: purification tags. Current cell line development assays can depend on the presence of an Fc region common to antibodies. However, many therapeutic proteins and proteins produced for synthetic biology applications lack this moiety and are therefore may be incompatible with certain cell line development assays. Many of these non-antibody proteins either already include or could be designed to include genetically encoded residues that introduce short amino acids "tags" that are used for purification. These designer tags can also be referred to as exogenous tags. An exogenous tag is a non-naturally occurring feature of the secreted analyte. For example, a gene/transgene encoding the secreted analyte can be genetically engineered to include a sequence that encodes the exogenous tag.

In accordance with various embodiments, current on-chip titer assays could be modified to use fluorescently labeled small molecules that are specific to purification tags (i.e., short amino acids "tags" that are used for purification). This modification allows for solutions to large classes of proteins that are currently inaccessible to many cell line development assays.

Figure 33:
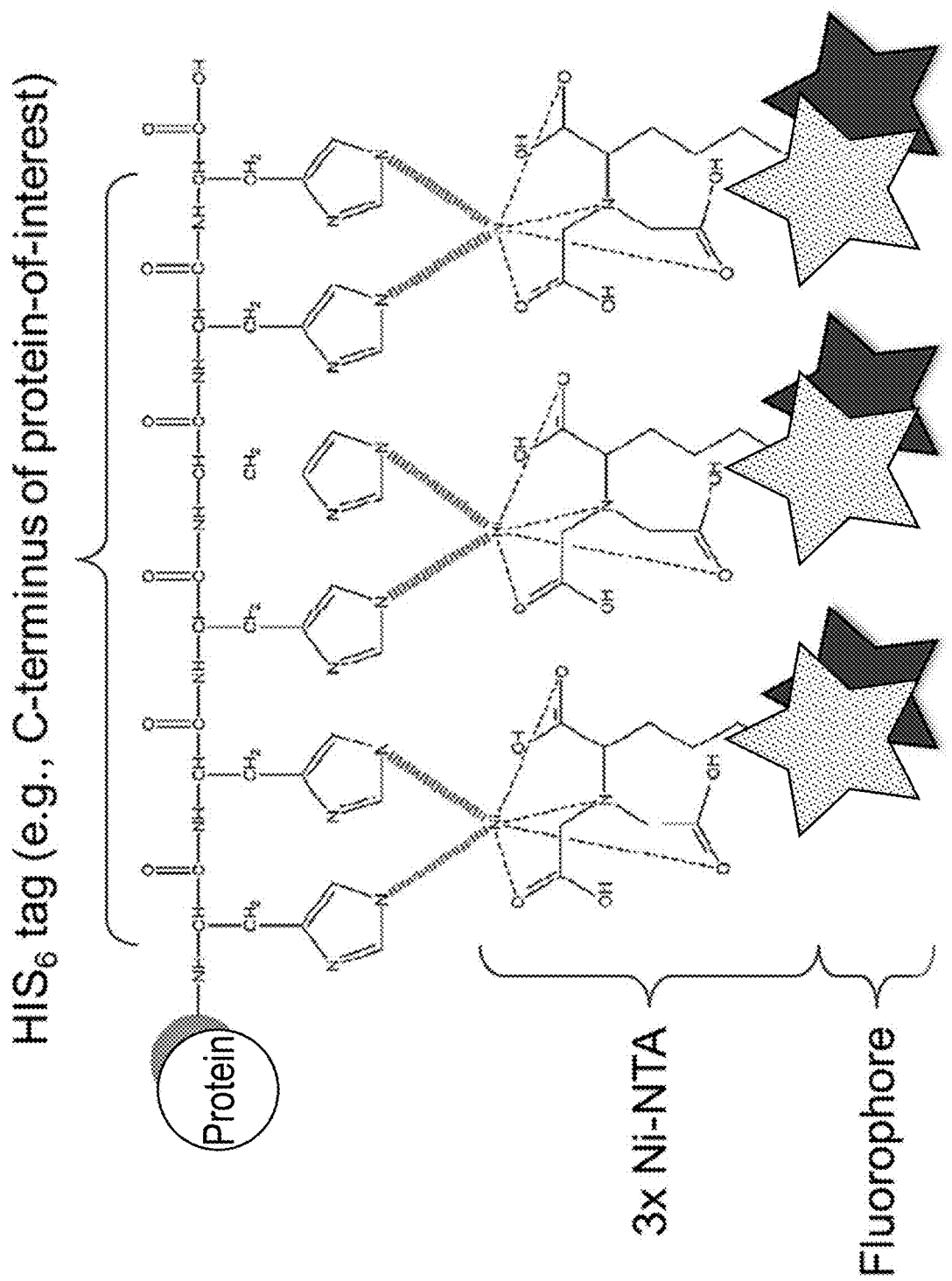
FIG. 33 is a visual representation of a $HIS_6$ tag (SEQ ID NO: 13), in accordance with various embodiments.

In one example, a hexahistidine (HIS$_6$) tag (SEQ ID NO: 13) is encoded into the N- or C-terminus of a protein of interest; this tag is subsequently used to purify the HIS$_6$-labeled protein ("HIS$_6$" disclosed as SEQ ID NO: 13) using a Ni-NTA (Nα,Nα-bis(carboxymethyl)-L-lysine, Nickel(II) complex) column, which specifically binds hexahistidine (SEQ ID NO: 13) with high affinity. This chemical interaction can be leveraged to label the HIS6 tag (SEQ ID NO: 13) with a fluorescently labeled species, such as Ni-NTA-Atto conjugates from, for example, Sigma. As is well known in the industry, Ni-NTA-Atto conjugates can provide specific and highly sensitive detection of HIS-tagged fusion proteins. The Ni-NTA-Atto complex, conjugated to Atto dye, is specific for polyhistidine tags and can perform with minimal cross-reactivity. See FIG. 33, which illustrates the above example. Specifically, each Ni-NTA moiety binds to a pair of histidine side chains and each Ni-NTA can be labeled with a fluorophore. Moreover, two or three Ni-NTA moieties together can be cross-linked together to increase binding affinity.

Use of these tags in methods for assessing a level of secretion of an analyte by a biological micro-object, or a population of biological micro-objects generated therefrom, will be discussed in detail below in the Methods section.

Reporter complex for low molecular weight secretions. As discussed above, measuring the production of small molecules (low molecular weight secretions) can be accomplished, for example, by inverting the cell line development assay in accordance with various embodiments, wherein the brighter fluorescing pens will indicate not the highest producing cell lines, but rather the weaker producing lines. To provide for this, a molecule (e.g., large molecular weight protein or protein complex, referred to as an "anchor") that is known to bind to small molecule targets, can first be bound off-chip with a fluorescent version of the target-of-interest. This fluorescent reporter complex (anchor+fluorescent target) can be equilibrated throughout the chip, including within the pens containing cells that could be secreting non-fluorescence versions of the target. In the presence of these unlabeled targets, binding kinetics will drive the exchange of the labeled targets with unlabeled targets at much higher concentration within the pens. After flushing the channels clear for some time, the fluorescent targets not bound by an anchor will diffuse rapidly from the pen. As a result, when reading fluorescence levels subsequent to this flush, the dimmer observed pens will equate to those secreting more small molecular weight target.

Detectable label. The reporter molecule may also include a visible, luminescent, phosphorescent, or fluorescent detectable label. In some embodiments, the detectable label may be a fluorescent label. Any suitable fluorescent label may be used, including but not limited to fluorescein, rhodamine, cyanine, phenanthrene or any other class of fluorescent dye label. Some examples of useful fluorescent dye labels include fluorescein (available as a thioisocyanate active species for labelling of the binding component of the reporter molecule) Alexa Fluor® 594 ((AF594, ThermoFisher Scientific, Cat. No. A20004 (NHS ester)) MW 819.8, Ex/Em590/617 nm) or HiLyte Fluor™ 555 (AnaSpec Inc., Cat. #AS-81250) MW 869, Ex/Em550/566 nm (Cy3 filter). In some embodiments, the reporter molecule, such as an aptamer or capture oligonucleotide, may include a FRET labeled oligonucleotide, which may include but is not limited to a molecular beacon, dual hybridization probe, Scorpion®, or Eclipse® probe. A FRET labeled oligonucleotide probe or probe pair may include fluorescent labels that do not fluoresce until a hybridization event takes place. In some embodiments, the detectable label is covalently attached directly or indirectly to the binding component of the reporter molecule. In some other embodiments, a capture oligonucleotide may be a binding component of a reporter molecule and either an intrinsic or extrinsic fluorescent dye may be the detectable label, such that the detectable label of the reporter molecule may not be detectable until the capture oligonucleotide binds the analyte, for example, an intercalating dye. In some embodiments, a detectable label of a reporter molecule may not be detectable until after the RMSA complex has formed, as the detectable signal is shifted to a new wavelength not present prior to binding. In some embodiments, such as an intercalating dye covalently attached to the binding component of the reporter molecule. In other embodiments, the detectable label may be an isotope.

In yet other embodiments, the detectable label and the binding component is a single moiety, for example a protein or nucleic acid that provides a detectable signal (e.g. a self-detectable protein such as a green fluorescent protein (GFP), or a ribonucleic acid aptamer such as "Spinach", which is an RNA equivalent to GFP. Spinach incorporates 3,5-difluoro-4-hydroxybenzylidene imidazolinone (DFHBI) as the fluorescent detectable label.

Diffusion modelling. The methods described herein utilize models and observations related to differential diffusion of secreted analytes from the isolation region of a sequestration pen to the flow region (e.g., microfluidic channel). A number of software programs may be used in modelling the behaviors of secreted analytes of a biological micro-object including, but not limited to COMSOL®, MATLAB® and/or various numerical modeling and computer-assisted design tools.

Figure 6:
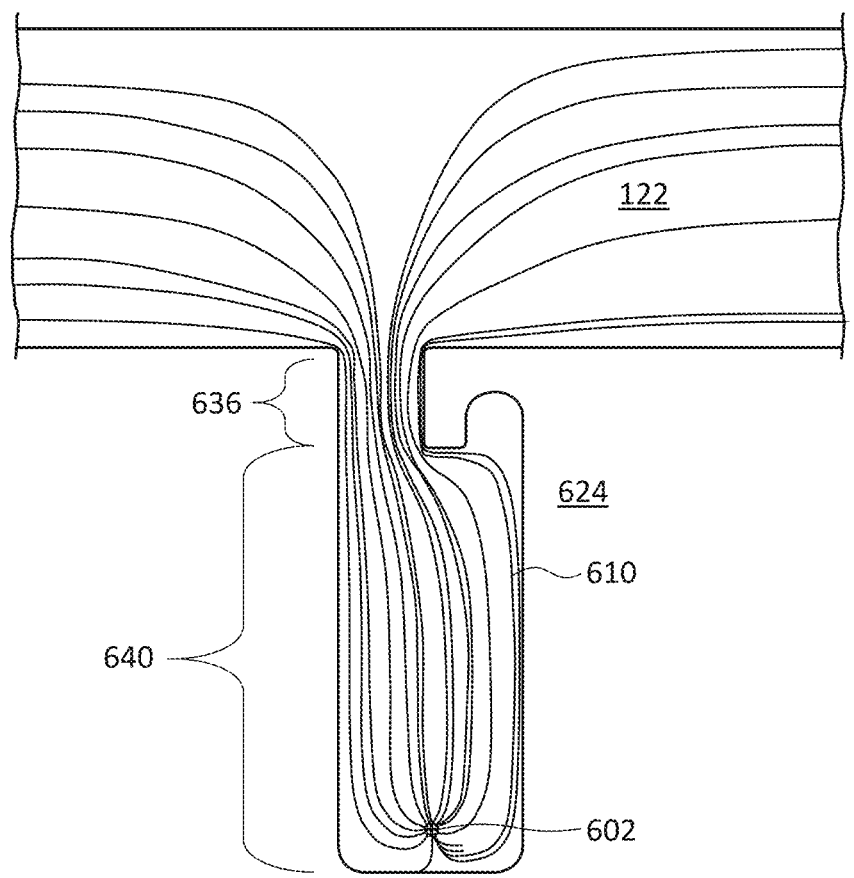
FIG. 6 is a schematic illustration of diffusion characteristics within a chamber of a microfluidic device according to some embodiments of the disclosure.

FIG. 6 shows a model of one type of sequestration pen having one biological cell (602) placed at the base of the sequestration pen 624, within the isolation region 640, at a point distal to the opening of the sequestration pen 624 to the channel 122. Lines of diffusion 610 show the trajectory of diffusion of a secreted analyte of the cell 602 from the isolation region 640 through the connection region 636 to the channel 122. It can be seen that as diffusing materials passage through the connection region the lines of diffusion concentrated and flow linearly to the channel 122. The rate of diffusion is defined by the secreted analyte's coefficient of diffusion and can be modeled as follows.

The diffusion coefficient, D for a specific secreted analyte is defined as:

$$D = (1/f)kT \quad \text{(Equation 1)}$$

where f is a frictional coefficient, k is the Boltzman constant, and T is the absolute temperature. The frictional coefficient f is dependent upon the viscosity ($\eta$) of the solvent in which the secreted analyte is diffusing and on the size and shape of the secreted analyte. A secreted analyte having a spherical sphere has a minimalized frictional coefficient, but a nonsymmetrical shape such as that of an antibody or other protein with defined structural constraints will result in larger f. Additionally, if the secreted analyte has interactions with the solvent such as hydrogen bonding or waters of hydration associated with the secreted analyte, the frictional coefficient will also be increased. Some genericized diffusion coefficients are shown in Table 2.

TABLE 2

Exemplary diffusion coefficients.

| Generic material | Diffusion Coefficient |
| --- | --- |
| Small molecule (<1 kDa) in water | $1\text{-}1.5 \times 10^{-5}$ cm$^2$ s$^{-1}$ |
| Small protein (<20 kDa) | $10^{-6}$ cm$^2$ s$^{-1}$ |

Diffusion of the secreted analyte can be represented by the following equation:

$$<x^2> = q_i Dt \quad \text{(Equation 2)}$$

where $<x^2>$ is the mean squared displacement, and x is the mean distance from a selected starting point of travel over time t. The value of $q_i$ depends on whether diffusion is being evaluated in 1, 2, or 3 dimensions.

Figure 7B:
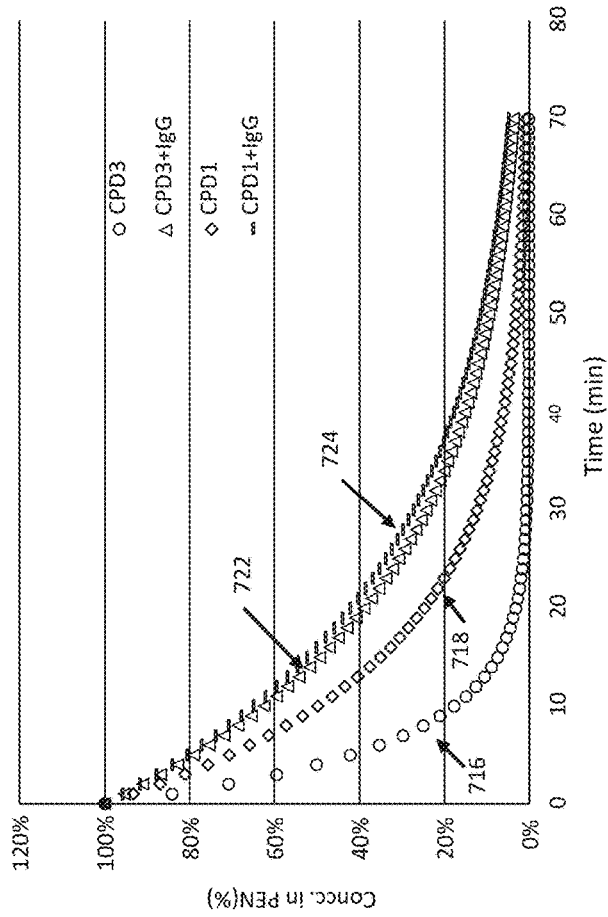
FIGS. 7A-7B are graphical representations of calculated diffusion rates of molecules according to some embodiments of the disclosure.
Figure 7A:
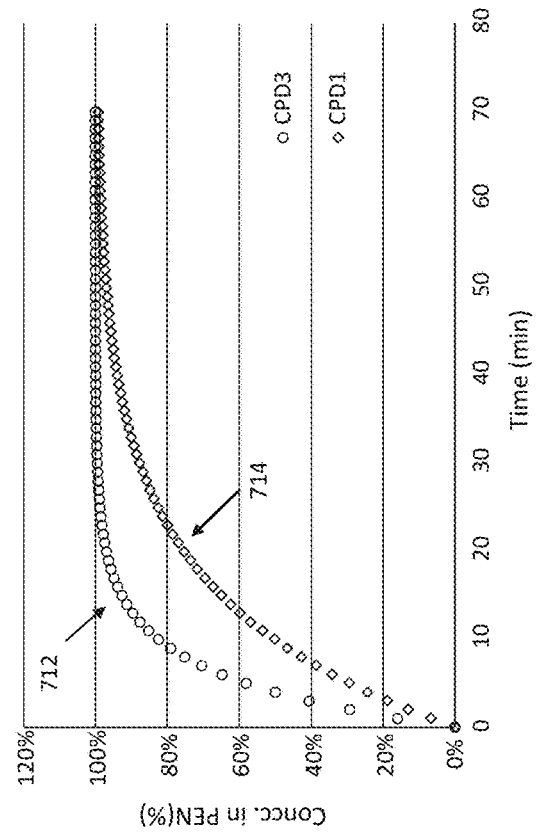

With these equations, the time for a reporter molecule to diffuse in and out of a sequestration pen of defined configuration and the time for the RMSA complex can be modelled, and is shown in FIGS. 7A and 7B for an antibody secreted analyte, having a molecular weight in the range of about 150 kDa. In FIG. 7B, curve 712 models the behavior of a small peptide like CPD 3, molecular weight of about 2.5 kDa, where the small peptide is calculated to be capable of diffusing into and equilibrating within a sequestration pen configured like the sequestration pen 424, 524, 624 and the like (FIGS. 4A-C, 5 and 6 respectively) from the channel in within 25-30 min. In contrast, curve 714 models the behavior of the much larger CPD 1, having a molecular weight of about 45 kDa. This larger molecule presents more opportunities to interact with the solvent, and full equilibration is not reached somewhere between 45-50 min.

In FIG. 7B, the behavior of four different species is shown for diffusion out of a sequestration pen configured like that of 424, 624. In this graph, curve 716 shows the calculated rate of diffusion out of a sequestration pen configured like that of sequestration pen 424, 524, 624, and the like, for the small peptide CPD 3. Small peptide CPD 3 is substantially eliminated from the sequestration pen by about 25 min. In contrast, when CPD 3 is bound to the secreted analyte IgG (MS 150 kDa), curve 722 (triangular shape) shows the calculated diffusion behavior for the RMSA complex containing CPD 3, where a small amount of RMSA complex remains after 60 min. Curve 718 (diamond shape) shows the calculated diffusion behavior for CPD 1 (protein A, a 45 kDa protein), which accordingly requires over 50 min to diffuse out substantially completely. When this protein complexes with the secreted antibody (MW 150 kDa) curve 724 (dashed segment) shows a similarly slow rate of diffusion to that of CPD 3: IgG complex, and still shows complex remaining after 60 min.

Figures 8A, 8B:
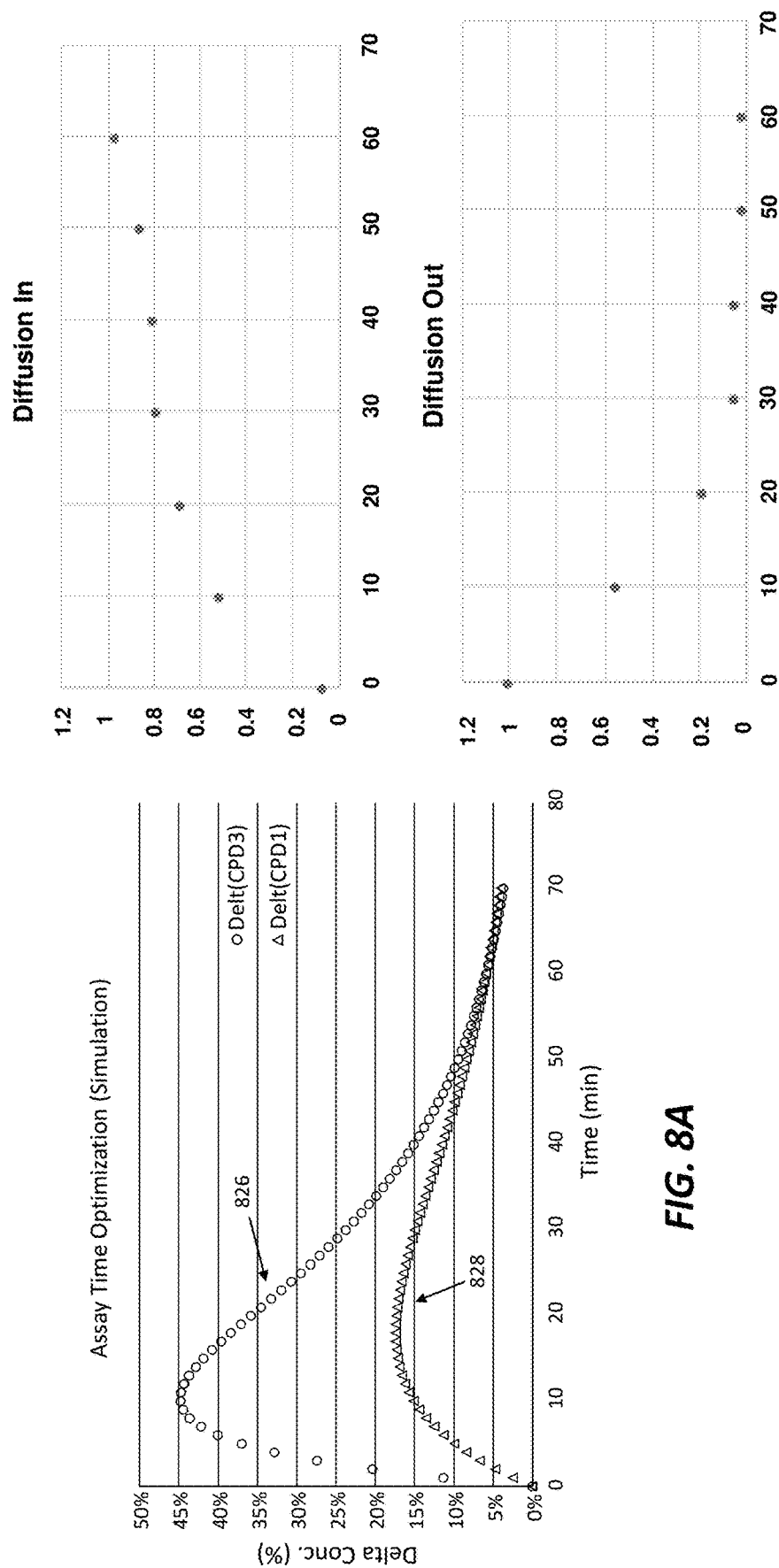
FIGS. 8A-8B are graphical representations of calculated and experimentally confirmed diffusion rates of molecules according to some embodiments of the disclosure.

FIG. 8A shows the calculation of the difference between reporter molecule and RMSA complexes for each of the two different binding components of the reporter molecule. Curve 826 shows the assay time optimization for the maximal difference in concentration within the sequestration pen for the CPD 3: CPD 3/IgG pairing, in order to observe the maximum signal arising from the RMSA complex and the minimal signal due to unbound reporter molecule, which appears to be at about 15 minutes of restored medium flow in the microfluidic channel, which exports any diffused material out of the microfluidic device. Curve 826 shows the difference curve for CPD 1, showing the difference in concentration between the unbound CDP-1 and RMSA complex containing CPD 1 within the sequestration pen, and showing that the maximized difference is out at a later timepoint, sometime after 25 minutes or longer. FIG. 8B shows the experimental time for diffusion in (upper graph) and diffusion out (lower graph) for unbound CPD 1, showing reasonable correlation with the calculated values. These sets of modelling and executed experiments shows that it is possible to find optimized points in time for observation of a detectable signal from substantially the reporter molecule: secreted analyte complex in order to assess the levels of analyte secretion within a specific sequestration pen.

Selection of a region along an axis of diffusion. FIGS. 9A-B and 10A-B show modelling experiments used to determine a region from which to extract quantitative measurements (either relative or absolute) from assay images. In FIGS. 9A-B, modelling of diffusion flow and resultant fluorescent signal intensity from the RMSA complex was performed to consider the effect of location of biological cell 902, 904, 906 within sequestration pen 924 of microfluidic device 900, which is similar to sequestration pen 424, 524, 624. The effect was modeled using a location for cell 902 at about 25 microns from the base of the sequestration pen (0 microns), which is distal to the opening of the sequestration pen 924 to the channel 122; cell 904 was modeled at a distance about 100 microns from the base of the sequestration pen 924; and cell 906 was modeled at a distance about 180 microns from the base of the sequestration pen 924 (see horizontal axis of FIG. 9A and FIG. 9B). Each cell is modeled to lie along a center axis of diffusion trajectory towards the opening of the sequestration pen, illustrated by line 952, for modelling simplicity. Each of these positions lie within the isolation region 940 of the sequestration pen, and well away from the connection region 936 of the sequestration pen, therefore insuring that signal intensity detected from cells 902, 904, 906 within the isolation region 940 are not affected by flow effects from flow 242 in the channel 122. The y axis of FIG. 9A represents the normalized concentration of reporter molecule (or equivalently RMSA complex, as this experiment relies only upon fluorescence intensities detected.) As shown in FIG. 9A, the intensity of the fluorescent signal (modelling includes the constraint that 902, 904, 906 are all producing secreted analyte at the same rate) is highest for cell 902, as the fluorescently labeled complex is diffusing in a more monodirectional manner than that of 904, 906, due to its location near the base of the sequestration pen 924. Cells 904, 906 have more capacity to have labeled RMSA complexes diffusing in all directions. What is determined by this model is that a region can be identified, where the signal intensity is most sensitive to changes in fluorescent signal intensity due to changes in labeled species' concentrations (e.g., RMSA complex), and least sensitive to the exact location of cell 902, 904, 906, which is region 944, which lies along the axis of diffusion between the sequestration pen 924 and the channel 122, as indicated both in FIGS. 9A and 9B. Cell position insensitive region 944 is at least a portion of an area of interest (AOI) used to assess the relative or absolute amount of a secreted analyte of a biological micro-object within a sequestration pen 924. In some embodiments, an AOI may include additional portions of the sequestration pen 924 and/or the channel 122.

Sequestration pen optimized for large populations of cells. FIGS. 10A and 10B illustrates a similarly constructed modelling experiment as shown in FIGS. 9A and B for a differently configured sequestration pen 1024. The effect of location of biological cell 1002, 1004, 1006 within sequestration pen 1024 (which is similar to sequestration pen 224, 226, 228) of microfluidic device 1000 is shown. The effect was modeled using a location for cell 1002 at about 25 microns from the base of the sequestration pen (0 microns), which is distal to the opening of the sequestration pen 1024 to the channel 122; cell 1004 was modeled at a distance about 100 microns from the base of the sequestration pen 1024; and cell 1006 was modeled at a distance about 180 microns from the base of the sequestration pen 1024 (see horizontal axis of FIG. 10A and FIG. 10B). Each cell is modeled to lie along a center axis of diffusion trajectory towards the opening of the sequestration pen, illustrated by line 1052, for modelling simplicity. Each of these positions lie within the isolation region 1040 of the sequestration pen, and well away from the connection region 1036 of the sequestration pen, therefore insuring that signal intensity detected from cells 1002, 1004, 1006 within the isolation region 1040 are not affected by flow effects from flow 242 in the channel 122. The y axis of FIG. 10A represents the normalized concentration of reporter molecule (or equivalently RMSA complex, as this experiment relies only upon fluorescence intensities detected), and the discussion of the concentrations shown are as above for FIG. 9A. What is determined by this model is that a region can be identified, where the signal intensity is most sensitive to changes in fluorescent signal intensity due to changes in labeled species' concentrations (e.g., RMSA complex), and least sensitive to the exact location of cell 1002, 1004, 1006, which is region 1044, which lies along the axis of diffusion between the sequestration pen 1024 and the channel 122, as indicated both in FIGS. 10A and 10B. Cell position insensitive region 1044 is at least a portion of an AOI used to assess the relative or absolute amount of a secreted analyte of a biological micro-object within a sequestration pen 1024. In some embodiments, an AOI may include additional portions of the sequestration pen 1024 and/or the channel 122 which are located along the axis of diffusion between the sequestration pen 1024 and the channel.

Figure 11A:
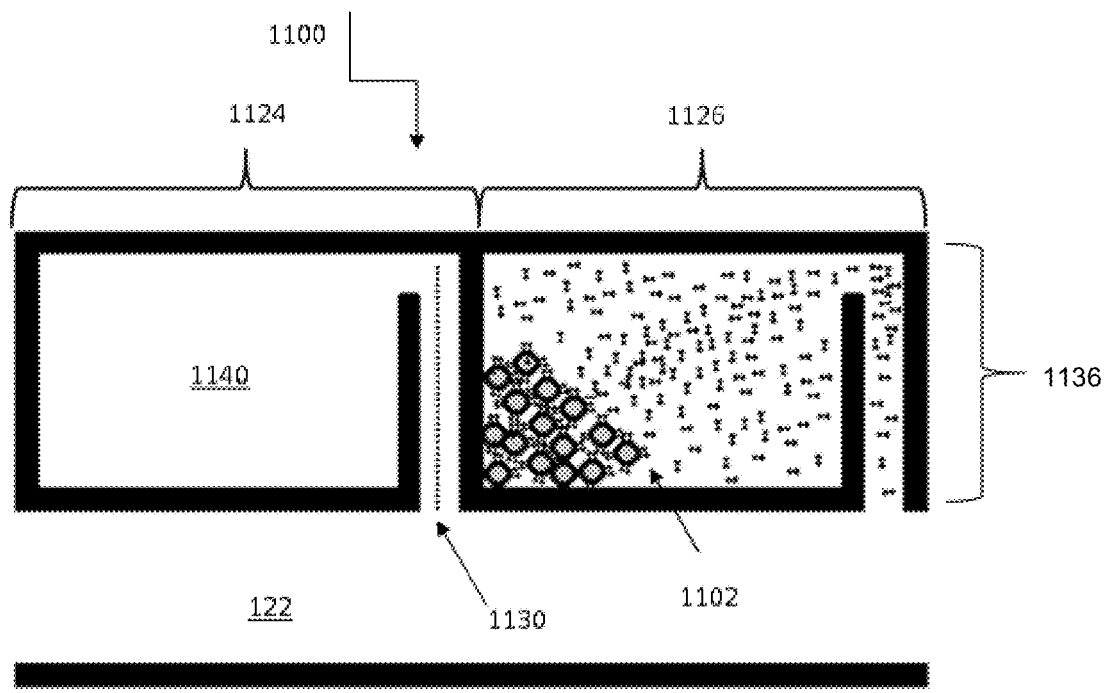
FIGS. 11A-11B are graphical representation of diffusion characteristics within a chamber of a microfluidic device according to yet other embodiments of the disclosure.

In some embodiments, the geometry of a sequestration pen may be altered to provide an optimal diffusion profile of a secreted analyte. FIG. 11A illustrates a section of a microfluidic device 1100 comprising a channel 122 and sequestration pens 1124, 1126 designed to provide an optimized diffusion profile. Specifically, the sequestration pens 1124, 1126 have isolation regions which can accommodate a large number of biological micro-objects 1102, which may be useful in providing a larger signal intensity for use in assessing the quantity (relative or absolute) of secreted analytes of the cells 1102.

Figure 11B:
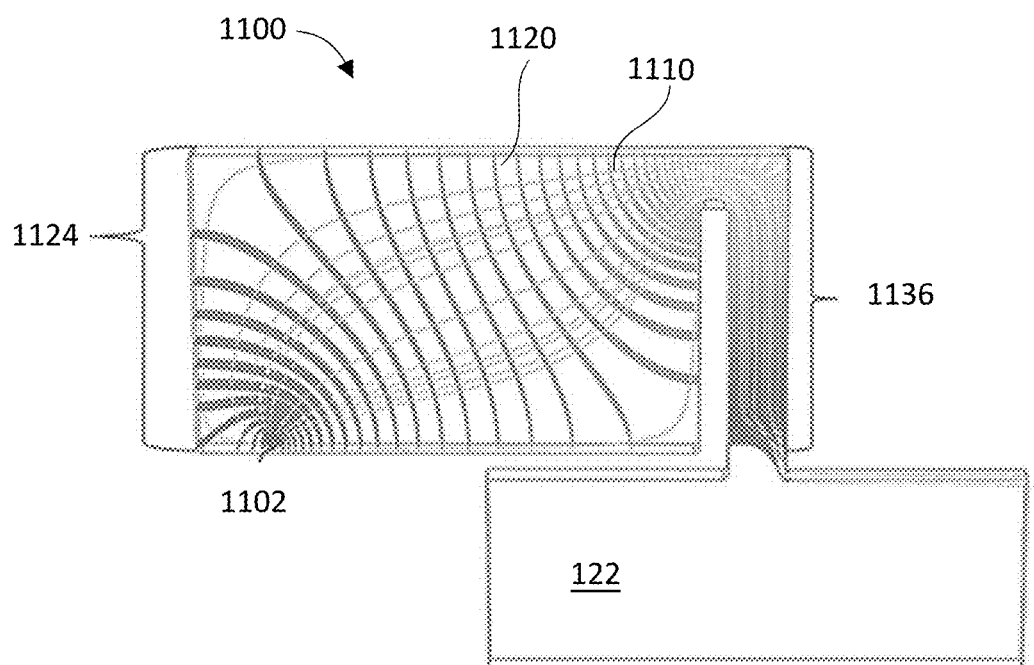

In some embodiments, the isolation region 1140 of sequestration pen 1124 may accommodate a volume ranging from 0.1 to 100 nL. In a specific embodiment, as shown in FIG. 11B, the isolation region 1140 may hold a volume of 6 nL. The sequestration pens 1124, 1126 can accommodate as many as 100, 200, 300, 400 or 500 micro-objects. In some embodiments, the sequestration pens may accommodate a maximum of 300-400 micro-objects.

The sequestration pens 1124, 1126, each have a connection region 1136 that is configured to separate biological micro-objects 1102 in the isolation region 1140 from the connection region 1136, creating sufficient distance for the secreted analyte to diffuse away from its source (e.g., one of the biological micro-objects 1102 secreting the analyte). This separation reduces interference or overlap of localized signal from RMSA complexes still associated at or on the biological micro-object 1102 (e.g., not freely diffusing) with its diffusion trajectory along line of anticipated diffusion trajectory 1130. By eliminating this overlap, concentration values generated from the at least a portion of the AOI or the entire AOI will represent signal from the bound reporter molecule as it diffuses. In some embodiments, the connection region 1136 is separated from the isolation region 1140 by constriction of the connection region 1136 relative to the isolation region 1140. In some embodiments, the connection region 1136 will have a width ranging from 10-30 microns and a length ranging from 40 to 200 microns. In a specific embodiment, the connection region 1136 is 20 microns in width and range from 100 to 200 microns in length.

FIG. 11B depicts the flux lines 1120 and concentration gradient lines 110 of secreted analyte of biological micro-object 1102 from within sequestration pen 1124, through the connection region 1136 and out to channel 122. Portions of the connection region 1136 may be selected as at least a portion of an AOI and may be part of the region which is insensitive to cell location and is sensitive to variance in intensities observed in the Assay image.

Assessing an Area of Interest (AOI). FIG. 12A shows a schematic representation of an AOI from which data is extracted for the determination of the relative or absolute amount of a secreted analyte from a biological micro-object. The AOI 1250 is selected to encompass: a region in the isolation region 1240, region in the connection region 1236 (of sequestration pen 1224 in microfluidic device 1200); and a portion of the channel 122, all of which is aligned along the axis of diffusion from the sequestration pen 1224 to the channel 122. In this embodiment, flow 242 is present in the microfluidic channel 122, reducing any detectable signal within the portion of the channel incorporated within the AOI. The selection of the point at which the AOI ends within the sequestration pen is made to prevent overlap with the biological object 1202 which secretes the analyte, and from which detectable signal emanates. As shown in FIG. 12A, lines of diffusion 1210 are directed towards the connection region 1236 and become aligned with the axis of diffusion as the connection region 1236 is entered. Concentration gradient lines 1220 are shown as well.

FIG. 12B is a photograph showing the Assay Image for a sequestration pen 1224, having an identification number 1260 of "327", which indicates its location within the microfluidic device 1200. The identification number assists in correlating brightfield and fluorescence image locations, and also assists users to select, manipulate and export cells from a selected sequestration pen. Sequestration pen 1224 of FIG. 12B has one biological micro-object 1202 present within the isolation region (not labelled). The Assay Image clearly shows extensive amount of fluorescence signal within the sequestration pen, emanating from biological micro-object 1202. The AOI 1250 is shown photographically imposed, and is aligned along the axis of diffusion and centered along the line of diffusion trajectory 1252. The AOI is 20 pixels wide, which is chosen depending on the width of the connection region 126 (not labelled in FIG. 12B) and is divided into 20 sub-regions. An AOI may have other pixel sizes to each sub-region and the number of sub-regions may vary from about 1 to about 50. The sub-region 1254 of the AOI is the sub-region located furthest away from the channel 122 of all the sub-regions of the AOI, but is selected to not overlap with the biological micro-object 1202. The sub-region at the second end of the AOI is sub-region 1258, which is located within the channel 122. Importantly, the group of sub-regions 1256 is the Cell position insensitive region 944, 1044 of FIGS. 9A-B and 10A-B, from which the detected fluorescence is used to assess the relative or absolute amount of a secreted analyte of a biological micro-object within a sequestration pen.

FIG. 12C shows a graphical representation of the fluorescence detected in the AOI, where the values on the horizontal axis represent sub-regions 1 (corresponding to sub-region 1254 of FIG. 12B), the sub-region at the most proximal end of the AOI to the biological micro-object 1202, and sub-region 20 corresponds to the sub-region 1258 of FIG. 12B, at the most proximal end of the AOI in the channel 122. The amount of detected fluorescence in the AOI is proportional to the amount of secreted analyte. A variety of mathematical operations may be used to extract information about the relative or absolute amount of the secreted analyte and is discussed in detail in sections below.

Figure 13B:
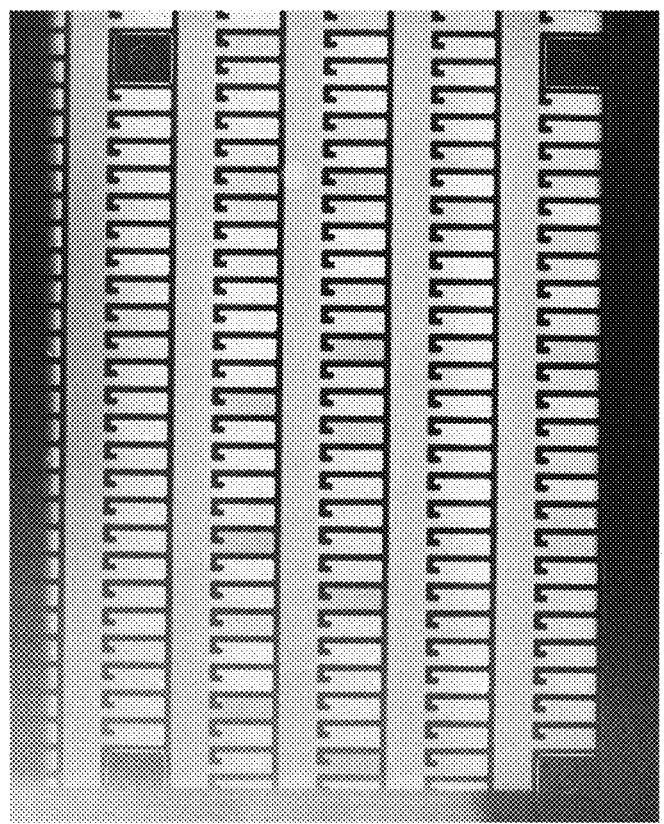
FIGS. 13A-13B depict photographic images of a microfluidic device before and after normalization according to some embodiments of the disclosure.
Figure 13A:
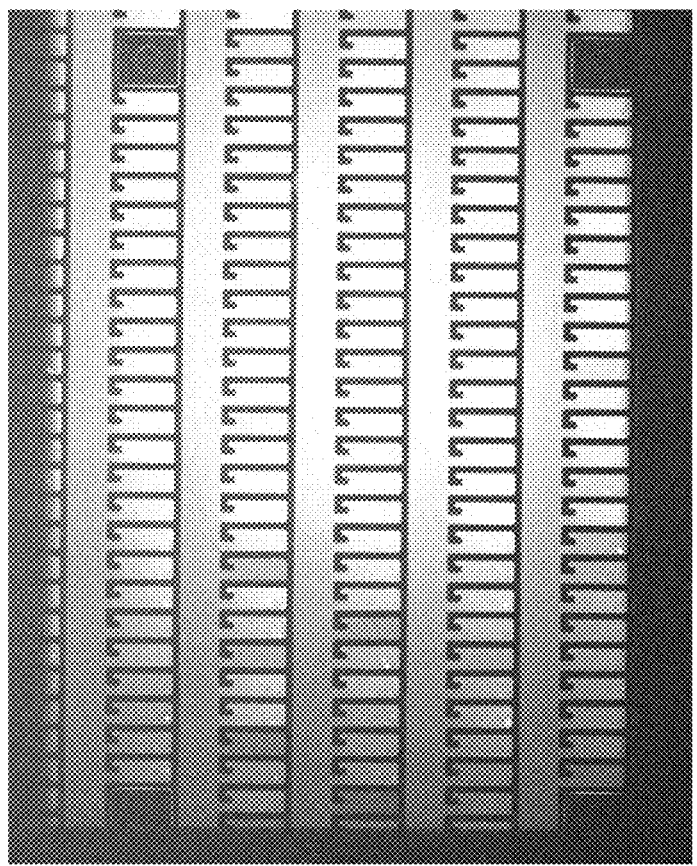

Normalization of the Assay image. Before the Assay Image can be processed to assess relative or absolute amounts of a secreted analyte, the raw Assay Image may be normalized. FIG. 13A shows a raw Assay Image which displays error such variance and non-linearity of system components such as the light source(s), the Light Modulating Subsystem (e.g. the DMD), the image capture device (e.g. the camera).

Method A for assays conducted under flow conditions. In one embodiment, the raw Assay Image may be normalized by subtracting both a Dark Reference image and a Signal Reference image correction from each pixel in the raw Assay Image as in the following equation:

$$\text{Normalized Assay value} = \frac{\text{Assay intensity value} - \text{Dark Reference}}{\text{Signal Reference value} - \text{Dark Reference}} \quad \text{(Equation 3)}$$

The Dark Reference image may be obtained by imaging the microfluidic device before flowing any medium into the device. Autofluorescence errors and other system errors can be corrected by subtracting the Dark Reference value at each pixel. The Signal Reference Image may correct for roll off, photobleaching errors or camera errors, and is obtained by flowing reporter molecule, or just the reporter molecule throughout the microfluidic device to reach an equilibrated concentration of the reporter molecule or fluorescent label. Each pixel in the raw Assay Image may be corrected in this manner, before extracting the fluorescence data for quantitation purposes. The normalized Assay Image is shown in FIG. 13B.

Method B for some embodiments of assays conducted under non-flow conditions. As a first step in normalization, the Dark Reference image, as described above, was subtracted from the image of the microfluidic device with the bound and unbound reporter molecules present to produce an "dark reference subtracted image."

As a second step, portions of the raw Assay image of FIG. 13A where the bound and unbound reporter molecules are not present (i.e. walls defining the sequestration pens and channels in the microfluidic device) were removed or "masked" from the auto-fluorescence subtracted image to produce a "masked dark reference subtracted image." As understood by those skilled in the art, this step also could be performed before the subtraction of auto-fluorescence.

As a third step in generating the normalized image of FIG. 13A, the intensity value for each pixel in the masked, auto-fluorescence subtracted image was divided by the global average intensity calculated based on all pixels in the masked, auto-fluorescence subtracted image. By dividing the intensity value for each pixel by the global average intensity, an image or similar data structure (e.g. a matrix) comprising a gain correction factor for each pixel is generated ("gain correction image") is for each pixel of the image is produced. Other methods of producing a gain correction image are well known to those skilled in the art.

As a fourth step in generating the normalized image depicted in FIG. 13A, the gain-correction image was subject to a smoothing algorithm to reduce random noise. This step may not be employed in some embodiments of the method. Specifically, the gain-correction image was subject to a box-filter smoothing algorithm that used a 9-pixel by 9-pixel box-filter that accounts for the masked portions of the image in generating a local average for each pixel. As can be appreciated by those skilled in the art, other smoothing algorithms such as mean filtering, Gaussian filtering, gradient weighting filtering, sequence statistical filtering, robust smoothing filtering, Crimmins noise removal filtering, edge preserved filtering and self-adaptive median filtering may be used.

As a fifth step in generating the normalized photograph depicted in FIG. 13B, the smoothed gain-correction image may be multiplied by the auto-fluorescence subtracted image to produce a normalized image.

These methods may combine any of the foregoing steps and methods in the same or different sequence.

Method C for some embodiments of assays conducted under non-flow conditions. Another method of normalizing the image may be used, depending on the substantially uniform concentration unbound reporter molecule within the channel due to its greater rate of diffusion over that of the bound RMSA complex. The brightness of the channels may be used to normalize the image to correct for the errors described above.

Therefore, in an alternate embodiment, the normalized image of FIG. 13B can be obtained using the brightness in the channels proximal to the pens to correct for any variance in the amount of brightness across the view of regions of the microfluidic device. This method of normalization relies on the fact that the channels are not expected to have any analyte (or any RMSA complex) present and therefore can be performed using any area of the microfluidic device that does not have the analyte present.

In order to normalize based on the channel intensity, as a first step, a region of the channel R that is not expected to have any analyte present in it is identified for each sequestration pen. In some embodiments, this region R can be a pre-defined region R corresponding to an area of the channel above the pen. In other embodiments, the region R for each sequestration pen can be identified based on other information or calculated based on the image.

For each region of the channel R, a brightness value $B_R$ is computed based on the pixels within the region. Prior to computing the brightness values, the image used to calculate the brightness value may be subtracted, masked or otherwise processed as discussed above. In some embodiments, $B_R$ is the average brightness value of the pixels within the region R.

After the average brightness value $B_R$ for each region R is computed, the image of the pens and channels may be partitioned into a series of areas A, where each area A encompasses a respective region R. This area may be computed so that a region R is in the center of an area A. In a specific embodiment, the areas A may be computed by generating a Voronoi diagram or a Delauney triangulation of the centroids of each region R. In other embodiments, each region R need not be centered in its respective area A and can be computed based on pre-defined areas segmenting the microfluidic device. For each area A, a gain-correction factor is calculated based on the maximum brightness value calculated for the brightest region $B_{Rmax}$ divided by the brightness value $B_R$ for the region R associated with the area A. The gain-correction factor may be used to generate a gain-correction image which can be multiplied against another image (e.g. the auto-fluorescence subtracted image) to produce a normalized image. The gain-correction factor image may also be smoothed as described above prior to use in normalization.

Quantification of the assay signal. In some embodiments, the diffusion profile of the RMSA may be used to quantify the amount of the RMSA present in the sequestration pen. The diffusion profile provides a series of values ("concentration values") that represent the concentration of the RMSA as it diffuses from its source to the channel.

After identification of the AOI, other transformations may be applied. For example, the pixels in each line may be processing by discarding outlier and/or aberrant pixels, other forms of global/local normalization, space conversion, and transforming the space of the pixel (e.g. from a multi-dimensional space to a two-dimensional space or vice-versa).

Depending on the embodiment, the intensity values may be used in different ways to calculate the concentration values. In some embodiments, the AOI may be sampled at fixed points to generate a set of concentration values corresponding to the intensity values at the fixed points. In some embodiments, the AOI may be segmented in a series of segments and the median or mean intensity of each segment may be calculated. Based on the embodiment and the degree of resolution required, the number of concentration values calculated can be as low as 1 and as high as the number of pixels in the line representing the diffusion trajectory.

Depending on the embodiment, the concentration values may be combined in different ways in order to quantify the amount of signal from the bound reporter molecule (and therefore the amount of secreted analyte) present. In some embodiments, the concentration values may be plotted to assess whether concentration values exhibit characteristics consistent with a diffusion profile. Depending on the embodiment, a number of algorithms may be used to fit a line to the concentration values and calculate characteristics of the line such as the slope and error associated with the line. Suitable line-fitting algorithms include: least-squares, polynomial fit, curve-fitting, and erfc fitting. Other algorithms are known to those skilled in the art. Methods of transforming fluorescence intensity values to obtain concentration values is described more fully below.

Figure 14C:
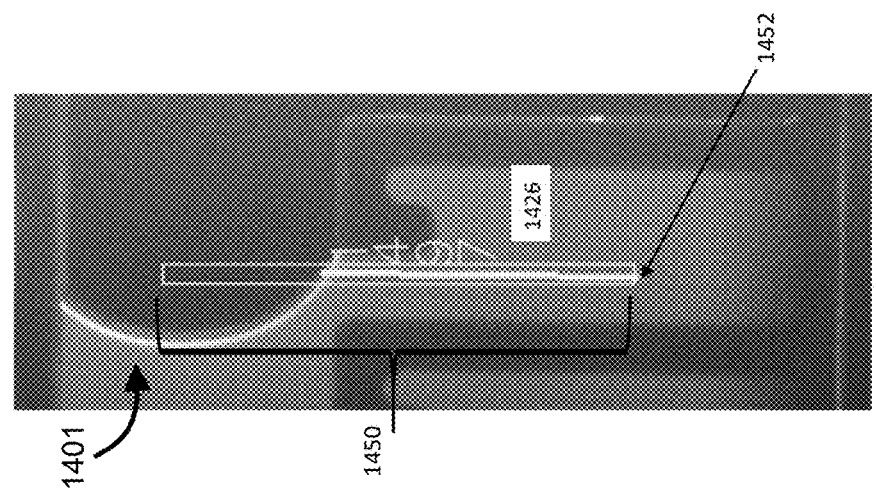
FIGS. 14A-14C are graphical and photographic representations of assay images within a microfluidic device and assay data for an area of interest thereof, according to some embodiments of the disclosure.
Figure 14B:
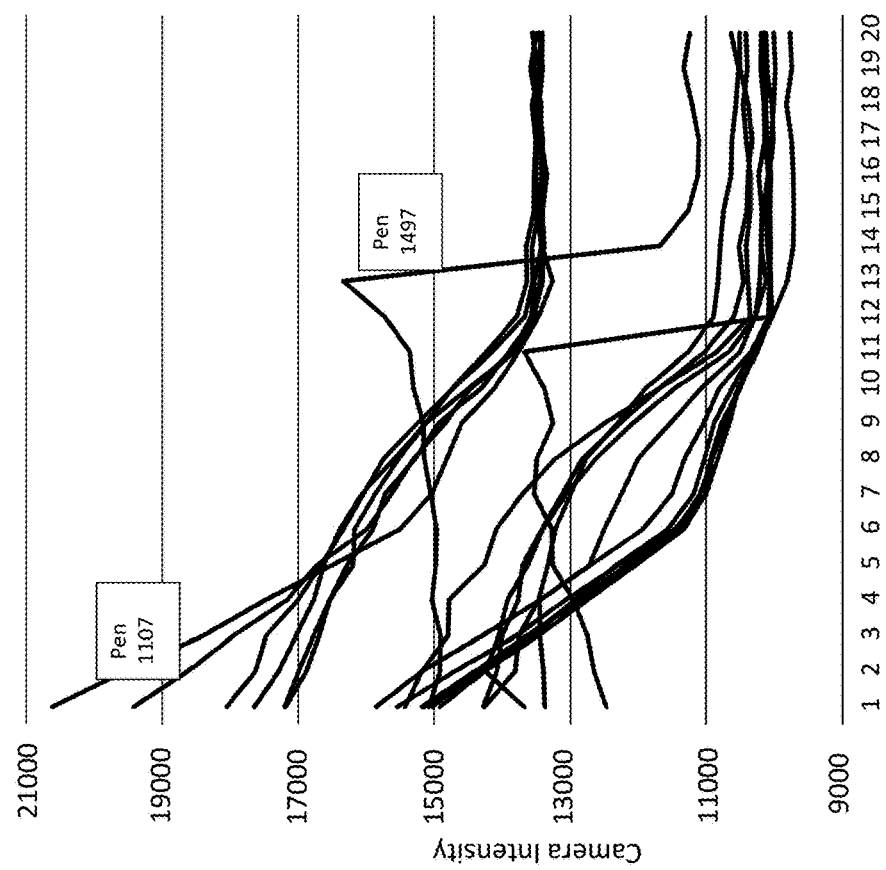
Figure 14A:
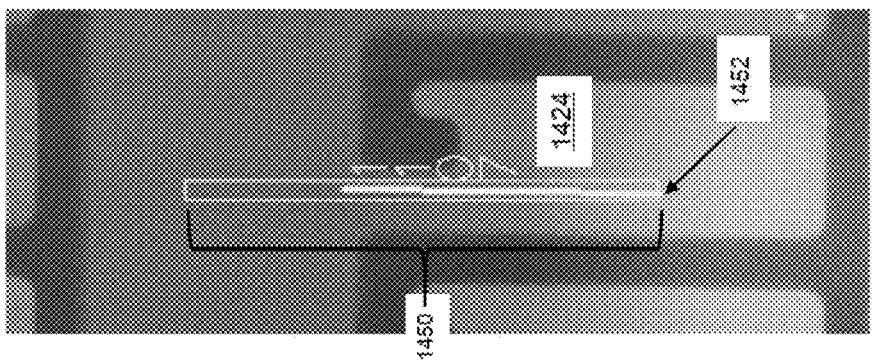

FIG. 14A is an Assay Image (photograph) of one sequestration pen 1424, having an identification number "1107", and wherein a line of anticipated diffusion trajectory 1452 is shown. An AOI 1450 is projected onto the Assay Image, and in this example, has a width of about 12 pixels, and it was segmented into 20 equal segments along the axis defined by the line (segments not shown). The median intensity for each of the 20 equal segments was calculated and then plotted as the concentration value in the graph of FIG. 14B. On the horizontal axis of the graphs, the segment numbers 1-20 are numbered according to their distance from the source (i.e. the cells secreting the secreted analyte), with the segment numbers having a low number representing the segment of the AOI closest to the cells in the region of the sequestration pen most distal from the channel.

FIG. 14B depicts a series of curves representing concentration values for a set of sequestration pens, which were generated according to the method discussed in the previous paragraph and other sections following. To generate the series of curves shown in FIG. 14B, the concentration values generated for each sequestration pen were not normalized based on the number of cells in the sequestration pen. However, in alternate embodiments, the concentration values and resultant curves may be normalized based on the number of cells in each sequestration pen. As shown in FIG. 14B, the slope of the curve (of concentration values) for each pen may be used to assess the relative amount of the secreted analyte present in each sequestration pen. In other words, the slope may be used as a score such that sequestration pens can be ranked and ordered relative to each other, and "slope" and "score", in some embodiments herein, may be used interchangeably. In some instances, the score may be referred to as a secretion score. More specifically, in instances where the secreted analyte is produced by a biological micro-object (e.g. cell) present in the sequestration pens, the slopes may be used to assess the relative ability of the cells in each sequestration pen to produce the secreted analyte (e.g. the relative ability of cells to secrete an antibody). As discussed below, a relative or absolute amount of the secreted analyte may be calculated using different methods, including summing all the points in the sub-region of the AOI which is insensitive to the positions of the cells in the sequestration pen and is most sensitive to variance in fluorescence intensity observed (e.g., regions 1256 of FIG. 12B, 1044 of FIGS. 10A-B, and 944 of FIGS. 9A-B).

In addition, the shape of the curve may be evaluated to assess whether the concentration values for each pen conform to expected parameters or indicate systemic error. For example, the shape of the curve labelled "Pen 1497" in FIG. 14B does not correspond to the shape of the curves observed for the other sequestration pens whereas the shape of the curve labelled "Pen 1107" does corresponds to the expected diffusion profile. As shown in FIG. 14A, Pen 1107 had a visible gradient of reporter molecule from its sequestration pen to the channel which resulted in its curve corresponding to an expected diffusion profile. As shown in FIG. 14C, a sequestration pen 1426, having identification no. Pen 1497, has a line of anticipated diffusion trajectory 1452 and AOI 1450. However, sequestration pen 1426 is proximal to a channel containing a bubble, where the meniscus 1401 of the bubble appears in the image as a white ellipse. The presence of the bubble results in the aberrant curve for Pen 1497 depicted in FIG. 14B. In various embodiments, the region of the segmented AOI that linear regression may be applied may be selected to be segments (sub-regions) 9-13, which as discussed above encompass portions of the connection region and have been identified to be most sensitive to fluorescence intensity variance and most insensitive to the location of biological micro-objects within the sequestration pen.

Figure 15:
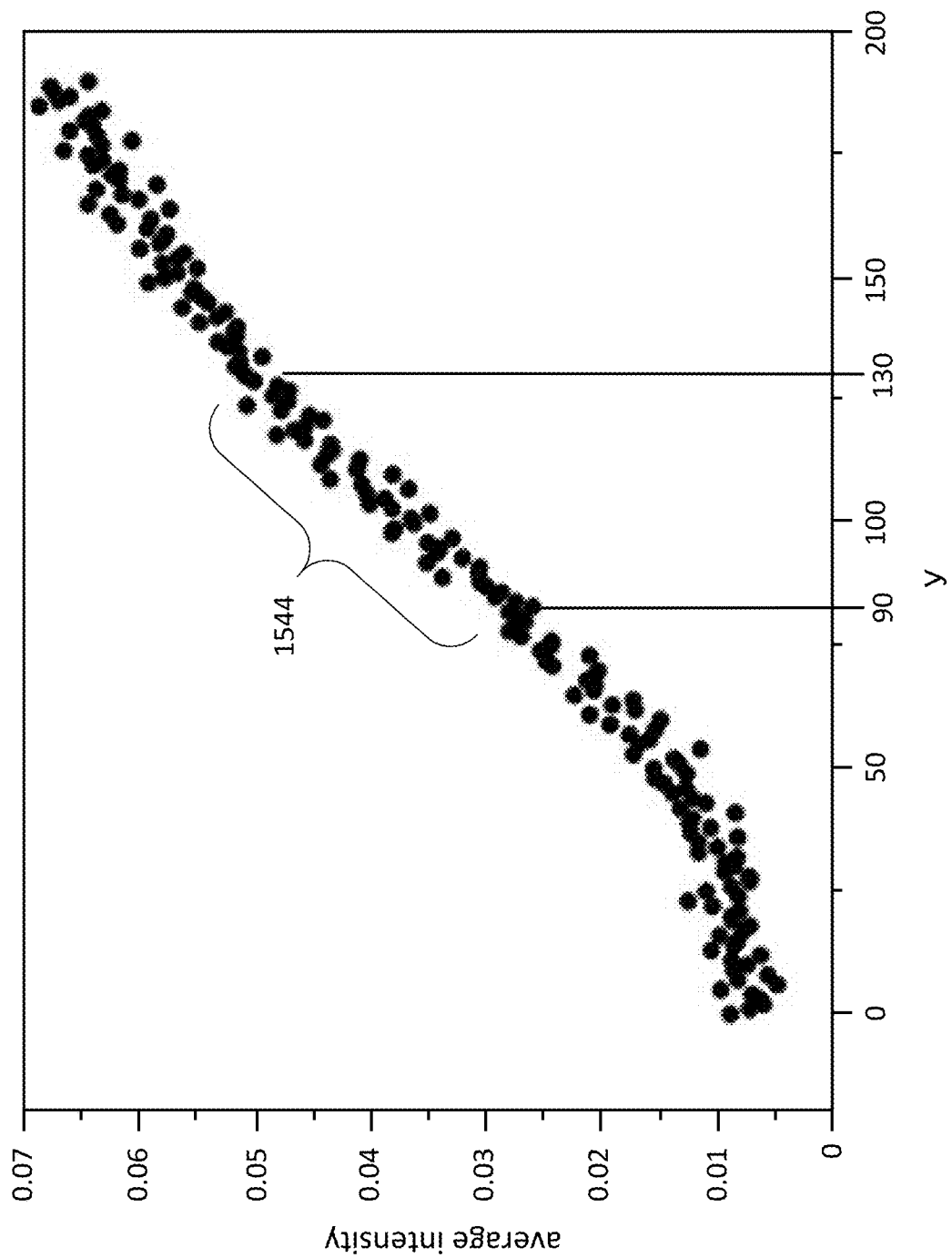
FIG. 15 is a graphical representation of an overlay of median intensity values for a plurality of chambers within a microfluidic device, according to some embodiments of the disclosure.

FIG. 15 shows an overlay of a plurality of curves representing intensity values (and thereby concentration values) derived via any of the methods described herein, obtained from a plurality of sequestration pens within a microfluidic device. The intensity values of each point in each curve, plotted against the vertical axis of the graph, have been normalized for ease of overlay. The values along the horizontal axis start with a value of "y" equal to zero, representing the first pixel in the y dimension of each AOI (and is physically located within the channel of the microfluidic device and outside of the sequestration pen, similarly to the AOIs shown in FIGS. 9A-B, 10A-B, 12A-b, and 14A and C. The points along the horizontal axis marked "200" correspond to the last pixel in each AOI of the plurality of sequestration pens, which is the boundary of the AOI closest to the cells secreting analyte, and hence the source from which the detectable signal from RMPCs emanates. The concentration values obtained from the portion 1544 of the AOI that is least sensitive to the position of cells within the sequestration pen and most sensitive to the variance in fluorescence intensities is shown in the portion of the curve associated with y values between about 90 and about 130, as shown. It can be seen that a mathematical operation imposing a linear shape in this region, and extracting the slope thereof, closely represents the state of the data.

Figure 16A:
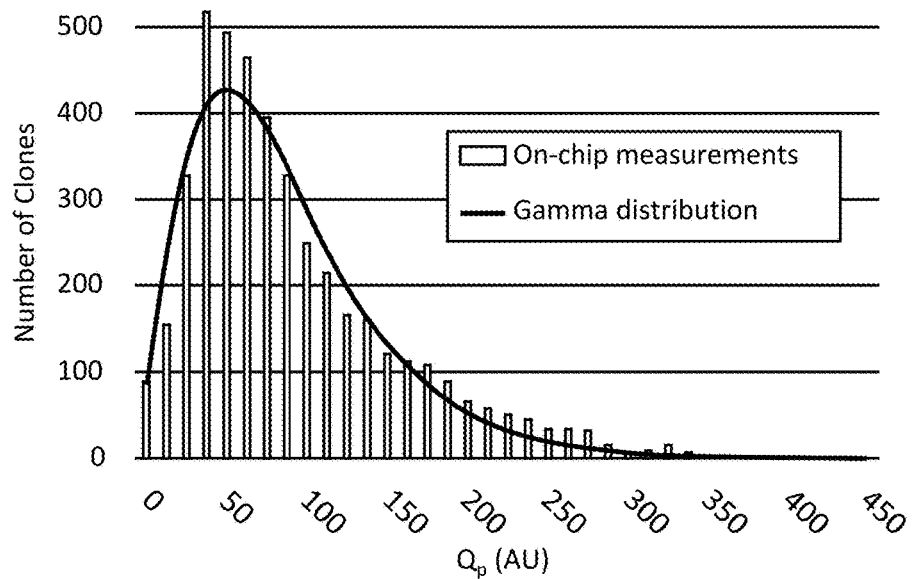
FIGS. 16A and 16B are graphical representations of analyte secretion by biological micro-objects disposed within a microfluidic device, according to some embodiments of the disclosure.

Performing the assay across the nanofluidic device containing thousands of clonal populations, each derived from a single cell placed into a separate sequestration pen, can provide quantification of each of the clonal populations. As shown in FIGS. 16A and B, the ability to find rare high producing clones is enhanced. If it is assumed that distribution of titers from a randomly secreting pool of cells is well described by Poisson statistics, then the titer distribution should fit to a gamma distribution. In FIG. 16A, the curve superimposed over the bar graph distribution of titers (which are obtained from the scores and normalized for number of cells present in each sequestration pen of the plurality, and expressed in Arbitrary Units (A.U.) shows good agreement. There is a great majority of clonal populations expressing analyte from less than 50 to less than 100 A.U, and very few individual titers out in the high range of 250 A. U. and over. The same data is now shown plotting the relative specific productivity against rate of growth (along the horizontal axis). The curves superimposed on the graph show lines of constant titer, which again show that the majority of clones whether they are fast or slow growing clones, express the analyte at less than 100 A.U. and are not the desirable highly producing clones sought for cell line development. Only a few clones identified within the regions 1670, 1680, and 1690 are the rare high producers. However, these clones are not the fastest producing clones arising out of the originally seeded single cells. If these cells were mixed in with other cells as part of a larger growth environment, such as a well plate or a shaker flask, these rare, highly producing clones would most likely be overgrown by the faster growing, less productive clones. Trying to identify these clones if one attempted selection of random single cell sets for expansion, would require a massive sampling effort with massive input of resources to grow up the number of cells that would be required to have the probability of seeing them. In the system provided here, the titer (or score), may be obtained for all of the clonal populations, and the physical location of the productive clones is known (see FIG. 21, below). Further, only the selected clones may be selected and physically moved for further expansion/subcloning; selection and movement may be performed individually to prevent contamination by other cell populations. The opportunity to screen all of the clones arising from the originally seeded cells provides a greatly improved process for screening and selecting cells that secrete a desired analyte.

Figure 31A:
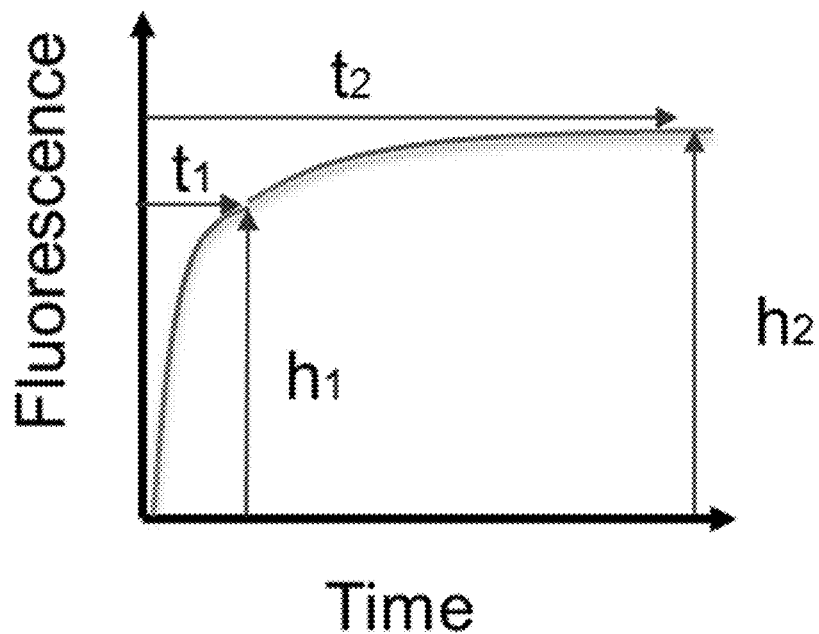
FIGS. 31A and 31B are exemplary graphs depicting the relationship between time and fluorescence, in accordance with various embodiments.
Figure 31B:
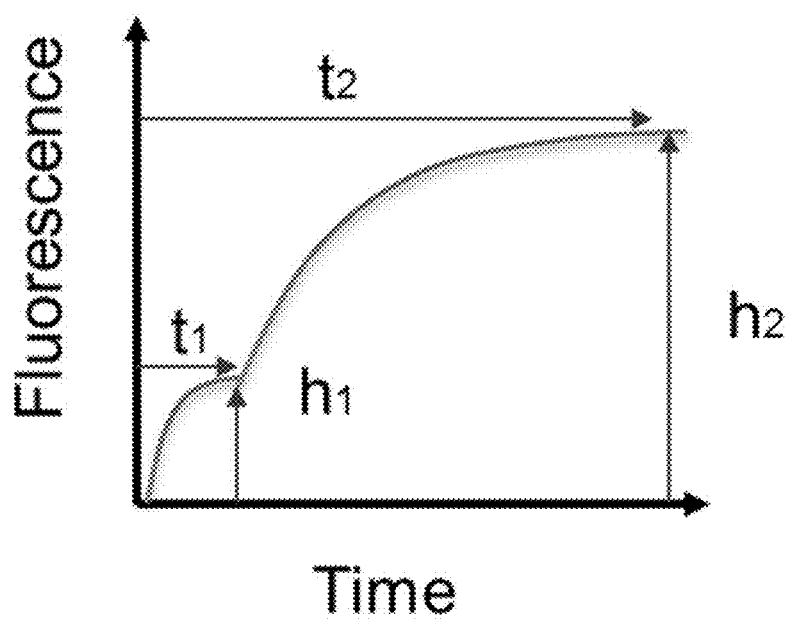

In accordance with various embodiments, fluorescence recovery after photobleaching (FRAP) can be another technique for making on-chip concentration measurements (i.e., secretion rate) of secreted molecules. In particular, the concentration and/or binding affinity of an unlabeled molecule secreted from a cell should be detectable by monitoring the fluorescence recovery after photobleaching. The technique can be implemented across various points in various cell line development assays (CLD assay) discussed herein such as, for example, during an equilibration step that is generally performed to create a homogeneous reagent concentration across the chip. FRAP could be performed during this step, where in each pen there is a population of free reagent, a population of secreted molecules, and a population of reagent bound to secreted molecule(s) of interest. By photobleaching an area of the pen, such as, for example, a 50-100 um box, or even the neck itself, free reagent and bound populations re-diffusing into that area can be observed. The free reagent generally recovers quickly because of its fast diffusion rate, while the bound complex recovers slowly due to its slower diffusion rate. The ratio of the fast-recovery process magnitude (h1 in FIGS. 31A and 31B) to the slow recovery process magnitude (h2 in FIGS. 31A and 31B) could then form a measure of concentration (secretion rate), with recovery time constants being determined by the molecular weights of the reagent and bound complex respectively. FIG. 31A represents a low secreting molecule while FIG. 31B represents a high secreting molecule. Moreover, OptoElectroPositioning (OEP) technology, discussed in more detail below, could be used to get more optical power to decrease bleach time, allow for use of a less stable dye, and allow for imaging at lower projector power during a monitoring step.

In accordance with various embodiments, therefore, a method of assessing a level of secretion of an analyte by a biological micro-object, or a population of biological micro-objects generated therefrom is provided. The method can comprise introducing the biological micro-object into a sequestration pen of a microfluidic device, wherein the microfluidic device comprises an enclosure having a flow region, wherein the sequestration pen is fluidically connected to the flow region, and wherein the sequestration pen contains a first fluidic medium. The method can further include allowing the biological micro-object, or the population of biological micro-objects generated therefrom, to secrete an analyte into the first fluidic medium within the sequestration pen, and introducing a second fluidic medium into the flow region for a first period of time, wherein the second fluidic medium comprises a plurality of reporter molecules. The method can further include allowing a portion of the plurality of reporter molecules to diffuse into the sequestration pen and bind to the analyte secreted therein, thereby producing a plurality of reporter molecule: secreted analyte (RMSA) complexes, and detecting reporter molecules located within an area of interest within the microfluidic device, wherein the area of interest includes at least a portion of the sequestration pen. The reporter molecule (or each reporter molecule) can comprise a binding component configured to bind the secreted analyte, and a detectable label.

In accordance with various embodiments, a non-transitory computer-readable medium is provided in which a program is stored for causing a computer to direct a system to perform a method for determining a quantity of analyte produced by a biological micro-object, or a population of biological micro-objects generated therefrom, using FRAP techniques. An example computer system for this is provided by the block diagram of FIG. 25 illustrating a computer system 3100, upon which embodiments of the present teachings may be implemented. Details of computer system 3100 will be provided below.

In accordance with various embodiments for assessing a level of secretion of an analyte by a biological micro-object, or a population of biological micro-objects generated therefrom, using FRAP techniques, the detectable label can comprises a visible, luminescent, phosphorescent, or fluorescent label. The detectable label of the reporter molecules can be a fluorescent label, wherein said detecting the reporter molecules comprises detecting fluorescence emission from the fluorescent label of the reporter molecules within the area of interest.

In accordance with various embodiments for assessing a level of secretion of an analyte by a biological micro-object, or a population of biological micro-objects generated therefrom, using FRAP techniques, methods can further comprise exposing, for a second period of time, a portion of the microfluidic device comprising the sequestration pen to electromagnetic radiation comprising a wavelength which is capable of exciting the fluorescent label of the reporter molecules. Methods can further comprise detecting fluorescence emission within the area of interest is performed after the second period of time, detecting fluorescence emission within the area of interest is performed two or more times during a third period of time, and/or detecting fluorescence emission within the area of interest is performed substantially continuously during a third period of time.

In accordance with various embodiments for assessing a level of secretion of an analyte by a biological micro-object, or a population of biological micro-objects generated therefrom, using FRAP techniques, methods can further include exposing, for a fourth period of time, a portion of the microfluidic device comprising at least a portion of the sequestration pen to electromagnetic radiation but not the flow region, wherein the fourth period of time is sufficient to photobleach the fluorescent label of any reporter molecules present in the portion of the sequestration pen, and detecting fluorescence emission within the photobleached portion of the sequestration pen. The detecting fluorescence emission within the photobleached portion of the sequestration pen can be performed after the fourth period of time, can be performed two or more times during a fifth period of time; and/or can be performed substantially continuously during a fifth period of time. Further, the detecting fluorescence emission within the photobleached portion of the sequestration pen can occur about 5 seconds to about 20 seconds after said exposing for a fourth period of time. Moreover, the steps of exposing for a fourth period of time and detecting fluorescence emission in the photobleached portion of the sequestration pen can be repeated one or more times.

In accordance with various embodiments for assessing a level of secretion of an analyte by a biological micro-object, or a population of biological micro-objects generated therefrom, using FRAP techniques, the photobleached portion of the sequestration pen is comprised by the area of interest.

In accordance with various embodiments for assessing a level of secretion of an analyte by a biological micro-object, or a population of biological micro-objects generated therefrom, using FRAP techniques, the sequestration pen has an isolation region and a connection region fluidically connecting the isolation region to the flow region, wherein the isolation region and the connection region are configured such that components of a fluidic medium in the isolation region are exchanged with components of a fluidic medium in the flow region substantially only by diffusion.

In accordance with various embodiments for assessing a level of secretion of an analyte by a biological micro-object, or a population of biological micro-objects generated therefrom, using FRAP techniques, the biological micro-object is a biological cell, and wherein the method further comprises expanding the biological cell within the sequestration pen into a clonal population of biological cells.

In accordance with various embodiments for assessing a level of secretion of an analyte by a biological micro-object, or a population of biological micro-objects generated therefrom, using FRAP techniques, methods can further comprise perfusing the flow region with a culturing medium, wherein the perfusing can occur after introducing the biological micro-object into the sequestration pen and before introducing the second fluidic medium into the flow region.

In accordance with various embodiments for assessing a level of secretion of an analyte by a biological micro-object, or a population of biological micro-objects generated therefrom, using FRAP techniques, the first period of time is about 30 minutes to about 60 minutes.

In accordance with various embodiments for assessing a level of secretion of an analyte by a biological micro-object, or a population of biological micro-objects generated therefrom, using FRAP techniques, methods can further include introducing a third fluidic medium into the flow region, wherein the third fluidic medium does not comprise any of the reporter molecules, and allowing at least a portion of unbound reporter molecules to diffuse out of the sequestration pen, wherein detecting the reporter molecules located within the area of interest occurs at a time selected such that an amount of unbound reporter molecules that have diffused out of the sequestration pen is at least 2× greater than an amount of RMSA complexes that have diffused out of the sequestration pen.

In accordance with various embodiments for assessing a level of secretion of an analyte by a biological micro-object, or a population of biological micro-objects generated therefrom, using FRAP techniques, wherein the area of interest can include at least a portion of the sequestration pen aligned along an axis of diffusion from within the sequestration pen to out into the flow region. The step of detecting the reporter molecules located within the area of interest can comprise measuring an intensity of a detectable signal coming from the area of interest, wherein at least some of the detectable signal emanates from the detectable label of reporter molecules located within the area of interest.

In accordance with various embodiments for assessing a level of secretion of an analyte by a biological micro-object, or a population of biological micro-objects generated therefrom, using FRAP techniques, the steps of detecting the reporter molecules located within the area of interest can further comprise determining a background-subtracted signal intensity by subtracting an intensity of a background signal from the measured intensity of the detectable signal. Methods can further comprise measuring an intensity of a background signal within the area of interest, at a time prior to introducing the biological micro-object into the sequestration pen. The measured intensity of the detectable signal or the background-subtracted signal intensity can be normalized for a number of cells observed within the sequestration pen.

In accordance with various embodiments for assessing a level of secretion of an analyte by a biological micro-object, or a population of biological micro-objects generated therefrom, using FRAP techniques, methods can further comprise quantifying the level of secretion of the analyte. Methods can further comprise providing a secretion score for the sequestration pen. The secretion score can be determined according to the method of any one of embodiments 12 to 25 (i.e., from the Recitation of Selected Embodiments below).

In accordance with various embodiments for assessing a level of secretion of an analyte by a biological micro-object, or a population of biological micro-objects generated therefrom, using FRAP techniques, the binding component of the reporter molecule can comprise a peptide or protein. The binding component of the reporter molecule can comprises a peptide having the sequence of any one of SEQ ID NOs: 1 to 10. The binding component of the reporter molecule can comprises protein A, protein G, or an IgG-binding fragment of protein A or protein G.

In accordance with various embodiments for assessing a level of secretion of an analyte by a biological micro-object, or a population of biological micro-objects generated therefrom, using FRAP techniques, the analyte secreted by the biological micro-object can be an antibody. The analyte secreted by the biological micro-object can be a protein other than an antibody.

In accordance with various embodiments for assessing a level of secretion of an analyte by a biological micro-object, or a population of biological micro-objects generated therefrom, using FRAP techniques, the microfluidic device can comprise a plurality of sequestration pens, wherein a biological micro-object is introduced into at least two sequestration pens of the plurality, and wherein the remainder of the method is carried out with respect to each of the at least two sequestration pens. Methods can further comprise comparing a level of secretion for sequestration pens of the at least two sequestration pens of the plurality.

In accordance with various embodiments for assessing a level of secretion of an analyte by a biological micro-object, or a population of biological micro-objects generated therefrom, using FRAP techniques, the area of interest can comprise an image area corresponding to an area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region.

Referring now to FIG. 32, in accordance with various embodiments, an example method for FRAP is provided. In Part A of FIG. 32, reagent is allowed to equilibrate across a pen. In Part B of FIG. 32, localized photobleaching is induced using, for example, structure light. As illustrated in this Figure, the localized area is box 3610. In Part C of FIG. 32, partial recovery has been observed as unbleached, free reagent enters the localized area 3630. As discussed above, free reagent generally recovers quickly because of its fast diffusion rate. In Part D of FIG. 32, full recovery is observed as unbleached, bound complex enters the localized area (not pictured as equilibrium has been reached, thus eliminating any observable localized area). As discussed above, bound complex generally recovers slowly (slower than free reagent) due to its slower diffusion rate and generally higher molecular weight.

FRAP has many potential advantages. For example, FRAP can allow for repeated assaying or at any time reagent is equilibrated. FRAP could be performed faster than typical diffusion gradient techniques. A FRAP user could acquire repeated time series secretion measurements to resolve biological spiking noise over time, thus potentially leading to improved biological noise statistics with fewer cells and shorter culture time. The concentration measurement would be independent both within and between fields of view because the technique measures the relative magnitude of the fast and slow recovery processes within the pen. This should not be affected by the order in which pens are imaged, or what part of the field of view the pen is in. Further, for example, FRAP could be used to measure binding affinity, because the ratio described above will also be strongly affected by the affinity.

Methods. A method for assessing a level of secretion of an analyte of a biological micro-objects, or a population of biological micro-objects generated therefrom is provided, the method including: introducing the biological micro-object into a sequestration pen of a microfluidic device, where the microfluidic device includes an enclosure having a flow region, wherein the sequestration pen is fluidically connected to the flow region, and wherein sequestration pen contains a first fluidic medium; allowing the biological micro-object, or the population of biological micro-objects generated therefrom, to secrete the analyte into the first fluidic medium within the sequestration pen; introducing a second fluidic medium into the flow region, where the second fluidic medium contains a plurality of reporter molecules, and where each reporter molecule includes a binding component configured to bind the secreted analyte; and a detectable label; allowing a portion of the plurality of reporter molecules to diffuse into the sequestration pen and bind to the analyte secreted therein, thereby producing a plurality of reporter molecule: secreted analyte (RMSA) complexes; and detecting reporter molecules located within an area of interest within the microfluidic device, wherein the area of interest includes at least a portion of the sequestration pen.

In some embodiments, the flow region may also contain the first fluidic medium. In other embodiments, the flow region may contain a fluidic medium different from the first fluidic medium.

In some embodiments, the reporter molecule may bind the secreted analyte, thereby forming a RMSA complex that may have a stoichiometry of 1:1, 2:1, 3:1, 4:1, 2:2, 4:2, and the like, of the reporter molecule: secreted analyte of the RMSA complex.

In various embodiments of the method for assessing a level of secretion of an analyte, detecting reporter molecules may include detecting unbound reporter molecules as well as detecting reporter molecules that are part of RMSA complexes.

In various embodiments, the sequestration pen may have an isolation region and a connection region fluidically connecting the isolation region to the flow region, wherein the isolation region and the connection region are configured such that components of a fluidic medium in the isolation region are exchanged with components of a fluidic medium in the flow region substantially only by diffusion.

In various embodiments of the method for assessing a level of secretion of an analyte, the method further includes expanding the biological micro-object within the sequestration pen into a clonal population of biological micro-objects.

In various embodiments, the method may further include perfusing the flow region with a culturing medium, where the perfusing occurs after introducing the biological micro-object into the sequestration pen and before introducing the second fluidic medium into the flow region. In some embodiments, the culturing medium may be the same as the first medium.

In various embodiments, the culturing medium may include one or more of a soluble feeder cell component, a defined dissolved oxygen component, defined pH component, an exhausted growth medium component, and/or a soluble stimulatory component. In some embodiments, viability of the cells being cultured within the microfluidic device may be improved by including a portion of the supernatant culture medium of feeder cells that provide auxiliary biomolecules that stimulate or otherwise support the cells culturing within the microfluidic device. The feeder cells themselves may not be present within the microfluidic device but may be cultured in standard reaction vessels. Harvesting and delivery of portions of the culture medium conditioned by the presence of the feeder cells to the microfluidic device may be performed. In other embodiments, the amount of dissolved oxygen may be measured and altered as desired, which may a facile process within the microfluidic environment described here, as compared to such adjustment in culture wellplates, shake flasks and the like. In some other embodiments, the pH of the culture medium within the microfluidic environment may be monitored and altered, again a more facile process than in plasticware standardly used.

In yet other embodiments, exhausted growth medium may be added to the microfluidic environment, which can act as a selection mechanism to analyze which clones within the microfluidic environment may still produce the secreted analyte more readily or may be used to approximate the scaleup environment of various types of reaction vessels, which may include wellplates, shaker flasks and bioreactors. In yet other embodiments, soluble stimulatory components such as antibodies (including but not limited to CD28), cytokines, growth factors, and the like, which may stimulate the cells within the microfluidic environment to produce more rapidly or to produce different analytes than prior to introduction of the stimulatory component. In other embodiments, one or more compounds and/or reagents configured to prevent the cells from adhering to each other and the pens may be added to the culture medium.

In some embodiments, one or more of these additions to the culture medium may confer a selection pressure on one or more of the cells within the sequestration pens.

In various embodiments, introducing the second fluidic medium into the flow region includes flowing the second fluidic medium through the flow region for a first period of time. In some embodiments, the first period of time may be based on modelling of a diffusion profile for unbound reporter molecules. In some embodiments, the first period of time may be about 30 to about 60 minutes.

The method may further include introducing a third fluidic medium into the flow region, wherein the third fluidic medium does not include reporter molecules; and allowing at least a portion of unbound reporter molecules to diffuse out of the sequestration pen, where detecting the reporter molecules located within the area of interest occurs at a time selected such that an amount of unbound reporter molecules that have diffused out of the sequestration pen is at least 2× greater than an amount of RMSA complexes that have diffused out of the sequestration pen. Detecting may include detecting unbound reporter molecules and detecting the reporter molecules that are part of the RMSA complexes. In various embodiments, introducing the third fluidic medium into the flow region may include flowing the third fluidic medium through the flow region for a second period of time. In some embodiments, the second period of time may be selected based on modelling of diffusion profiles for unbound reporter molecules and RMSA complexes.

In various embodiments, the area of interest may include at least a portion of the sequestration pen aligned along an axis of diffusion from within the sequestration pen to out into the flow region. In various embodiments, detecting the reporter molecules located within the area of interest may include measuring an intensity of a detectable signal coming from the area of interest, wherein at least some of the detectable signal emanates from the detectable label of reporter molecules located within the area of interest. In some embodiments, at least 50%, 55%, 60%, 65%, 70%, 75%, 80%, 85%, 90%, 95%, 98%, or more of the detectable signal emanates from the detectable label of reporter molecules located within the area of interest. In some embodiments, detecting the reporter molecules located within the area of interest further may include determining a background-subtracted signal intensity by subtracting an intensity of a background signal from the measured intensity of the detectable signal. The background signal may not be measured every time reporter molecules are detected. In some embodiments, the background signal may be predetermined based on known/standard conditions (e.g., chip type, location of sequestration pen in the chip, type of detectable label, components of first fluidic medium).

The method may further include measuring an intensity of a background signal within the area of interest, at a time prior to introducing the biological micro-object into the sequestration pen. In various embodiments, the measured intensity of the detectable signal or the background-subtracted signal intensity may be normalized for a number of cells observed within the sequestration pen.

In various embodiments, the method may further include quantifying the level of secretion of the analyte. Quantifying the level of the secretion of the produce may be based on any of a number of measurements, such as the measured intensity of the detectable signal or the background-subtracted signal intensity, either of which may be normalized for vignetting in the field of view. The method may further include providing a secretion score for the sequestration pen. The secretion score may be determined according to any of the methods in the sections following which describe methods of processing the detected and/or normalized fluorescence signal.

In various embodiments, the secreted analyte may have a molecular weight at least twice as great as a molecular weight of the reporter molecules. In some embodiments, the secreted analyte may have a molecular weight at least four times greater than a molecular weight of the reporter molecules. In other embodiments, the secreted analyte may have a molecular weight at least ten times greater than a molecular weight of the reporter molecule.

In various embodiments, the binding component of the reporter molecule may include at least one amino acid and/or at least one nucleic acid. In some embodiments, the binding component of the reporter molecule may include a peptide or protein. In some embodiments, the binding component of the reporter molecule may include a peptide having the sequence of any one of SEQ ID NOs: 1 to 10. In some other embodiments, the binding component of the reporter molecule comprises protein A, protein G, or an IgG-binding fragment of protein A or protein G. In various embodiments, the binding component of the reporter molecule may include an aptamer.

In various embodiments, the detectable label may include a visible, luminescent, phosphorescent, or fluorescent label. In some embodiments, the detectable label may be a fluorescent label.

In various embodiments, the analyte secreted by the biological micro-object may include a protein, a saccharide, a nucleic acid, an organic molecule other than a protein, saccharide, or nucleic acid, a vesicle, or a virus. In some embodiments, the analyte secreted by the biological micro-object may be an antibody. In other embodiments, the analyte secreted by the biological micro-object may be a protein other than an antibody.

In various embodiments, the microfluidic device may include a plurality of sequestration pens, where the step of disposing may include disposing a biological micro-object within at least a portion of the plurality of sequestration pens. In various embodiments, the method may further include a step of comparing a level of secretion for each sequestration pen of a sub-set of the sequestration pens of the plurality of sequestration pens. The method may further include a step of comparing scores of more than one sequestration pens of the plurality of sequestration pens. In some embodiments, the method may further include a step of quantifying the level of secretion. In various embodiments, the method may further include a step of selecting one or more of the plurality of sequestration pens and exporting the biological micro-object or the population of biological micro-objects generated therefrom out of the selected one or more sequestration pens. In various embodiments, this method allows for subcloning and comparative analysis of subclones, by further expanding and assaying the resultant subclone populations. This may be accomplished by moving selected clonal population to another set of sequestration pens within the microfluidic device and expanding again for each individual cell of the selected population. In other embodiments, the method may further include a step of exporting the selected biological micro-object or the population of biological micro-objects generated therefrom out of the microfluidic device. In various embodiments, the step of export from either the sequestration pens to the channel or from the sequestration pen and/or channel out of the microfluidic device may be performed on each selected sequestration pen individually (e.g., cells from a set of selected sequestration pens may be exported in a series of export steps, one sequestration pen at a time). In some embodiments, the cells which are disposed within a sequestration pen can come from a previously assayed sequestration pen, allowing for subcloning and comparative analysis of subclones. For example, an absolute or relative value of a specific antibody may be used to select and expand cells that produce a high volume of the specific antibody. Similarly, an absolute or relative value of a family of proteins (e.g. antibodies with an IgG domain) may be used to selected and expand cells that produce a high volume of the antibody. In some embodiments, all the cells from a sequestration pen associated with a relative or absolute value representing the amount of a secreted analyte will be selected and expanded in the same sequestration pen or other contained area of the chip. In other embodiments, one or more of the cells from the same sequestration pen associated with a relative or absolute value representing the amount of a secreted analyte will be selected and expanded in different sequestration pens. In some embodiments, the above discussed steps to generate the relative or absolute value may be repeatedly performed (1×, 2×, 3×, 4×, or more times) on the expanded cells.

In another embodiment, application of this method may permit examination of the effects of specific conditions upon cells, with feedback from repeated assays. For example, conditions and materials more closely related to large scale production of a secreted analyte may be used, in order to find and characterize the most suitable clones for further examination. In another example, diverse stimulation protocols for B-cell antibody stimulation may be examined in a more reproducible manner, and may be assayed in order to more comparably assess the benefits of one protocol over another.

In accordance with various embodiments, a method of assessing a level of secretion of an analyte by a biological micro-object, or a population of biological micro-objects generated therefrom is provided. The method can comprise introducing the biological micro-object into a sequestration pen of a microfluidic device, wherein the microfluidic device can comprise an enclosure having a flow region, wherein the sequestration pen is fluidically connected to the flow region, and wherein the sequestration pen contains a first fluidic medium. The method can further comprise allowing the biological micro-object, or the population of biological micro-objects generated therefrom, to secrete an analyte comprising an exogenous tag into the first fluidic medium within the sequestration pen, and introducing a second fluidic medium into the flow region, wherein the second fluidic medium comprises a plurality of reporter molecules. The method can further include allowing a portion of the plurality of reporter molecules to diffuse into the sequestration pen and bind to the analyte secreted therein, thereby producing a plurality of reporter molecule: secreted analyte (RMSA) complexes, and detecting reporter molecules located within an area of interest within the microfluidic device, wherein the area of interest includes at least a portion of the sequestration pen. The reporter molecule (or each reporter molecule) can include a binding component configured to bind the exogenous tag of the secreted analyte, and a detectable label.

In accordance with various embodiments, a non-transitory computer-readable medium is provided in which a program is stored for causing a computer to direct a system to perform a method for utilizing an exogenous tag to determine a quantity of analyte produced by a biological micro-object, or a population of biological micro-objects generated therefrom. An example computer system for this is provided by the block diagram of FIG. 25 illustrating a computer system 3100, upon which embodiments of the present teachings may be implemented. Details of computer system 3100 will be provided below.

In accordance with various embodiments for utilizing an exogenous tag to assess a level of secretion of an analyte by a biological micro-object, or a population of biological micro-objects generated therefrom, the sequestration pen can have an isolation region and a connection region fluidically connecting the isolation region to the flow region, wherein the isolation region and the connection region are configured such that components of a fluidic medium in the isolation region are exchanged with components of a fluidic medium in the flow region substantially only by diffusion.

In accordance with various embodiments for utilizing an exogenous tag to assess a level of secretion of an analyte by a biological micro-object, or a population of biological micro-objects generated therefrom, the biological micro-object is a biological cell, wherein the method further comprises expanding the biological cell within the sequestration pen into a clonal population of biological cells.

In accordance with various embodiments for utilizing an exogenous tag to assess a level of secretion of an analyte by a biological micro-object, or a population of biological micro-objects generated therefrom, methods can further include perfusing the flow region with a culturing medium, wherein the perfusing can occur after introducing the biological micro-object into the sequestration pen and before introducing the second fluidic medium into the flow region.

In accordance with various embodiments for utilizing an exogenous tag to assess a level of secretion of an analyte by a biological micro-object, or a population of biological micro-objects generated therefrom, introducing the second fluidic medium into the flow region can comprise flowing the second fluidic medium through the flow region for a first period of time. The first period of time can be about 30 minutes to about 60 minutes.

In accordance with various embodiments for utilizing an exogenous tag to assess a level of secretion of an analyte by a biological micro-object, or a population of biological micro-objects generated therefrom, the detectable label can comprise a visible, luminescent, phosphorescent, or fluorescent label. The detectable label of the reporter molecules can be a fluorescent label, and wherein said detecting the reporter molecules comprises detecting fluorescence emission from the fluorescent label of the reporter molecules within the area of interest.

In accordance with various embodiments for utilizing an exogenous tag to assess a level of secretion of an analyte by a biological micro-object, or a population of biological micro-objects generated therefrom, methods can further comprise exposing, for a second period of time, a portion of the microfluidic device comprising the sequestration pen to electromagnetic radiation comprising a wavelength which is capable of exciting the fluorescent label of the reporter molecules. Moreover, detecting fluorescence emission within the area of interest can be performed after the second period of time, two or more times during a third period of time; and/or substantially continuously during a third period of time.

In accordance with various embodiments for utilizing an exogenous tag to assess a level of secretion of an analyte by a biological micro-object, or a population of biological micro-objects generated therefrom, methods can further comprise exposing, for a fourth period of time, a portion of the microfluidic device comprising at least a portion of the sequestration pen to electromagnetic radiation but not the flow region, wherein the fourth period of time is sufficient to photobleach the fluorescent label of any reporter molecules present in the portion of the sequestration pen, and detecting fluorescence emission within the photobleached portion of the sequestration pen. Moreover, detecting fluorescence emission within the photobleached portion of the sequestration pen can be performed after the fourth period of time, two or more times during a fifth period of time; and/or substantially continuously during a fifth period of time. Even further, said steps of exposing for a fourth period of time and detecting fluorescence emission within the photobleached portion of the sequestration pen can be repeated one or more times. The process of fluorescence recovery after photobleaching (FRAP) an area (region, area of interest, or region of interest) on a pen for making on-chip concentration measurements (i.e., secretion rate) of secreted molecules is discussed in greater detail below.

In accordance with various embodiments for utilizing an exogenous tag to assess a level of secretion of an analyte by a biological micro-object, or a population of biological micro-objects generated therefrom, methods can further comprise introducing a third fluidic medium into the flow region, wherein the third fluidic medium does not comprise any of the reporter molecules; and allowing at least a portion of unbound reporter molecules to diffuse out of the sequestration pen, wherein detecting the reporter molecules located within the area of interest occurs at a time selected such that an amount of unbound reporter molecules that have diffused out of the sequestration pen is at least 2× greater than an amount of RMSA complexes that have diffused out of the sequestration pen.

In accordance with various embodiments for utilizing an exogenous tag to assess a level of secretion of an analyte by a biological micro-object, or a population of biological micro-objects generated therefrom, methods can further comprise quantifying the level of secretion of the analyte. Methods can further comprise providing a secretion score for the sequestration pen.

In accordance with various embodiments for utilizing an exogenous tag to assess a level of secretion of an analyte by a biological micro-object, or a population of biological micro-objects generated therefrom, the exogenous tag of the secreted analyte can comprise a peptide sequence. The peptide sequence can comprises a FLAG epitope, a polyhistidine sequence, a hemagglutinin (HA) epitope, or a Myc epitope. The peptide sequence can comprise the amino acid sequence (from N-terminal to C-terminal) DYKDDDDK (SEQ ID NO: 11). The peptide sequence can comprise the amino acid sequence (from N-terminal to C-terminal) HHHHHH (SEQ ID NO: 12).

In accordance with various embodiments for utilizing an exogenous tag to assess a level of secretion of an analyte by a biological micro-object, or a population of biological micro-objects generated therefrom, the binding component of the reporter molecule is an antibody. The binding component of the reporter molecule can comprise a chelating agent.

In accordance with various embodiments for utilizing an exogenous tag to assess a level of secretion of an analyte by a biological micro-object, or a population of biological micro-objects generated therefrom, the analyte secreted by the biological micro-object can comprise a protein. The analyte secreted by the biological micro-object can be an antibody.

In accordance with various embodiments for utilizing an exogenous tag to assess a level of secretion of an analyte by a biological micro-object, or a population of biological micro-objects generated therefrom, the microfluidic device can comprise a plurality of sequestration pens, wherein a biological micro-object is introduced into at least two sequestration pens of the plurality, and wherein the remainder of the method is carried out with respect to each of the at least two sequestration pens. Methods can further comprise comparing a level of secretion for sequestration pens of the at least two sequestration pens of the plurality. Methods can further comprise selecting one or more of the at least two sequestration pens, and exporting one or more biological micro-objects from each of the selected sequestration pens out of the microfluidic device.

Figure 17:
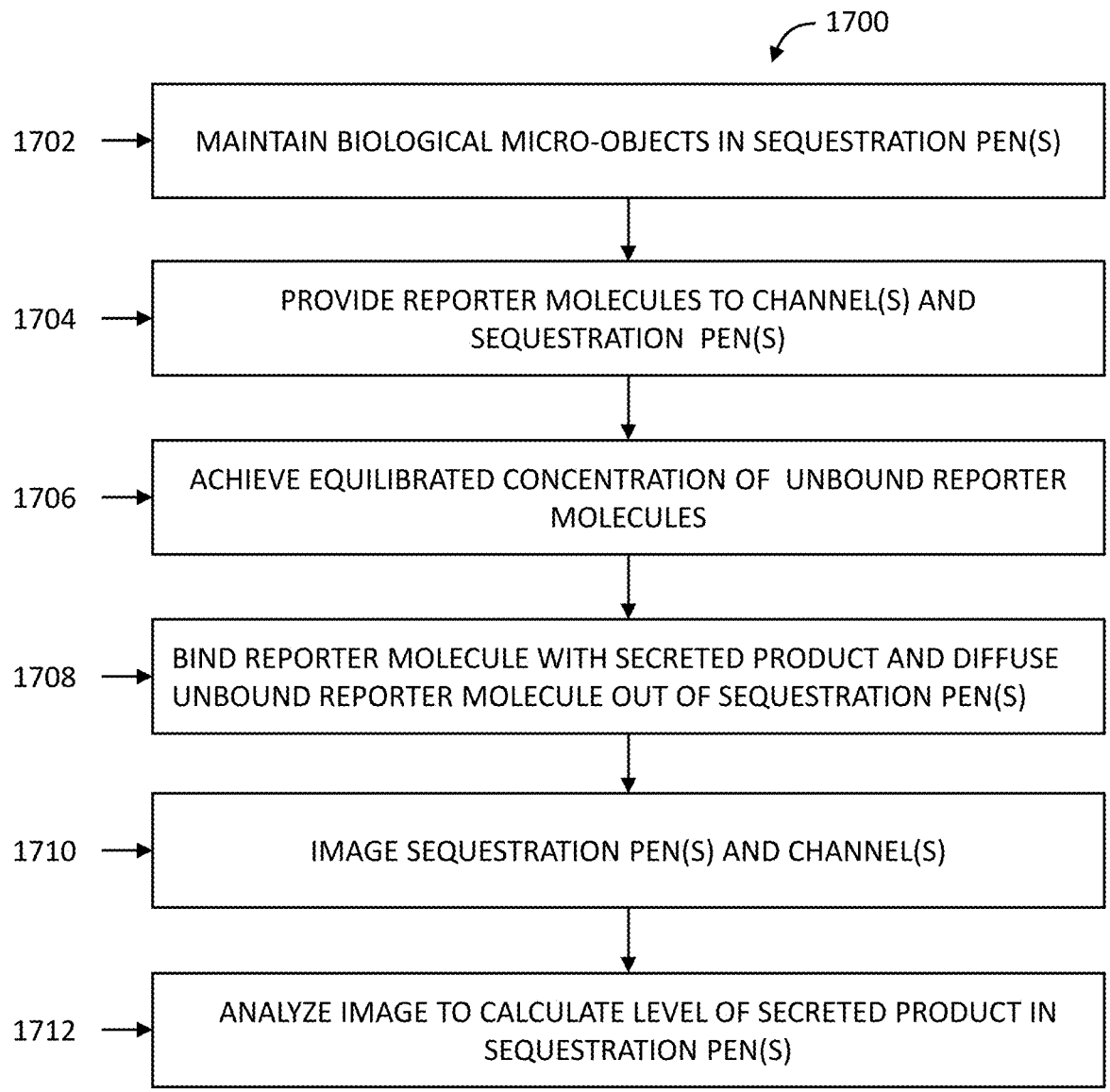
FIG. 17 illustrates steps performed to quantify an amount of analyte secreted by a biological micro-object present in sequestrations pens according to some embodiments of the present disclosure.

Turning now to FIG. 17, FIG. 17 illustrates functions performed to quantify an amount of secreted analyte present in sequestrations pens according to some embodiments of the present disclosure.

In box 1702, biological micro-objects that produce the secreted analyte are maintained in one or more sequestration pens in the microfluidic device. For example, the biological micro-objects may be cultured within the sequestration pens or loaded into the sequestration pens using a variety of means including gravity and/or dielectrophoretic forces, which may be optically actuated. Each pen may contain a single biological micro-object or a plurality of biological micro-objects. The plurality of biological micro-objects may be a clonal population of biological micro-objects (e.g. a clonal population of cells) generated therefrom the single biological micro-object or may be a heterogeneous population of biological micro-objects.

In box 1704, a reporter molecule having a signal component and a binding component that binds the secreted analyte is provided to the channel and the sequestration pens. For example, a reporter molecule may be flowed into the channel and allowed to diffuse into sequestration pens opening to the channel. Other means of providing the reporter molecule to the channel can be used.

In box 1706, the reporter molecule is allowed to diffuse within the microfluidic device (e.g. within the channel and sequestration pens) until it reaches a steady-state concentration equilibrium in its unbound state. Depending on the molecular weight of the reporter molecule, the amount of time needed to achieve a steady-state concentration equilibrium can vary.

In box 1708, the reporter molecule binds secreted analytes present in the sequestration pen. In some embodiments, flow is resumed within the channel and unbound reporter molecule diffuses out of the sequestration pen.

In box 1710, an image is generated of the sequestration pen(s) and channel(s) comprising the unbound reporter molecules and RMSA complexes. Depending on the signal component of the reporter molecule, it may be necessary to subject the microfluidic device to a specific light (e.g. subjecting a fluorophore to a specific frequency of light) or introduce an additional reagent to visualize the signal component.

In box 1712, the image of the sequestration pen(s) and channel(s) is analyzed to calculate an amount of the secreted analyte present in the sequestration pen(s).

In accordance with the various embodiments discussed herein, the microfluidic device can comprise a plurality of sequestration pens, wherein a biological micro-object is introduced into at least two sequestration pens of the plurality, and wherein the remainder of the method is carried out with respect to each of the at least two sequestration pens. Further, an example method for clonal line development is provided, the method further comprising comparing a level of secretion for sequestration pens of the at least two sequestration pens of the plurality. Further, methods can include selecting a set of sequestration pens from the plurality of sequestration pens, wherein each sequestration pen of the set has a score indicating that the biological micro-object, or clonal population, contained therein is a top analyte producer, exporting from the microfluidic device one or more biological micro-objects contained within each sequestration pen of the set of selected sequestration pens, expanding the exported one or more biological micro-objects from each sequestration pen of the set of selected sequestration pens in corresponding reaction vessels, and determining a level of analyte secreted in each corresponding reaction vessel, thereby determining a level of secretion for each biological micro-object or clonal population.

In accordance with various embodiments, a non-transitory computer-readable medium is provided in which a program is stored for causing a computer to direct a system to perform at least part of methods for clonal line development. The system can perform at least the steps up until and including exporting from the microfluidic device the one or more biological micro-objects contained within each sequestration pen of the set of selected sequestration pens. An example computer system for this is provided by the block diagram of FIG. 25 illustrating a computer system 3100, upon which embodiments of the present teachings may be implemented. Details of computer system 3100 will be provided below.

Figure 18:
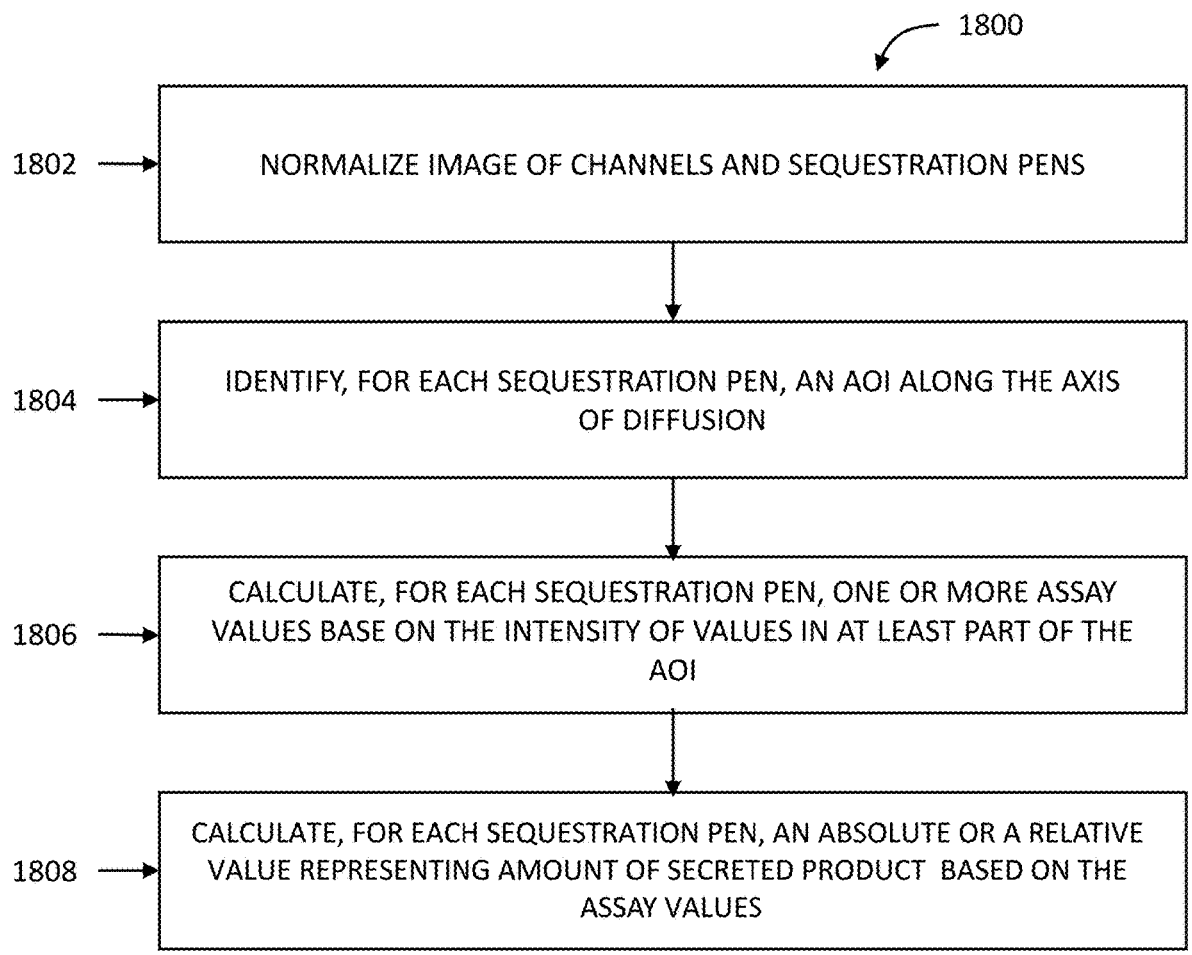
FIG. 18 illustrates a sequence of steps performed to calculate an absolute or relative value representing the amount of analyte secreted by a biological micro-object according to some embodiments of the disclosure.

Now turning to FIG. 18, FIG. 18 illustrates functions performed to calculate an absolute or relative value representing the amount of secreted analyte according to some embodiments of the disclosure.

In box 1802, an image of the microfluidic device comprising channel(s) and sequestration pen(s) is normalized to correct for systemic error. As discussed above, a number of different normalization algorithms may be used to correct for systemic error. In some embodiments, a gain-correction factor is used to normalize the image. In some embodiments, the amount of fluorescence signal present in the channel adjacent to a sequestration pen is used to normalize the image. In some embodiments, an auto-fluorescence image is subtracted from the image of the microfluidic device during normalization.

In box 1804, a line representing the axis of anticipated diffusion trajectory from the source of the secreted analyte within a pen (e.g. cells within a pen) to the channel proximal to the pen is identified. An AOI is identified that is aligned along the axis of anticipated diffusion trajectory, and extends from within the sequestration pen to into the channel. At least a portion of the AOI includes a region having the greatest sensitivity to signal intensity while also being insensitive to cell location within the sequestration pen. As discussed above, the AOI and the respective region having greatest sensitivity to signal/insensitive to cell location may be determined by computationally modeling a number of different parameters including but not limited to: the geometry of the sequestration pen, the position of the source of the secreted analyte within the pen, the molecular weight of the secreted analyte and the presence (or absence) of a flow within the channel.

In box 1806, one or more concentration values are generated based on the at AOI containing the at least a portion of the AOI that is insensitive to cell location and is most sensitive to signal variance. According to the embodiment, the concentration values may be calculated based on sampling pixels within the AOI or segmenting the AOI into groups of pixels.

In box 1808, the one or more concentration values are used to calculate a relative or an absolute value representing the amount of secreted analyte present in each sequestration pen. As discussed above, the one or more concentration values calculated for a given sequestration pen may be normalized based on the number of biological micro-objects (e.g. cells) present in each sequestration pen. In some embodiments, the one or more concentration values may be used to generate a curve or other composite value representing the diffusion profile from the source of the secreted analyte to the channel. In these embodiments, a slope of a line fitted to the curve of concentration values (or other composite value) may assess a secretion score associated with sequestration pens and may be used to assess the amount of secreted analyte present in each sequestration pen relative to the other sequestration pens (i.e. a relative value of the secreted analyte).

In another aspect, a method of clonal line development is provided, the method including: introducing an individual biological micro-object into each of a plurality of sequestration pens of a microfluidic device, where the microfluidic device further includes an enclosure having a flow region, and where each of the sequestration pens of the plurality is fluidically connected to the flow region and contains a first fluidic medium; allowing each biological micro-object, or a clonal population of biological micro-objects generated therefrom, to secrete an analyte into the first fluidic medium contained in the corresponding sequestration pen; introducing a second fluidic medium into the flow region, where the second fluidic medium includes a plurality of reporter molecules, where each reporter molecule includes a binding component configured to bind the secreted analyte; and a detectable label; allowing a portion of the plurality of reporter molecules to diffuse into each sequestration pen of the plurality and bind to at least a portion of the analyte secreted therein, thereby producing a plurality of reporter molecule:secreted analyte (RMSA) complexes in each of the plurality of sequestration pens; detecting, for each sequestration pen of the plurality, an intensity of a signal emanating from a corresponding area of interest, where the area of interest includes at least a portion of the corresponding sequestration pen, and where at least a portion of the signal emanating from the area of interest emanates from the detectable label of reporter molecules located within the area of interest; determining, for each sequestration pen of the plurality, a score based upon the detected signal intensity emanating from the corresponding area of interest; selecting a set of sequestration pens from the plurality of sequestration pens, where each sequestration pen of the set has a score indicating that the biological micro-object, or clonal population, contained therein is a top analyte producer; exporting from the microfluidic device one or more biological micro-objects contained within each sequestration pen of the set of selected sequestration pens; expanding the exported one or more biological micro-objects from each sequestration pen of the set of selected sequestration pens in corresponding reaction vessels; and determining a level of analyte secreted in each corresponding reaction vessel, thereby determining a level of secretion for each biological micro-object or clonal population. A top analyte producer may be one of the top 50% of producers. In some embodiments, a top analyte producer produces analytes at a rate amongst the top 55%, 60%, 65%, 70%, 75%, 80%, 85%, 90%, 92%, 94%, 95%, 96%, 97%, 98%, 99% producing clones or higher. Alternatively, a top producer could produce analyte at greater than a threshold amount.

In various embodiments, the score can be the intensity of signal emanating from the corresponding area of interest, or it can be calculated based upon the intensity of signal emanating from the corresponding area of interest.

Each sequestration pen of the plurality may have an isolation region and a connection region fluidically connecting the isolation region to the flow region, and the isolation region and the connection region may be configured such that components of a fluidic medium in the isolation region are exchanged with components of a fluidic medium in the flow region substantially only by diffusion.

In various embodiments, the method further includes expanding the individual biological micro-object within some or all sequestration pens of the plurality into a clonal population of biological micro-objects. In various embodiments, the method further includes perfusing the flow region with a culturing medium, where the perfusing occurs after introducing the individual biological micro-objects into the plurality of sequestration pens and before introducing the second fluidic medium into the flow region. The culturing medium may be the same as the first medium. Perfusing may be performed continuously or intermittently.

In some embodiments, the culturing medium may include one or more of a soluble feeder cell component, a defined dissolved oxygen component, defined pH component, an exhausted growth medium component, and/or a soluble stimulatory component. In some embodiments, viability of the cells being cultured within the microfluidic device may be improved by including a portion of the supernatant culture medium of feeder cells that provide auxiliary biomolecules that stimulate or otherwise support the cells culturing within the microfluidic device. The feeder cells themselves may not be present within the microfluidic device but may be cultured in standard reaction vessels. Harvesting and delivery of portions of the culture medium conditioned by the presence of the feeder cells to the microfluidic device may be performed. In other embodiments, the amount of dissolved oxygen may be measured and altered as desired, which may a facile process within the microfluidic environment described here, as compared to such adjustment in culture wellplates, shake flasks and the like. In some other embodiments, the pH of the culture medium within the microfluidic environment may be monitored and altered, again a more facile process than in plasticware standardly used.

In yet other embodiments, exhausted growth medium may be added to the microfluidic environment, which can act as a selection mechanism to analyze which clones within the microfluidic environment may still produce the secreted analyte more readily or may be used to approximate the scaleup environment of various types of reaction vessels, which may include wellplates, shaker flasks and bioreactors. In yet other embodiments, soluble stimulatory components such as antibodies (including but not limited to CD28), cytokines, growth factors, and the like, which may stimulate the cells within the microfluidic environment to produce more rapidly or to produce different analytes than prior to introduction of the stimulatory component. In other embodiments, one or more compounds and/or reagents configured to prevent the cells from adhering to each other and the pens may be added to the culture medium.

In various embodiments of the method, introducing the second fluidic medium into the flow region may include flowing the second fluidic medium through the flow region for a first period of time. The first period of time may be selected based on modelling of a diffusion profile for unbound reporter molecules. In some embodiments, the first period of time may be about 30 to about 60 minutes.

In various embodiments, the method further includes: introducing a third fluidic medium into the flow region, where the third fluidic medium does not comprise reporter molecules; and allowing at least a portion of unbound reporter molecules to diffuse out of the sequestration pen, where detecting the intensity of the signal emanating from the corresponding area of interest of each sequestration pen of the plurality occurs at a time selected such that an amount of unbound reporter molecules that have diffused out of the sequestration pen is at least 2× greater than an amount of RMSA complexes that have diffused out of the sequestration pen. In some embodiments, introducing the third fluidic medium into the flow region may include flowing the third fluidic medium through the flow region for a second period of time. In some embodiments, the second period of time may be selected based on modelling of diffusion profiles for unbound reporter molecules and RMSA complexes. In some embodiments, the second period of time may be about 20 to about 50 minutes.

In various embodiments of the method, the area of interest may include at least a portion of the sequestration pen aligned along an axis of diffusion from within the sequestration pen to out into the flow region.

In various embodiments of the method, detecting the intensity of the signal emanating from the corresponding area of interest of each sequestration pen of the plurality may include subtracting an intensity of a background signal from the measured intensity of the detectable signal to determine a background-subtracted signal intensity. The background signal may not be measured every time reporter molecules are detected. In some embodiments, the background signal may be pre-determined based on known/standard conditions (e.g., chip type, location of sequestration pen in the chip, type of detectable label, components of first fluidic medium).

In various embodiments, the method may further include measuring an intensity of a background signal within the corresponding area of interest of each sequestration pen of the plurality, at a time prior to introducing the biological micro-objects into the sequestration pens. In some embodiments, the measured intensity of the detectable signal or the background-subtracted signal intensity may be normalized for a number of cells observed within the corresponding sequestration pen.

In various embodiments, the scores of the plurality of sequestration pens are determined according to any of the methods in the sections following which describe methods of processing the detected and/or normalized fluorescence signal.

In various embodiments, the secreted analyte may have a molecular weight at least twice as great as a molecular weight of the reporter molecules. In some embodiments, the secreted analyte may have a molecular weight at least four times greater than a molecular weight of the reporter molecules. In other embodiments, the secreted analyte may have a molecular weight at least ten times greater than a molecular weight of the reporter molecule.

In various embodiments, the binding component of the reporter molecule may include at least one amino acid and/or at least one nucleic acid. In some embodiments, the binding component of the reporter molecule may include a peptide or protein. In some embodiments, the binding component of the reporter molecule may include a peptide having the sequence of any one of SEQ ID NOs: 1 to 10. In some other embodiments, the binding component of the reporter molecule comprises protein A, protein G, or an IgG-binding fragment of protein A or protein G. In various embodiments, the binding component of the reporter molecule may include an aptamer.

In various embodiments, the detectable label may include a visible, luminescent, phosphorescent, or fluorescent label. In some embodiments, the detectable label may be a fluorescent label.

In various embodiments, the analyte secreted by the biological micro-object may include a protein, a saccharide, a nucleic acid, an organic molecule other than a protein, saccharide, or nucleic acid, a vesicle, or a virus. In some embodiments, the analyte secreted by the biological micro-object may be an antibody. In other embodiments, the analyte secreted by the biological micro-object may be a protein other than an antibody.

In various embodiments, the reaction vessels may be wells in a well-plate, shaker flasks, or bio-reactors. The reaction vessels may have a volume greater than about 20 microliters, about 100 microliters, about 1 milliliter, about 10 milliliters, about 100 mL, about 1 L, or more. A bio-reactor may have one or more of the following features: closed loop control of pH and dissolved oxygen (DO) with independent control of O2 and CO2, automated liquid handling for reactor set-up, feeds, base addition and sampling, which may more closely approximate the environment of a reactor used for mass production of a secreted analyte, which may have a volume of 20 L, 50 L, 50 gal, 200 gal, or more. The bio-reactor may have a relatively small volume such as 10 mL or 15 mL (e.g., an ambr15™ (TAP Biosystems) bioreactor). A bio-reactor may have integrated viability analysis capabilities.

Figure 19:
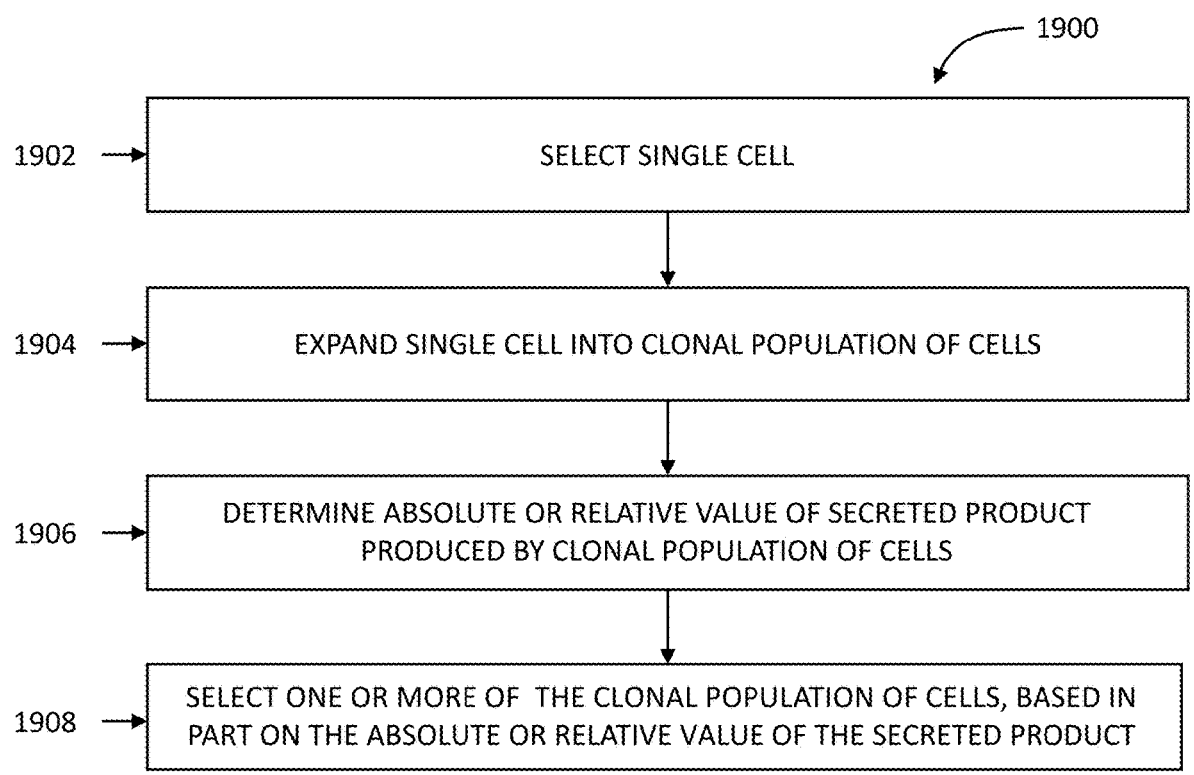
FIG. 19 illustrates steps performed to assess an absolute or relative value representing the amount of analyte secreted by a clonal population of cells according to some embodiments of the disclosure.

FIG. 19 illustrates functions performed to assess an absolute or relative value representing the amount of secreted analyte in a clonal population of cells according to some embodiments of the disclosure.

At box 1902, a single cell is selected for expansion. As discussed above, a cell may be selected based on the results of an assay or the cell may be selected based on other characteristics such as a phenotype and/or morphology.

At box 1904, the single cell is expanded into a clonal population of cells. In some embodiments, aspects of the clonal population of cells may be analyzed as the cells proliferate. For example, the rate of proliferation, the morphology of the cells and cell adhesion may be analyzed to assess the overall health and/or viability of the cells.

At box 1906, the absolute or relative value of a secreted analyte produced by the clonal population of cells is assessed. In some embodiments, the absolute or relative value may be assessed as described above with respect to FIGS. 12A-C and 15. In some embodiments, the absolute or relative value may be assessed using other methods, such as those described in U.S. patent application Ser. No. 14/964,025, the entirety of which is herein incorporated by reference.

At box 1908, one or more of the cells from the clonal population of cells may be selected based on the absolute or relative value of the secreted analyte produced by the clonal population of cells. In some embodiments, the one or more cells may be selected based on aspects of the clonal population of cells that are observed during cell proliferation as discussed above. In some embodiments, the selected cells may be exported for analysis or further expansion (e.g. expansion as a cell line to produce a secreted analyte). As discussed above, in some embodiments, the process of expanding a single cell and analyzing a clonal population for a production of a secreted analyte may be repeated to assess the absolute or relative amount of a second secreted analyte or to assess whether the single cell stably produces the secreted analyte quantified at box 1906.

Absolute value of secreted analyte concentration: titration curve. In some embodiments, a theoretical model of diffusion may be used to generate an absolute value based on the one or more concentration values and/or a known quantity of the secreted analyte of a biological micro-object in one of the pens. Depending on the embodiment, different theoretical models of diffusion may be used to calculate an absolute value of the analyte based on the one or more concentration values. Depending on the embodiment, the theoretical model may model various phenomena or evaluate different assumptions.

In some embodiments, a titration curve may be used to generate an absolute value of a secreted analyte of a biological micro-object. In these instances, various known amounts of the analyte may be introduced into the microfluidic device and used to generate absolute values representing the known amounts of the analyte. The absolute values representing the known amounts of the analyte may be used to generate a titration curve demonstrating, in part, a linear relationship between the absolute values and the various known amounts of the analyte. In some embodiments, a number of absolute values corresponding to known amounts of the analyte may be generated such that the titration curve contains a "dynamic range" showing the upper and lower bounds of accurate quantification of the analyte given various system parameters (i.e. the highest and lowest amount of the analyte that produces an absolute value having a linear relationship).

Depending on the embodiment, various methods of replicating an anticipated diffusion profile may be used to allow the concentration values for the known concentrations of analyte to be generated in the same manner as the analyte that is generated at a source in the sequestration pen (e.g. by a cell in a sequestration pen). In some embodiments, varying known concentrations of the analyte of interest are incubated with the reporter molecule. In most embodiments, the concentration of the reporter molecule will be in excess of the amount of reporter molecule necessary to bind all copies of the analyte. In some embodiments, the concentration of reporter molecule will be roughly 5-200 times the amount necessary to bind all copies of the analyte. However, this range can vary based on the binding affinity of the reporter molecule for the analyte. For example, in embodiments, where the reporter molecule has a strong binding affinity for the analyte, the concentration of the reporter molecule may range from 2-200 times the amount necessary to bind all copies of the analyte. In a specific embodiment where a FITC-labelled CPD 4 (Table 1) is used to bind IgG, the concentration of the FITC-labelled CPD 4 may range from 5-100 times the amount necessary to bind all copies of IgG. The method is not limited to the use of CPD 4 but may use any reporter molecule suitable for the diffusion assay itself. For example, fluorescently labeled CPD 1, CPD 2, CPD 3, CPD 5, CPD 6 (Table 1) may be used to generate a titration curve, and the fluorophore may be any suitably chosen fluorophore such as Alexa Fluor® 594 or HiLyte Fluor™ 555.

In some embodiments, an anticipated diffusion profile may be generated by providing the unbound reporter molecule and reporter molecule:analyte complex to the sequestration pens and channels of the microfluidic device for a sufficient time to allow the unbound and bound reporter molecule:analyte complex to enter the sequestration pens (i.e. perfusing the unbound and bound reporter molecule throughout the microfluidic device). After the RMSA complex and unbound reporter molecule is perfused throughout the microfluidic device, the channels are provided with a flow of another medium which eliminates (i.e. flushes) the RMSA complex and unbound reporter molecule from the channels and the swept regions of the sequestration pens. The RMSA complexes and unbound reporter molecules then diffuse from the sequestration pen to the channels. However, as discussed above, the unbound reporter molecules have a higher rate of diffusion than the RMSA complex Therefore, the unbound reporter molecules reach an equilibrium through the microfluidic device (i.e. have a same concentration in the channels and the sequestration pens) much faster than the RMSA complexes. This difference allows for the quantification of concentration values based on the median intensity values for sub-regions of an AOI (area of interest) as described above with respect to FIGS. 12A-C and 15, and discussed below with respect to the specific data manipulation.

Figure 20:
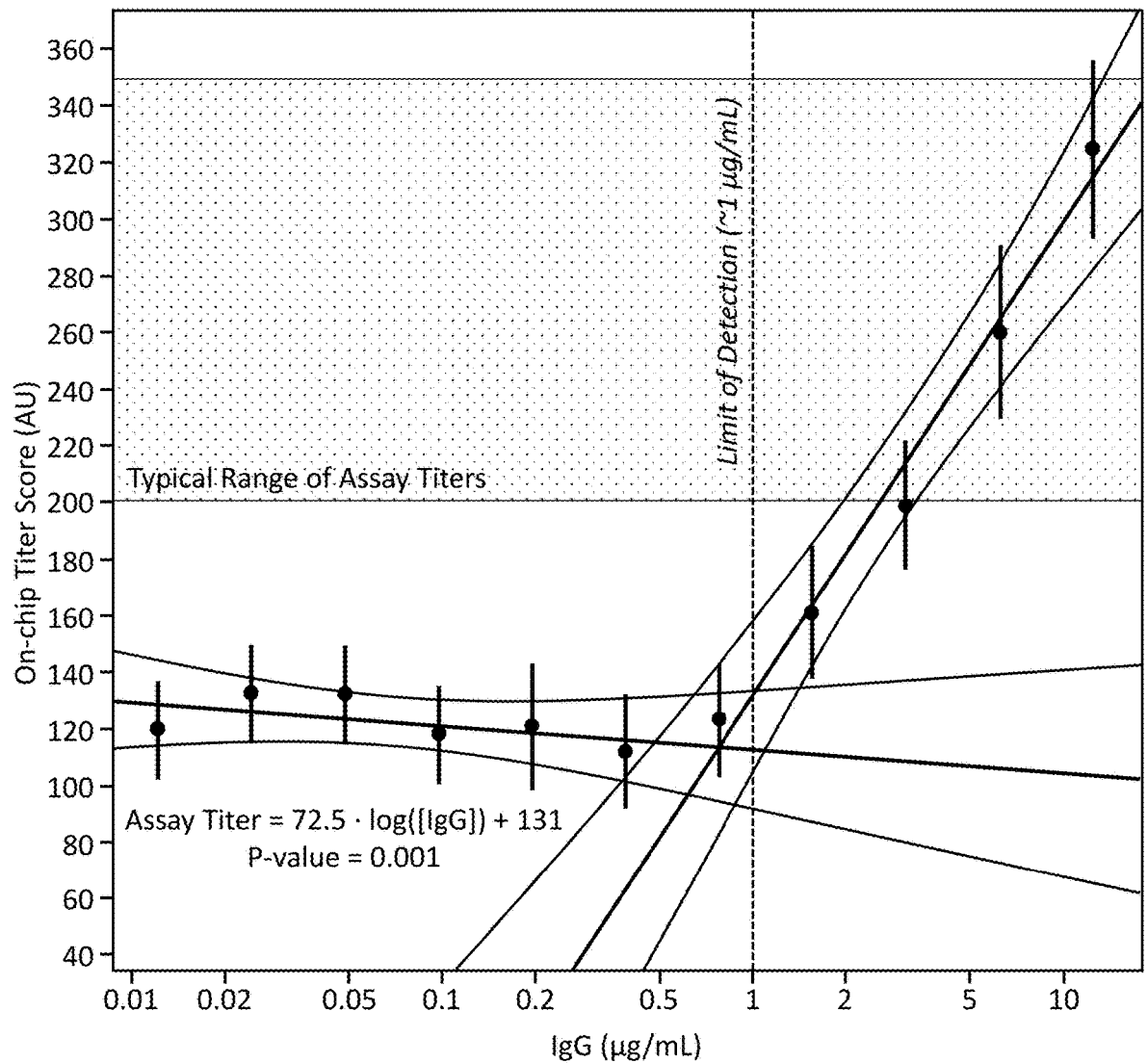
FIG. 20 is a graphical representation of a titration curve generated according to some embodiments of the disclosure.

FIG. 20 depicts a titration curve generated according to a specific embodiment. Specifically, FIG. 20 depicts a series of absolute values (labelled as "On-Chip Assay Titer Scores" on the y-axis) that correspond to known amounts of IgG (shown in micrograms/mL on the x-axis). Specifically, the known amounts of IgG used to generate the titration curve shown in FIG. 20 were 0.001526, 0.003052, 0.006104, 0.012207, 0.024414, 0.048828, 0.097656, 0.195313, 0.390625, 0.78125, 1.5625, 3.125, 6.25, 12.5 micrograms/ml.

To generate the absolute values representing the known amounts of IgG (labelled Assay Scores) shown in FIG. 20, known amounts of IgG were incubated in a solution containing FITC-labelled CPD 4. To ensure binding and detection of all copies of IgG, 6 times the amount of the FITC-labelled CPD 4 needed to bind all copies of IgG was included in the solution. The microfluidic device was then perfused for 45 minutes with the solution followed by flushing the channels with a cell line media (ThermoFisher CD CHO media) at a velocity of 10 microliters/second. After flushing the channels, the FITC-labelled CPD 4 and the IgG were allowed to diffuse from sequestration pen to the channel for 10 minutes. The microfluidic device is then imaged and used to generate Assay Scores for each of the sequestration pens in the microfluidic device as described below. This process was initially performed with the highest amount of IgG (i.e. 12.5 micrograms/mL) and consecutively repeated using lower amounts of IgG each time.

After imaging the microfluidic device, the Assay Scores for each known amount of IgG were calculated by taking the average of the individual absolute values generated for each sequestration pen in the microfluidic device. Each of the individual absolute values was generated by taking the slope of the concentration values generated for the sequestration pen as described above with respect to FIGS. 12-15. Specifically, the slope for each sequestration pen was calculated based on the concentration values generated based on the selected AOI. Prior to generating the concentration values, the image was normalized and subjected to a gain-correction factor as described above with respect to FIGS. 13A-B. After the slopes were calculated for each sequestration pen, the average of all the slopes for all of the sequestration pens in the microfluidic device was used as the Assay Score.

Once generated, a titration curve, such as that depicted in FIG. 20 may be used to generate absolute values of unknown quantities of secreted analyte. As shown in FIG. 20, the Assay Scores in the titration curve may be fitted with any line-fitting algorithm to produce a slope equation that defines the relationship between the absolute value (i.e. Assay Scores) and known amounts of the analyte (i.e. IgG). The slope equation can then be used to generate an absolute value representing the amount of analyte present under experimental conditions (i.e. cells producing unknown amounts of the analyte), given the Assay Scores observed under experimental conditions. To generate the titration curve shown in FIG. 20, a logarithmic fit model using 95% confidence intervals based on the standard deviation of the Assay Scores was generated using Tableau Software.

As shown in FIG. 20, the Assay Scores for the known amounts of IgG demonstrate a linear relationship starting at approximately 1 microgram/ml. That is, the Assay Scores demonstrate a proportional increase in response to the increasing amounts of IgG. At concentrations below 1 microgram/ml, no linear relationship is observed. Accordingly, the titration curve shown in FIG. 20 shows a dynamic range with a lower limit of accurate quantification at approximately 1 microgram/ml. The titration curve shown in FIG. 20 does not demonstrate an upper limit, as the Assay Score corresponding to the highest amount of IgG is within the range of Assay Score that exhibit a linear relationship with the known amounts of IgG.

As shown in the curve depicted in FIG. 20, the Assay Scores typically observed under experimental conditions (i.e. cells within sequestration pens secreting IgG) are marked on the titration curve in gray and labelled "Typical Range of Assay Titers." As the Assay Scores observed under experimental conditions are within the range of Assay Scores that demonstrate linear relationships with the known amounts of IgG, the slope generated for FIG. 20 can be used to calculate the amount of IgG that is typically produced under experimental conditions.

Kits. Kits may be provided for evaluation of secretion levels of an analyte of a biological micro-object or a population of biological micro-objects generated therefrom, including a microfluidic device comprising an enclosure having a flow region; and a sequestration pen, wherein the sequestration pen is fluidically connected to the flow region, and wherein the flow region and the sequestration pen is configured to contain a fluidic medium; and a reporter molecule comprising a detectable label and a binding component configured to bind the analyte.

In various embodiments of the kit, the sequestration pen of the microfluidic device may have an isolation region and a connection region fluidically connecting the isolation region to the flow region, where the isolation region and the connection region are configured such that components of the fluidic medium are exchanged between the flow region and the isolation region of the sequestration pen substantially only by diffusion. In various embodiments, the enclosure of the microfluidic device may include a base upon which the flow region and the sequestration pen are disposed. In some embodiments, the base of the enclosure may include a substrate having a dielectrophoretic configuration. The dielectrophoretic configuration may be optically actuated. In various embodiments, the flow region may be a channel. In some embodiments, the microfluidic device may include a plurality of sequestration pens, which may be configured like any sequestration pen as described herein. In some embodiments, at least one inner surface of the microfluidic device includes a covalently modified surface. In various embodiments, the microfluidic device of the kit may be configured like any microfluidic device described herein and may have any component, dimensions, and/or multiplicity of microfluidic circuit elements in any combination.

In various embodiments of the kit, the binding component of the reporter molecule may include at least one amino acid and/or at least one nucleic acid. In some embodiments, the binding component of the reporter molecule may include a peptide or protein. In various embodiments, the peptide or a protein binding component may be a peptide or a protein that binds human or murine IgG. In some embodiments, the binding component of the reporter molecule may be any of CPD 1, CPD 2, CPD 3, CPD 4, CPD 7, CPD 8, CPD 9, CPD 10, CPD 11, CPD 12, CPD 13 or CPD 14 (See Table 1). In some embodiments the binding component of the reporter molecule may be CPD 1, CPD 2, CPD 3 or CPD 4 (See Table 1). In some embodiments, the protein binding component that binds human or murine IgG may be CPD 1 or CPD 2 (See Table 1). In other embodiments, the binding component of the reporter molecule includes an aptamer. In various embodiments, the aptamer may be CPD 5 or CPD 6 (Table 1). In some embodiments, the aptamer binding component of the reporter molecule binds to Fc of an IgG.

In various embodiments of the kit, the detectable label of the reporter molecule may include a visible, luminescent, phosphorescent, or fluorescent label. In some embodiments, the detectable label is a fluorescent label. The fluorescent label may be a rhodamine, fluorescein, or cyanine fluorescent dye.

In various embodiments of the kit, the kit may also include a fluidic medium. The fluidic medium may be configured to maintain, expand or provide selective pressure to the biological micro-object or the population of biological micro-objects generated therefrom.

In various embodiments of the kit, the kit may also include a reagent configured to condition one or more surfaces of the microfluidic device. In some embodiments, the reagent may be configured to covalently modify the one or more surfaces of the microfluidic device.

In accordance with various embodiments, a kit is provided for evaluation of levels of an analyte secreted by a biological micro-object, or a population of biological micro-objects generated therefrom. The kit can include a microfluidic device and a reporter complex. The microfluidic device can comprise an enclosure having a flow region and a plurality of sequestration pens, wherein each sequestration pen is fluidically connected to the flow region, and wherein the flow region and the sequestration pens are configured to contain a fluidic medium. The reporter complex can comprise a first complex component configured to bind to the secreted analyte, and a second complex component bound to the first complex component and comprising a detectable label, wherein binding of the secreted analyte to the first complex component inhibits or prevents binding of the second complex component to the first complex component.

Computer-Implemented System. FIG. 25 is a block diagram that illustrates a computer system 3100, upon which embodiments of the present teachings may be implemented. In various embodiments of the present teachings, computer system 3100 can include a bus 3102 or other communication mechanism for communicating information, and a processor 3104 coupled with bus 3102 for processing information. In various embodiments, computer system 3100 can also include a memory 3106, which can be a random access memory (RAM) or other dynamic storage device, coupled to bus 3102 for determining instructions to be executed by processor 3104. Memory 3106 also can be used for storing temporary variables or other intermediate information during execution of instructions to be executed by processor 3104. In various embodiments, computer system 3100 can further include a read only memory (ROM) 3108 or other static storage device coupled to bus 3102 for storing static information and instructions for processor 3104. A storage device 3110, such as a magnetic disk or optical disk, can be provided and coupled to bus 3102 for storing information and instructions.

In various embodiments, computer system 3100 can be coupled via bus 3102 to a display 3112, such as a cathode ray tube (CRT) or liquid crystal display (LCD), for displaying information to a computer user. An input device 3114, including alphanumeric and other keys, can be coupled to bus 3102 for communicating information and command selections to processor 3104. Another type of user input device is a cursor control 3116, such as a mouse, a trackball or cursor direction keys for communicating direction information and command selections to processor 3104 and for controlling cursor movement on display 3112. This input device 3114 typically has two degrees of freedom in two axes, a first axis (i.e., x) and a second axis (i.e., y), that allows the device to specify positions in a plane. However, it should be understood that input devices 3114 allowing for 3 dimensional (x, y and z) cursor movement are also contemplated herein.

Consistent with certain implementations of the present teachings, results can be provided by computer system 3100 in response to processor 3104 executing one or more sequences of one or more instructions contained in memory 3106. Such instructions can be read into memory 3106 from another computer-readable medium or computer-readable storage medium, such as storage device 3110. Execution of the sequences of instructions contained in memory 3106 can cause processor 3104 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 3104 for execution. Such a medium can take many forms, including but not limited to, non-volatile media, volatile media, and transmission media. Examples of non-volatile media can include, but are not limited to, optical, solid state, magnetic disks, such as storage device 3110. Examples of volatile media can include, but are not limited to, dynamic memory, such as memory 3106. Examples of transmission media can include, but are not limited to, coaxial cables, copper wire, and fiber optics, including the wires that comprise bus 3102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 3104 of computer system 3100 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein flow charts, diagrams and accompanying disclosure can be implemented using computer system 3100 as a standalone device or on a distributed network of shared computer processing resources such as a cloud computing network.

Analyte Quantifier System. In accordance with various embodiments, systems and methods for determining a quantity of analyte produced by a micro-object are disclosed. The analyte can include, for example, secretions from a micro-object, where the micro-object can be a biological micro-object. The analyte can include, for example, a protein, a saccharide, a nucleic acid, antibody, antigen, an organic molecule other than a protein, saccharide or nucleic acid, a vesicle, or a virus. The quantity of analyte can be a relative quantity as will be discussed below.

Figure 26:
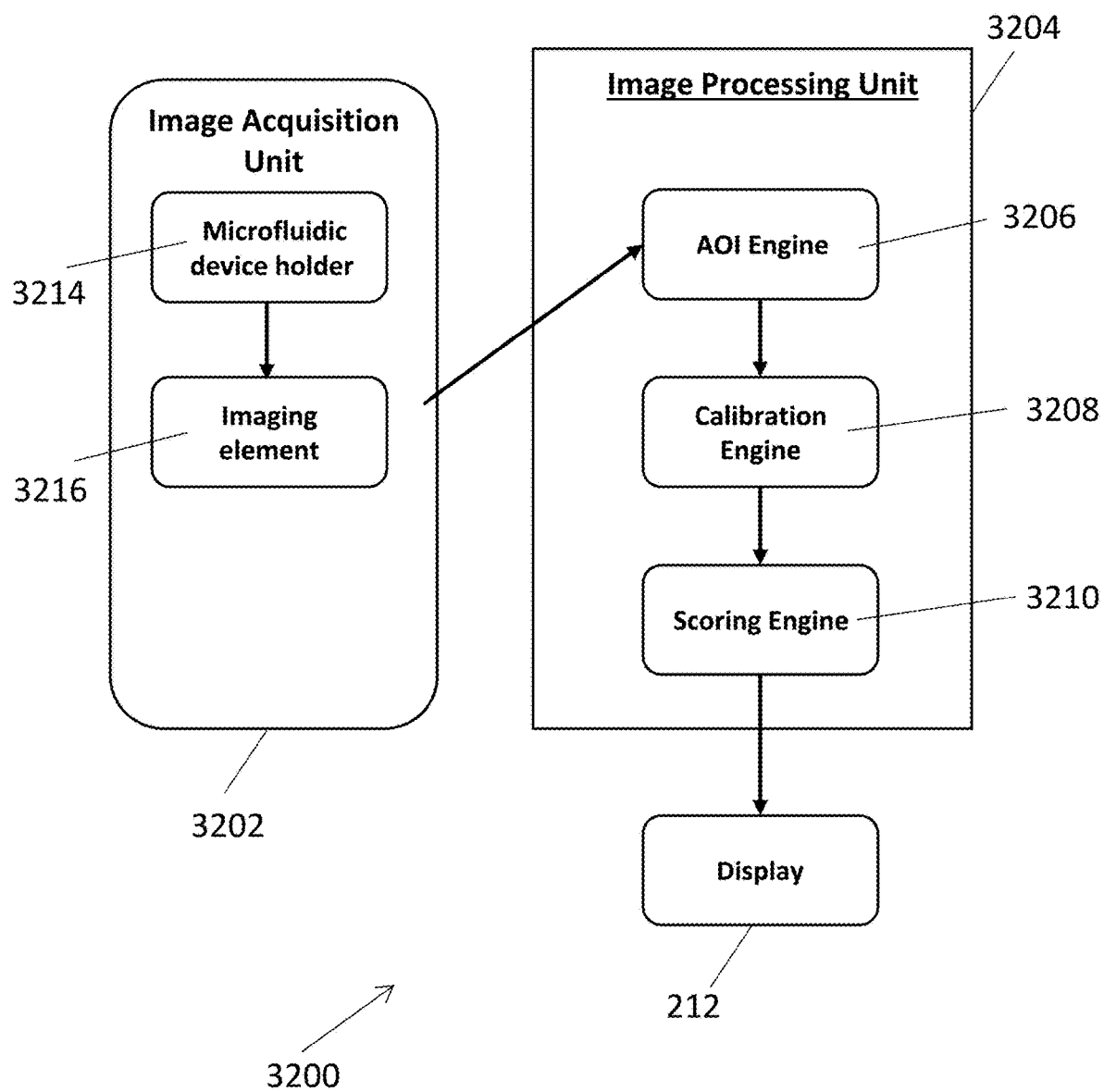
FIG. 26 is a schematic diagram of a system for assessing a quantity of analyte, in accordance with various embodiments

FIG. 26 is a schematic diagram of a system for determining a quantity of analyte produced by a micro-object, in accordance with various embodiments. As depicted herein, the system 3200 can include an image acquisition unit 3202, an image processing unit 3204, and a display 3212 for outputting data and receiving user input via an associated input device (not pictured).

Image acquisition unit 3202 (such as, but not limited to, imaging module 164 depicted in FIG. 1 above) can include a microfluidic device holder 3214 (such as, but not limited to, support structure 104 and 300 depicted in FIGS. 1 and 3B above) and an imaging element 3216 (such as, but not limited to, imaging device 194 referenced above).

Microfluidic device holder 3214 can be oriented and designed to secure a microfluidic device. The microfluidic device can include any of the various examples described herein (such as, but not limited to, microfluidic device 200, 230, 250, 280, 290, 320, 400, 500, 900, 1000, 1100 and 1200 depicted in FIGS. 1B-1C, 2A-2B, 2D, 2G-2H, 3A, 4A-4C, 5A-5C, 9B, 10B, 11A-11B and 12A-12B above). Alternatively, holder 3214 can integrated with the microfluidic device. The microfluidic device can include a flow region and a chamber, or plurality of chambers, which can be fluidically connected to the flow region, wherein each of the chambers can hold one or more micro-objects. As previously noted, the chambers can be, for example, sequestration pens. It should be appreciated that the chambers can be of on any shape, size or orientation as required by the particular application that they are used for. As discussed previously, the flow region can be a single microfluidic channel, or a plurality of microfluidic flow channels (such as, but not limited to, channel 122 as depicted in FIGS. 1A and 2A-2C above, and flow channels 264 as depicted in FIGS. 2D-2F above), which provide a single flow path or a plurality of flow paths (such as, but not limited to, flow path 106 depicted in FIGS. 1A and 2B above, and flow of medium 242 and 278 and depicted in FIGS. 2C-2D, 4A-4C, 5A, 9B, 10B, 12A above). The flow region can be in fluid communication with a single, or a plurality of chambers. Alternatively, the flow region may be in fluid communication with the single chamber, or a plurality of chambers, via a reversible closure such as, for example, a valve. The flow region can be configured to receive a flow of material via an inlet as previously described. The flow of material can include, for example, a flow of micro-objects, binding agent or reagents, or a flow of medium including the material. The microfluidic device can further be configured to receive a flow of a binding agent (such as, for example, a reporter molecule) through the flow path and into the chambers. The binding agent may emit electromagnetic radiation, such as light emitted by a detectable label of the binding agent (e.g., fluorescence, UV, etc.), upon binding to the analyte. The analyte can include, for example secretions from the micro-object, where the micro-object can be a biological micro-object. The analyte can include, for example, a protein, a saccharide, a nucleic acid, antibody, antigen, an organic molecule other than a protein, saccharide or nucleic acid, a vesicle, or a virus.

Imaging element 216 can be configured to capture one or more assay images 3222 (see FIG. 27) of the plurality of chambers and the flow region of the microfluidic device. Imaging element 3216 can further be configured to capture one or more corresponding background images 3218 (see FIG. 27) and/or one or more corresponding signal reference images 3220 (see FIG. 3) to be analyzed and implemented in conjunction with the one or more assay images 3222 as discussed in detail below.

The background image 3218 can be taken by imaging element 3216 prior to any foreign matter (such as, for example, micro-objects, binding agent, or other reagents) being introduced into the microfluidic device. In so doing, the background image 3218 captures any background noise in the device, particularly in an area of interest, further discussed below. Background noise can be due to, for example, artifacts, or instrument setup and imaging parameters—for example, light from the excitation source, camera noise, and ambient light. Background noise can also be due to background fluorescence imparted by, for example, auto-fluorescence of samples, vessels, imaging media, or the fluorescence resulting from fluorophores not bound to specific targets. What image area is included in the background image depends on how that image is implemented on the system going forward. For example, as will be described in detail below, depending on the calibration methods used, a different background image area may be desired.

The signal reference image 3220 can be taken by imaging element 3216 after a binding agent is introduced into the chambers to a level such that the binding agent concentration equilibrates in the area of interest ("AOI"). In so doing, the signal reference image 3220 captures image acquisition distortions in the device. Such distortions can stem from, for example, microfluidic or imaging element design. Image distortion types can include, for example, image edge effects, perspective distortion, barrel distortion, pincushion distortion, mustache distortion, and chromatic aberration. The signal reference image area can include an image of the AOI, the flow region proximate the chamber and associated AOI, or both. What image area is included in the signal reference image depends on how that image is implemented by the system going forward. For example, as provided in further detail below, depending on the calibration methods implemented by the system, a different signal reference image area may be utilized.

Image processing unit 3204 of system 3200 of FIG. 26 can be communicatively connected to the image acquisition unit 3202. In various embodiments, image processing unit 3204 can include an area of interest determination engine 3206 and a scoring engine 3210. It should be appreciated that each component (e.g., engine, module, etc.) depicted as part of image processing unit 3204 (and described herein) can be implemented as hardware, firmware, software, or any combination thereof.

In various embodiments, the image processing unit 3204 can be implemented as an integrated instrument system assembly with the image acquisition unit 3202. That is, the image processing unit 3204 and image acquisition unit 3202 can be housed in the same housing assembly and communicate via conventional device/component connection means (e.g. serial bus, optical cabling, electrical cabling, etc.).

In various embodiments, image processing unit 3204 can be implemented as a standalone computing device (as shown above in FIG. 25) that is communicatively connected to the image acquisition unit 3202 via an optical, serial port, network or modem connection. For example, the image processing unit can be connected via a LAN or WAN connection that allows for the transmission of imaging data acquired by the image acquisition unit 3202 to the image processing unit 3204 of analysis.

In various embodiments, the functions of image processing unit 3204 can be implemented on a distributed network of shared computer processing resources (such as a cloud computing network) that is communicatively connected to the image acquisition unit 3202 via a WAN (or equivalent) connection. For example, the functionalities of image processing unit 3204 can be divided up to be implemented in one or more computing nodes on a cloud processing service such as AMAZON WEB SERVICES™.

The area of interest determination engine 3206 can be designed and configured to receive the captured assay image from imaging element 3216 and define an AOI for each chamber depicted in the assay image. The area of interest determination engine 3206 can be programmed to define an appropriate AOI by including, within the AOI, an image area within the chamber that is most sensitive for measuring analyte concentration fluctuations. For example, this would be an area within the chamber where the smallest fluctuations in electromagnetic radiation, such as light emissions (e.g., fluorescence, UV, etc.), can be measured by the imaging element 3216. Even further, the image area can include an image area that is least sensitive to the position of micro-objects in the chamber when analyte fluctuations are measured. For example, this would be an area within the chamber where the sensitivity of measurements of electromagnetic radiation, such as light emissions (e.g., fluorescence, UV, etc.), is least affected by the presence of micro-objects in the chamber. The AOI can even further be defined to extend along an axis of diffusion 3302 (see FIG. 28), between the respective chamber and the flow region in fluid communication with the respective chamber.

Figure 28:
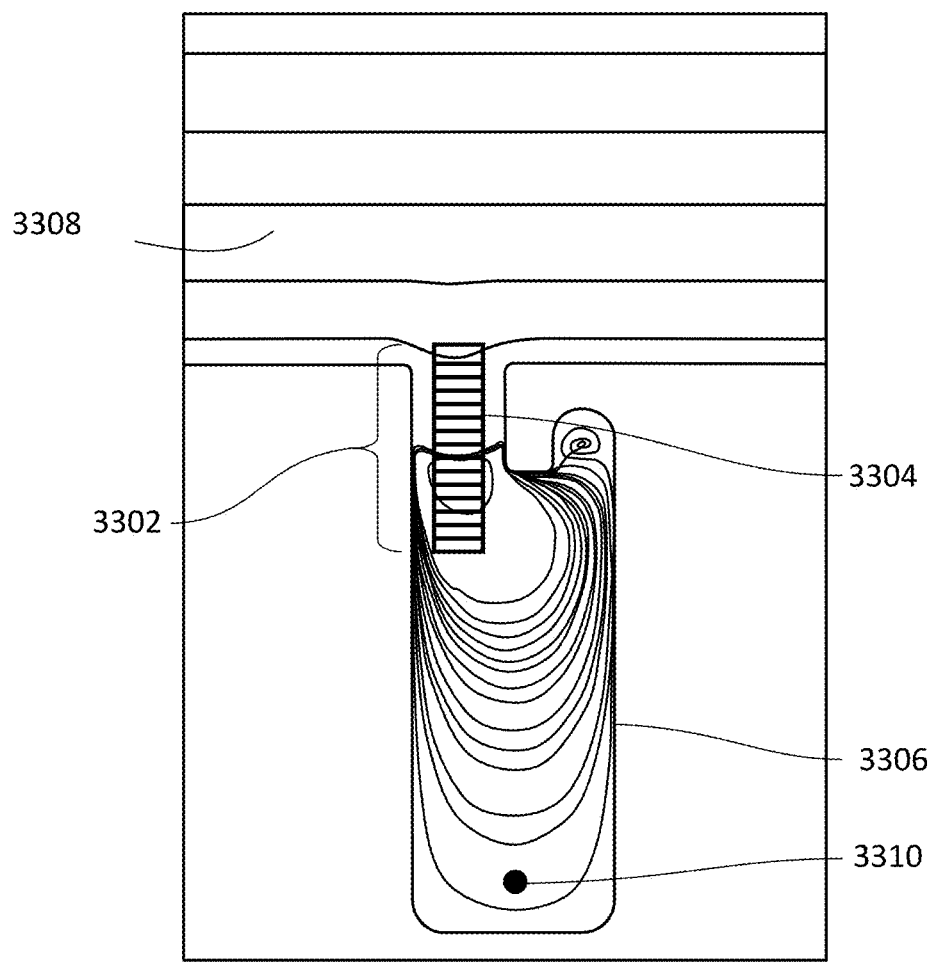
FIG. 28 is a cross-section of a chamber of a micro-fluidic device, in accordance with various embodiments.

In an exemplary embodiment depicted in FIG. 28, axis of diffusion 3302 can be determined using spatial information about the microfluidic device and its corresponding chambers. That spatial information can be derived from a CAD model contained in system 3200, associated software, or separate software package to produce a defined unaligned AOI 3224. Calibration algorithms for the imaging element and microfluidic device can then map the image data to this CAD model to obtain the appropriate axis of diffusion 3302. Applying a spatial correction transform 3226 based from this mapping, area of interest determination engine 3206 can produce a set of aligned AOIs 3228. The AOI can be determined automatically from the area of interest determination engine 3206 or can be determined manually via user input into display 3212.

Scoring engine 3210 of system 3200 of FIG. 26 can be designed and configured to analyze at least a portion of the image area within the area of interest of each chamber to determine scores that are indicative of the quantity of analyte in each chamber. Moreover, since the score can be a dimensionless value that can be compared by scoring engine 3210 to other scores to indicate a relative quantity, or concentration of analyte, the score determined can be converted into units of concentration for the user.

To determine a score, scoring engine 3210 can use various models. Some models, as discussed below, can be those that utilize, for example, fluorescence data that quantifies the amount of binding agent (such as, for example, a reporter molecule) that binds to the analyte in each chamber, the flow region, or both. The analyte can include, for example, secretions from the micro-object within a chamber, where the micro-object can be a biological micro-object. Scoring engine 3210 can use the bound reporter molecule data (such as, for example, fluorescence values), particularly across an AOI, to determine a score for a respective chamber, which is indicative of the quantity of analyte in that chamber. Non-limiting examples of scoring models include applying linear regression analysis to light emission data (e.g., fluorescence values or some other type of detectable signal) over a portion of the image area of the AOI of each chamber, applying a sigmoidal model to the AOI, using average intensity of the AOI that is invariant to the position of the biological micro-objects emitting the analyte of interest, or integrating light emission data (e.g., fluorescence values or some other type of detectable signal) over a portion of the image area of the AOI of each chamber.

Sigmoidal modeling, for example, approximates the diffusion gradient in the AOI by sigmoid, or logistic, curves, equations and details. A quantitation model using a combination of parameters, such as, for example, growth rate, difference between asymptotes, and the inflection point location, may yield the necessary accuracy and/or precision. The model's parameters could be estimated, for example, by nonlinear regression or curvilinear regression depending on the exact form of the sigmoid curve used. Common model parameter estimation techniques include, for example, Levenberg-Marquardt, simplex, and simulated annealing. Heuristic techniques can be used to initialize the parameters to further assist in ensuring convergence during iterative fitting techniques such as nonlinear regression. For example, upper and lower asymptotes can be crudely estimated by the averages of sub-regions at the extremes of the AOI.

Figure 27:
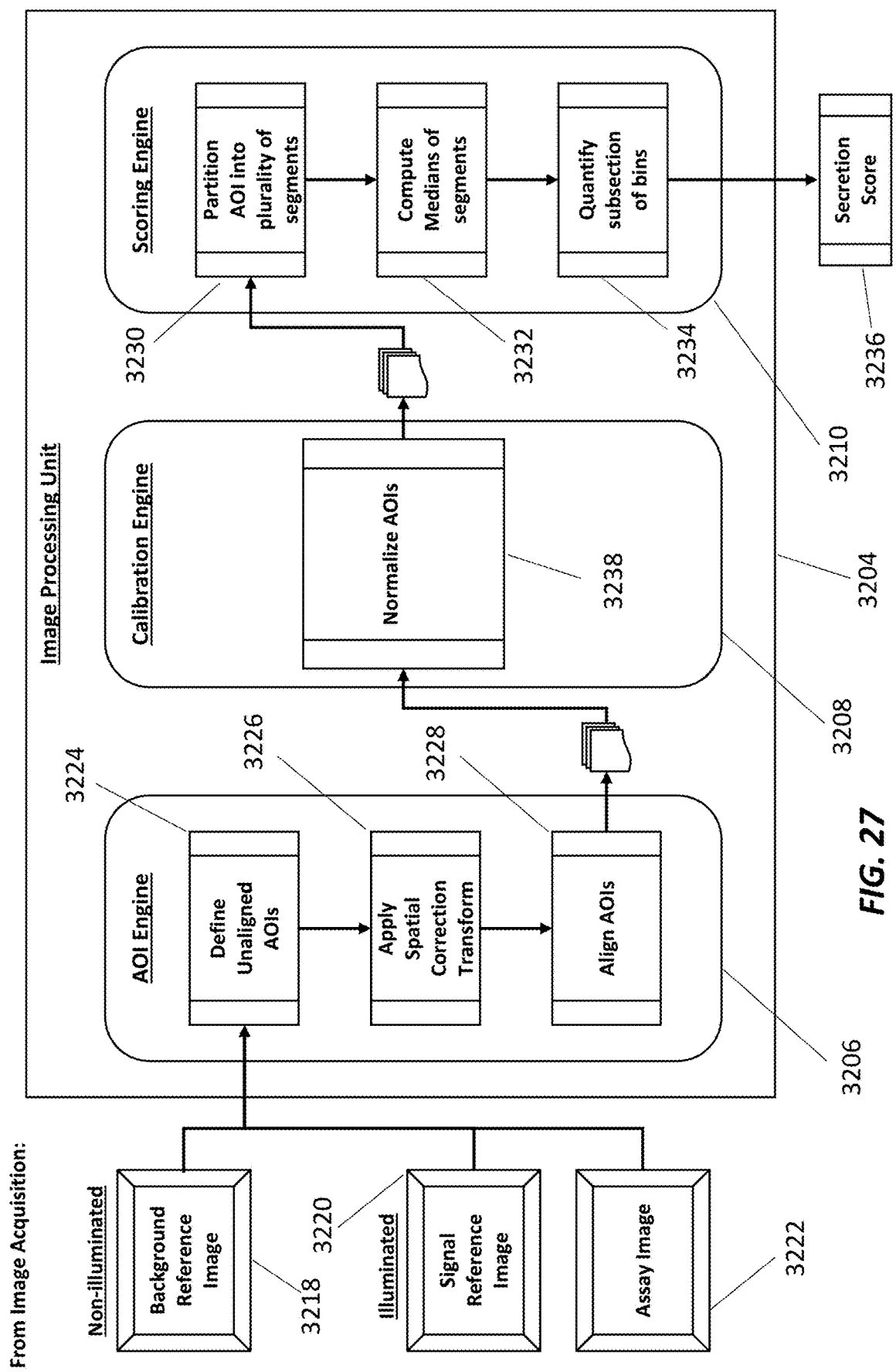
FIG. 27 is a schematic diagram of a system for assessing a quantity of analyte, in accordance with various embodiments.

Alternatively, as depicted in the embodiment of FIG. 27, prior to applying the above scoring models over an AOI, scoring engine 3210 can partition the aligned AOI 3228 into separate segments 3230 along the axis of diffusion 3302 (see FIG. 28). FIG. 4 depicts an example of a portion of a microfluidic device, including a flow region 3308, chamber 3306, axis of diffusion 3302, a plurality of segments 3304 and a micro-object 3310. The number of segments 3304 can vary as needed to perform the requisite scoring model. The number of segments 3304 can be, for example, 20. For segments 3304, scoring engine 3210 can compute a median value 3232, wherein the value can be, for example, electromagnetic radiation values, such as fluorescent values, indicative of amount of binding agent (such as, for example, reporter molecule) that binds to analyte within each chamber 3306, the flow region 3308, or both. The analyte may include, for example, secretions from the micro-object 3310, where the micro-object can be a biological micro-object. The scoring engine 3210 can then determine a subset of segments 3304 via a subsection quantification process 3234 based on a set of parameters.

The scoring engine 3210 can determine a subset of segments 3304 via a subsection quantification process 3234 using a set of instructions encoded into, or provided remotely to (for example, wirelessly, remote software program, user input), the scoring engine 3210. The set of instructions can be based on, for example, previous numerical simulations conducted using different combinations of, for example, micro-object types, micro-object counts in a chamber, segment counts, subsection counts and subsection locations. Using this data, instructions can be encoded that associate the micro-object of interest with the various numerical simulations to determine the appropriate subset of segments for the analysis of the biological micro-object of interest.

The subset of segments 3304 can include any group of segments within the total segment count necessary to determine a score for said chamber 3306. For example, based on the provided set of parameters or instructions, the scoring engine 3210 could identify bins 9-13 as the subset of bins used in determining the score for a specific chamber. Applying scoring models, such as those described previously, the scoring engine 3210 can then determine a score, such as a secretion score 3236, for said chamber.

Alternatively, image processing unit 3204 can further include a calibration engine 3208 as depicted in the embodiment of FIG. 26 and the embodiment of FIG. 27. Calibration engine 3208 can be designed and configured to apply an AOI normalization process 3238 of each chamber for image distortions caused by background noise from the microfluidic device and during assay image capture. The resulting calibrated image AOI can then be scored by scoring engine 3210. As stated above, background noise can be due to, for example, artifacts, or instrument setup and imaging parameters—for example, light from the excitation source, camera noise, and ambient light. Background noise can also be due to background fluorescence imparted by, for example, autofluorescence of samples, vessels, imaging media, or the fluorescence resulting from fluorophores not bound to specific targets. Image distortions during assay image capture can stem from, for example, microfluidic device design or imaging device design. Image distortion types can include, for example, image edge effects, projector non-uniformity, camera vignette, perspective distortion, barrel distortion, pincushion distortion, mustache distortion, and chromatic aberration.

Calibration engine 3208 can be designed and configured to normalize the AOI of each chamber, or at least the image area of the AOI of each chamber, for image distortions from the microfluidic device before and/or introduced during assay image capture. Calibration engine 3208 can accomplish this by subtracting the background image from the assay image and/or signal reference image, and accounting for image acquisition distortions captured in the signal reference image. The resulting normalized image AOI can then be scored by scoring engine 3210.

Various models exist for normalizing an image for feature extraction and anomaly detection. In an embodiment, data exclusion via statistical inference can remove anomalies prior to normalizing the AOI. Anomalies such as foreign material, which may have very low or very high intensities, can be detected with basic statistical transformations such as computing the z-score of a given data point within the distribution of all AOI data.

In an embodiment, data exclusion via statistical inference can remove anomalies prior to normalizing the AOI. Because an ideal diffusion profile generally has a constant value along any line orthogonal to the axis of diffusion, it is possible to statistically infer whether anomalies, such as foreign material, exist in the AOI and to exclude those data points from modeling. Each data point in the AOI can be transformed into a z-score, which is indicative of its probability of occurrence due to random variation. For example, given an AOI where I is an intensity value at a given point, $\mu$ is the mean intensity value, $\sigma$ is the standard deviation, y denotes the direction of diffusion and x is orthogonal to it, a z-score at a given point can be calculated via equation (1):

$$z_{x,y} = \frac{I_{x,y} - \mu_y}{\sigma_y} \quad (1)$$

The z-scores produced by the equation above can be used to exclude data with z-score magnitudes greater than a given threshold. This process can be repeated to iteratively remove anomalies of different sizes and intensities.

In an embodiment, piecewise modeling can remove anomalies prior to normalizing the AOI. Based upon the principle that the diffusion profile is ideally constant along any direction orthogonal to the axis of diffusion, one can fit an analytical model independently across the N columns of the AOI. In an ideal system, these models would all yield the same parameter estimates. In practice, they will be normally distributed. However, in the case of anomalies, such as misalignment or the presence of foreign material, there will be additional modalities in the distribution of parameter estimates. By combining information such as the correlation of the models to the AOI-column's data with the prevalence of a given parameter's magnitude within the distribution of all parameter estimates, one may determine which models reflect an abnormal result and thus should be excluded from further analysis. This may be used in conjunction with the z-score technique described above to appropriately normalize the data of interest.

In an embodiment, normalized values for the assay image ($I_{Corrected}$) at a point x,y can be produced captured using background image "a" and signal reference image "c" data, according to equation (2):

$$I_{Corrected}(x, y) = \frac{I(x, y) - a(x, y)}{c(x, y) - a(x, y)} \quad (2)$$

In an embodiment, a G score is produced to normalize all data points in an AOI. After capturing a background image "a" and signal reference image "c", a correcting factor, "G", can be calculated according to equation (3):

$$G(x, y) = \frac{(\bar{c} - \bar{a})}{(c(x, y) - a(x, y))} \quad (3)$$

The correcting factor G can then be applied as follows to determine normalized values for the assay image ($I_{corrected}$) according to equation (4) for scoring of the AOI:

$$I_{Corrected}(x,y) = G(x,y)(I_{Original}(x,y) - a(x,y)) \quad (4)$$

Using normalized values for the assay image, scoring engine 3210 can be further designed and configured to analyze a portion of the normalized area of interest of each chamber to determine scores that are indicative of the quantity of analyte in each chamber. As discussed in detail above, examples of scoring models include applying linear regression analysis to a portion of the normalized area of interest of each chamber, or integrating fluorescence values (or some other type of detectable signal) over a portion of the normalized area of interest of each chamber.

Alternatively, rather than using a signal reference image and a background image of the AOI, calibration engine 3208 may apply the above embodiments for calibration using a signal reference image and/or background image of the flow region proximate the chamber(s) and associated AOI(s), as well as other areas of the microfluidic device that do not contain biological micro-objects. These "non-AOI" images can be used in conjunction with assay image data to normalize the assay image data as discussed in detail above.

In accordance with various embodiments, image acquisition unit 3202 and image processing unit 3204 can be integrated into a single physical unit. Alternatively, image acquisition unit 3202 and image processing unit 3204 can be separably oriented, provided in independent units such that units are still communicatively connected to exchange information.

Each component of image processing unit 3204 described above may be hardware or may partially or entirely be a software module.

Figure 29:
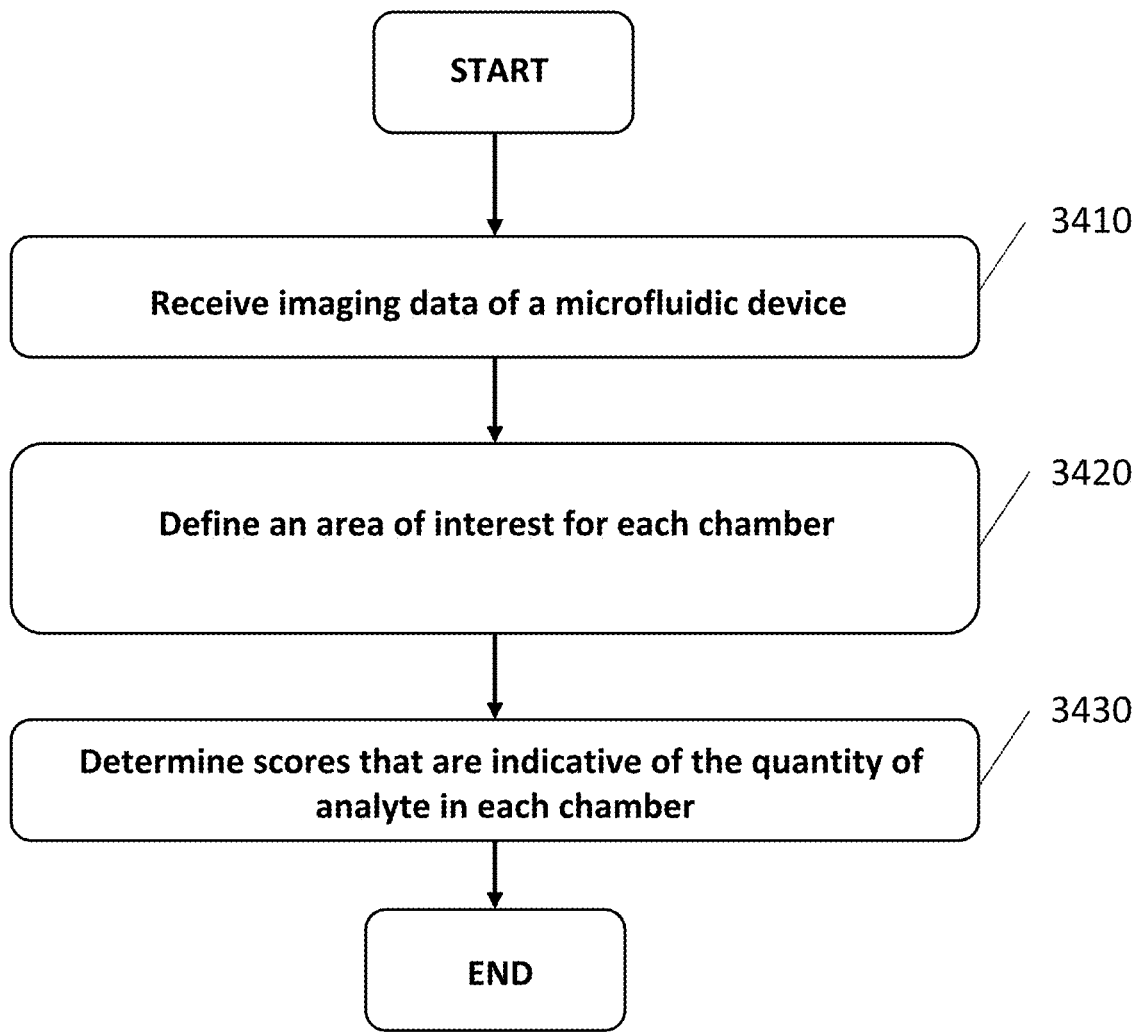
FIGS. 29 and 30 are exemplary flowcharts depicting a method for determining a quantity of analyte, in accordance with various embodiments.

FIG. 29 is an exemplary flowchart showing a method for predicting determining a quantity of analyte produced by a micro-object. As depicted herein, step 3410 details an exemplary workflow that can be utilized by area of interest engine 3206 of image acquisition unit 3202 of system 3200 of FIG. 26. In step 3410, area of interest engine 3206 receives imaging data of a microfluidic device that includes a flow region and a plurality of chambers that are fluidically connected to the flow region, wherein the imaging data includes a background noise image, a signal reference image and an analyte assay image. The background image can be taken by imaging element 3216 prior to any foreign matter (such as, for example, micro-objects, binding agent, or other reagents) being introduced into the microfluidic device. In so doing, the background image captures any background noise associated with system 3200 and image captures of areas on the device. Examples of background noise are described previously. The signal reference image can be taken by imaging element 3216 after binding agent is introduced into the chambers to a level such that the binding agent concentration equilibrates in the device. In so doing, the signal reference image captures image acquisition distortions associated with system 3200 and associated image captures of areas on the device.

The received imaging data can include, for example, fluorescence emission data determined from fluorescence emitted from the binding agent (such as, for example, a reporter molecule) binding to an analyte in the one or more chambers, flow region, or both. The analyte can include, for example, secretions from the micro-objects, where the micro-objects can be biological micro-objects. Secretions from the biological micro-objects can include, for example, a protein, a saccharide, a nucleic acid, an organic molecule having a molecular weight of less than 3 Kd, or a virus. As previously noted, the chambers can be, for example, sequestration pens.

As depicted herein, steps 3420 and 3430 detail an exemplary workflow that can be utilized by scoring engine 3210 of image processing unit 3204 of system 3200 of FIG. 26. In step 3420, image processing unit 3204 can define an area of interest ("AOI") for each chamber. The AOI can include an image area within the chamber that is most sensitive for measuring analyte concentration fluctuations. The AOI can further include an image area that is least sensitive to the position of micro-objects in the chamber when analyte fluctuations are measured and, even further, the image area can extend along an axis of diffusion between the chamber and the flow region.

In step 3430, scoring engine 3210 can determine scores that are indicative of the quantity of analyte in each chamber by analyzing a portion of the AOI for each chamber. To determine a score per chamber, scoring engine 3210 can use various models as discussed above. Some models can be those that utilize, for example, fluorescence data that quantify the amount of binding agent (such as, for example, a reporter molecule) that binds to an analyte. The analyte can include, for example, secretions from the micro-object within a chamber, where the micro-object can be a biological micro-object. Scoring engine 3210 can use the bound reporter molecule data (or fluorescence values), particularly across an AOI, to determine a score for a respective chamber, which is indicative of the quantity of analyte in that chamber. Non-limiting examples of scoring models include applying linear regression analysis to a portion of the normalized area of interest of each chamber, or integrating fluorescence values (or some other type of detectable signal) over a portion of the normalized area of interest of each chamber.

Figure 30:
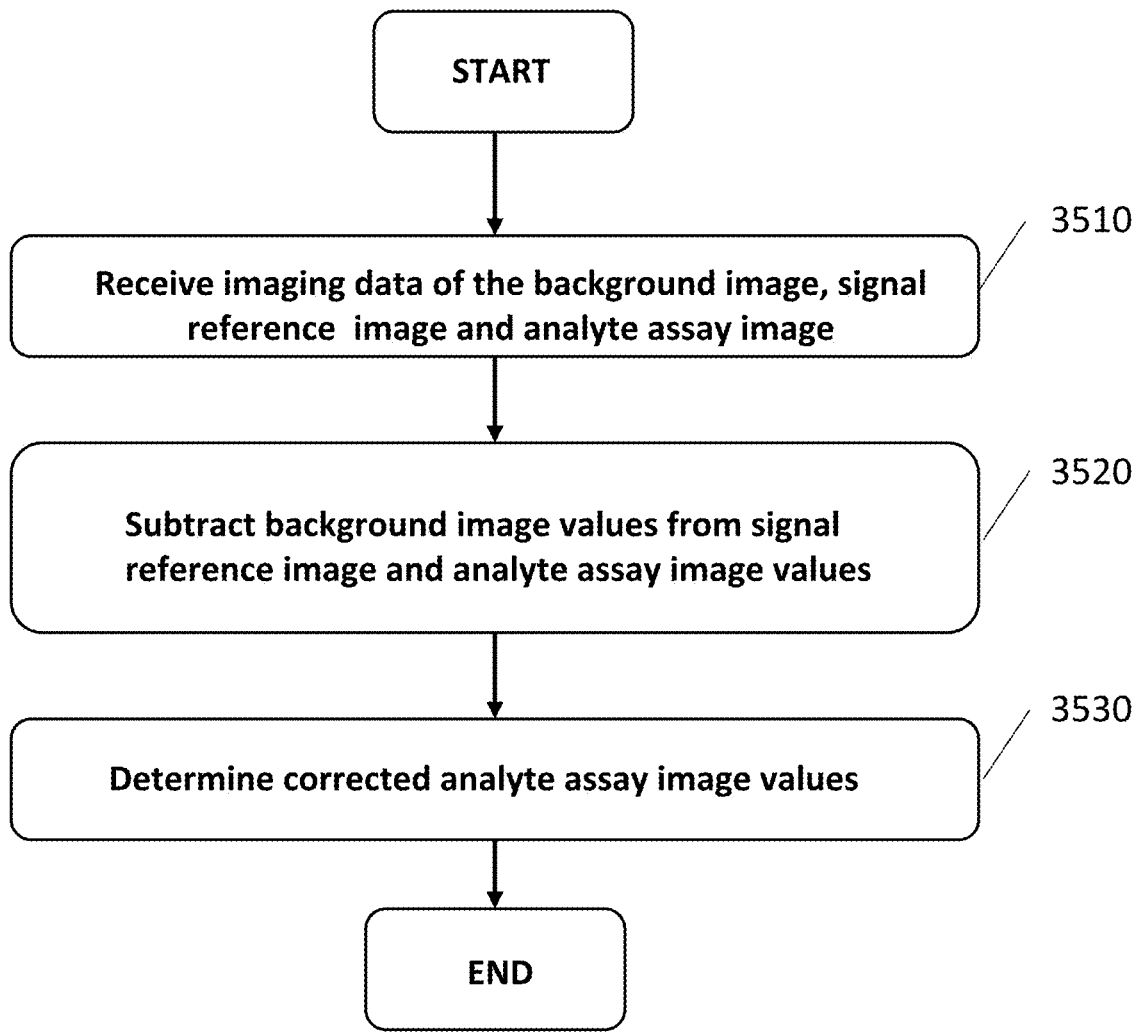

FIG. 30 illustrates a calibration method that can be applied to imaging data to obtain a normalized AOI for each of the chambers in the analyte assay image. As depicted herein, steps 3510 through 3530 detail an exemplary workflow for the calibration method that can be utilized by calibration engine 3208 of image processing unit 3204 of FIG. 26.

In step 3510, calibration engine 3208 can receive imaging data from the image acquisition unit 3202, which can include imaging data of the background image, signal reference image and analyte assay image. As discussed previously, imaging data can be in the form of fluorescence values from an area of interest per chamber on a microfluidic device. The imaged fluorescence can be that which originates from background noise (for the background image), from binding agent that fills the area of interest (for the signal reference image, or from emissions by the binding agent (such as, for example, a reporter molecule) that binds to analyte that may include, for example, secretions from the biological micro-object present in a chamber.

In step 3520, calibration engine 3208 can subtract background image values from signal reference image and analyte assay image values. In so doing, any background noise already present in the system is removed from the signal reference image and analyte assay image values to obtain background corrected values for both images no longer affected by the noise.

In step 3530, calibration engine 3208 can further correct the analyte assay image values by comparing background corrected values of the signal reference image and analyte assay image values to account for image acquisition distortions, previously described, that would be identified though the signal reference image. The comparison would produce normalized analyte assay image values, particularly within the AOI. Examples of associated formulas and calculations to determine the normalized values are provided above.

Using the normalized data, scoring engine 3210 can determine scores that are indicative of the quantity of analyte in each chamber by analyzing a portion of the now normalized AOI for each chamber.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 3100 of FIG. 1, whereby processor 3104 would execute the analyses and determinations provided by these engines, subject to instructions provided by any one of, or a combination of, memory components 3106/3108/3110 and user input provided via input device 3114.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical, FLASH memory and non-optical data storage devices. The computer readable medium can also be distributed over a network coupled computer systems so that the computer readable code is stored and executed in a distributed fashion.

EXPERIMENTAL

System and device: An OptoSelect™ device, a nanofluidic device manufactured by Berkeley Lights, Inc. and controlled by an optical instrument which was also manufactured by Berkeley Lights, Inc. were employed. The instrument includes: a mounting stage for the chip coupled to a temperature controller; a pump and fluid medium conditioning component; and an optical train including a camera and a structured light source suitable for activating phototransistors within the chip. The OptoSelect device includes a substrate configured with OptoElectroPositioning (OEP™) technology, which provides a phototransistor-activated OET force. The chip also included a plurality of microfluidic channels, each having a plurality of NanoPen™ chambers (or sequestration pens) fluidically connected thereto. The volume of each sequestration pen is around $1 \times 10^6$ cubic microns.

Biological cells. CHO cells engineered to express a human antibody were used. Cell numbers and viability were counted and cell density was adjusted to $5 \times 10^5$/ml for loading the cells onto the OptoSelect device.

Device priming. 250 microliters of 100% carbon dioxide is flowed in to the OptoSelect device at a rate of 12 microliters/sec, followed by 250 microliters of PBS containing 0.1% Pluronic® F27 (Life Technologies® Cat #P6866) flowed in at 12 microliters/sec, and finally 250 microliters of PBS flowed in at 12 microliters/sec. Introduction of the culture medium follows.

Media: CD CHO medium (ThermoFisher Scientific Cat. #10743029), a commercially available protein-free and serum-free medium, chemically defined medium was used.

Media perfusion during culture. Medium is perfused through the OptoSelect device according to either of the following two methods:
1. Perfuse at 0.01 microliters/sec for 2 h; perfuse at 2 microliters/sec for 64 sec; and repeat.
2. Perfuse at 0.02 microliters/sec for 100 sec; stop flow 500 sec; perfuse at 2 microliters/sec for 64 sec; and repeat.

Example 1: Assessing the Relative Production of an Antibody Using a Peptide Reporter Molecule Reporter molecule. An IgG binding peptide having a molecular weight of 2.4 Kd, N-terminally labeled with HiLyte Fluor™ 555 NHS ester (AnaSpec Inc., Cat. #AS-81251, 869 da (MW of free acid), Ex/Em 550/566 nm (Cy3 filter)).

Dark Reference image collection: Prior to introduction of cells, the OptoSelect device was imaged first with no medium nor reporter molecule present, obtaining the Dark Reference image used in a process as described herein which removes background and normalizes the image of each NanoPen chamber.

Signal Reference image collection: Culture medium containing the N-terminally labeled HiLyte Fluor™ 555 IgG binding peptide (reporter molecule) at a concentration of 1 microgram/ml was flowed into the OptoSelect device for 45 min at 0.005 microliters/sec until the fluorescent compound diffused and achieved an equilibrated distribution between the NanoPen chambers and the microfluidic channel. The Signal Reference image was acquired at that time. The OptoSelect device was then flushed with culture medium at 0.03 microliters/sec having no reporter molecule for 25 min. This period of flushing ensured that the reporter molecules had substantially completely diffused out of the NanoPen chamber, leaving none or insignificant amounts of reporter molecules remaining within the NanoPen chambers. The Signal Reference image may alternatively be obtained by flowing the fluorescent dye itself at the same molar concentration, and does not require that fluorescently labeled reporter molecule be employed.

Introducing secreting cells into the microfluidic device. CHO cells were introduced into the OptoSelect device and selectively placed into the Nanopen chambers using dielectrophoretic forces of the OEP technology of the device. The cells were disposed one cell per NanoPen chamber. Culture medium was perfused as above, for a period of 6 days. Brightfield images were taken daily to record cell expansion within each NanoPen chamber. The selection of a 6 day culture period prior to a first assay may be varied depending on the particular requirements of the biological cells and secreted analyte. It may be desired to assay (which may include a brightfield image) each day of an extended culture period, or one or more assays may be performed on selected days during the culturing period.

Assay Signal Collection. As an initial step of the assay, a brightfield image was obtained to correlate cell number and position within each NanoPen chamber. After collection of the brightfield image, the fluorescent reporter molecule at a concentration of 1 microgram/ml was flowed into the microfluidic channel 0.05 microliters/sec for a period of 45 min, affording sufficient time for reporter molecule to diffuse fully into each NanoPen chamber. After introduction of the reporter molecule to the NanoPen chamber, flow of culture medium containing no fluorescent reporter molecule was resumed at 0.03 microliters/sec for a period of 25 minutes, based on the diffusion rate as determined above. A fluorescence image was obtained. The assay may be repeated if desired, over additional periods of culturing/expansion as determined to be suitable for the particular cells and/or secreted analyte therefrom.

Determination of relative production of analyte. An area of interest (AOI) along the axis of diffusion from within the NanoPen chamber was identified within each Nanopen chamber which encompasses an area of about 20 pixels wide and 200 pixels in length, where the lower (first) end of the AOI was chosen to be within the isolation region at a selected distance from the base of the NanoPen chamber distal to the opening into the microfluidic channel, where no cells were disposed. The second (upper end) of the length of the AOI was selected to be within the microfluidic channel itself, which ensured that the pixels residing within the AOI and within the channel substantially have no signal. The width of the AOI is centered along a trajectory of anticipated diffusion from the isolation region of the NanoPen chamber out to the channel of the OptoSelect Device. As described herein, the AOI was sub-divided into 20 sub-regions (bins), each having a width of 20 pixels and a length along the anticipated diffusion trajectory of 10 pixels.

The fluorescent Assay image was normalized/calibrated as described herein using the Dark Reference and the Signal Reference images to reduce system errors, and roll off of signal image due to imperfect illumination of the field of view. Each pixel in the AOI is processed as:

$$\text{Normalized Assay value} = \frac{\text{Assay intensity value} - \text{Dark Reference}}{\text{Signal Reference value} - \text{Dark Reference}}$$

The median intensity for each of the 20 sub-regions was determined by adding the signal intensities for each pixel in the sub-region. A representation of the curve resulting from plotting the normalized median intensity values for each sub-region, is shown in FIG. 12B, where the x axis lists sub-regions 1 to 20. Sub-region 1 is the sub-region of the AOI most distal from the channel, and sub-region 20 is the sub-region of the AOI that is furthest into the channel. A linear regression was performed upon the section of the curve plotting the normalized median intensity values for sub-regions 9-13 (region 1156, in FIG. 12B). As described above, these sub-regions were determined to be within the region where the signal intensity observed was insensitive to the position of the biological cells within the lower (most distal from the channel) portion of the isolation region of the NanoPen chamber. The value of the slope obtained from this operation was used as a score, in arbitrary units (A.U.). Larger slopes (score) indicated greater secretion of analyte by the cells within that NanoPen chamber.

Figure 21:
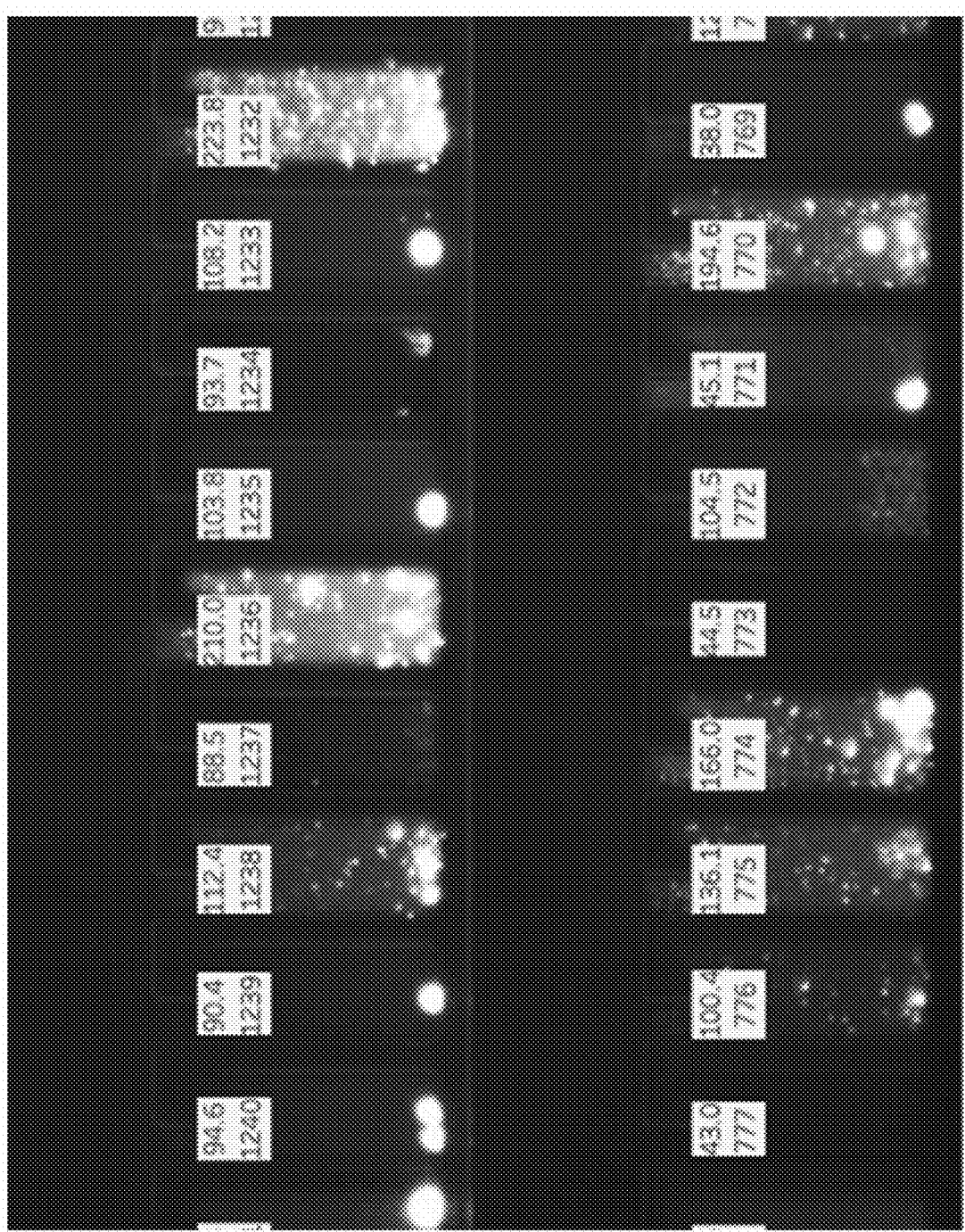
FIG. 21 is a photographic representation of a normalized assay image of a portion of microfluidic device including pen identification and assay scores according to some embodiments of the disclosure.
Figure 22:
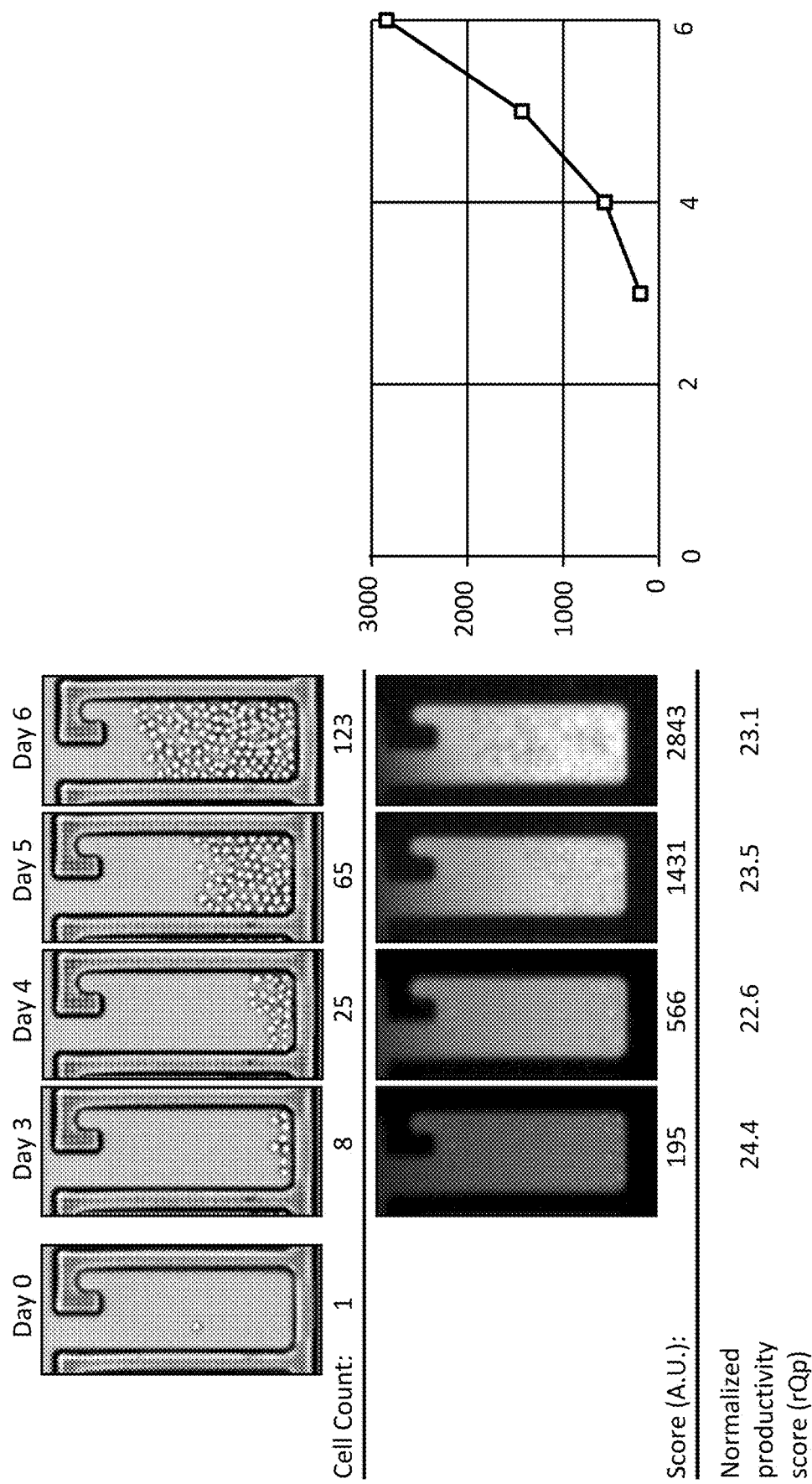
FIG. 22 is a photographic and a graphical representation of a course of a culturing and assay sequence according to some embodiments of the disclosure.

As shown in FIG. 21, an identification number and a score is indicated for each of the NanoPen chambers visible (top number is the identification number for that NanoPen chamber, and the lower number is the score for that NanoPen chamber) clearly correlated with the intensity of signal observed. Nanopen chambers 563 and 941, with low scores of 10.01 and 8.67 respectively, had at least one cell producing analyte, but with low amounts of reporter molecule: antibody complex diffusing out of each of these NanoPen chambers. NanoPen chambers 563 and 949, with scores of 13.15 and 17.26 respectively, showed mid-range scores. Finally, NanoPen chambers 560, 566, and 942, having scores of 25.26, 29.99 and 27.95 respectively, produced greater amounts of the antibody analyte. The scores shown here are not corrected for the number of cells present. However, that calculation may be imposed on the scores shown here. Either raw scores or cell-count-corrected scores may be used to more easily rank NanoPen chambers to assist in deciding on which NanoPen chambers to be further examined in the course of the effort to develop highly productive cell lines. Other methods of calculating a rate of concentration change from within the NanoPen chamber to the channel may also be employed such as area under the curve or other methods described herein to quantify the level of production of secreted analyte within each NanoPen chamber.

Measure of relative productivity. Scores may be corrected for the number of cells per NanoPen chamber, as shown in FIGS. 22A-B. In this experiment, the cell type, media, reporter molecule, pre-culturing image acquisition, culturing conditions, and assay conditions were the same as above. FIG. 22A shows a single NanoPen chamber 2124 for which a brightfield image was acquired at day 0, and on days 3,4, 5, 6, as shown in the images in the top row of FIG. 21. Additionally, an assay as described above was performed on each of days 3, 4, 5, 6 and the fluorescent images for each of days 3, 4, 5, and 6 for the same single NanoPen chamber 2124 are shown aligned under the corresponding brightfield image for that day. The brightfield image was used to count the number of cells present, which may be performed in an automated process, showing for the selected NanoPen chamber: day 0 (1 cell); day 3 (8 cells); day 4 (25 cells); day 5 (65 cells); day 6 (123 cells), as the clonal population expanded. The assay scores, obtained as described above (representing the negative slope) steadily increased, as well, day 3 (195 A.U.); day 4 (566 A.U.); day 5 (1431 A.U.); day 6 (2842). Accordingly, on day 3, eight cells in the NanoPen chamber resulted in a score of 195 (A.U.). On day 4, the same NanoPen chamber now had 25 cells, resulting in a score of 566 (A.U.). On day 5, the same NanoPen chamber had 65 cells, resulting in a score of 1431 (A.U.). Finally, on day 6, the same NanoPen chamber had 123 cells, resulting in a score of 2843 (A.U.). The graph of FIG. 22B shows the assay scores (y-axis) plotted against the assay timepoint in days (x-axis) since the start of cell culture within the NanoPen chamber. The absolute scores were divided by the number of cells present at that timepoint to provide a score normalized to the number of cells in the chamber. This yielded a normalized measure of productivity (rQp) of cells in the selected NanoPen chamber, which remained in a range between 22.6 to 24.1 A.U. per cell.

Figure 23A:
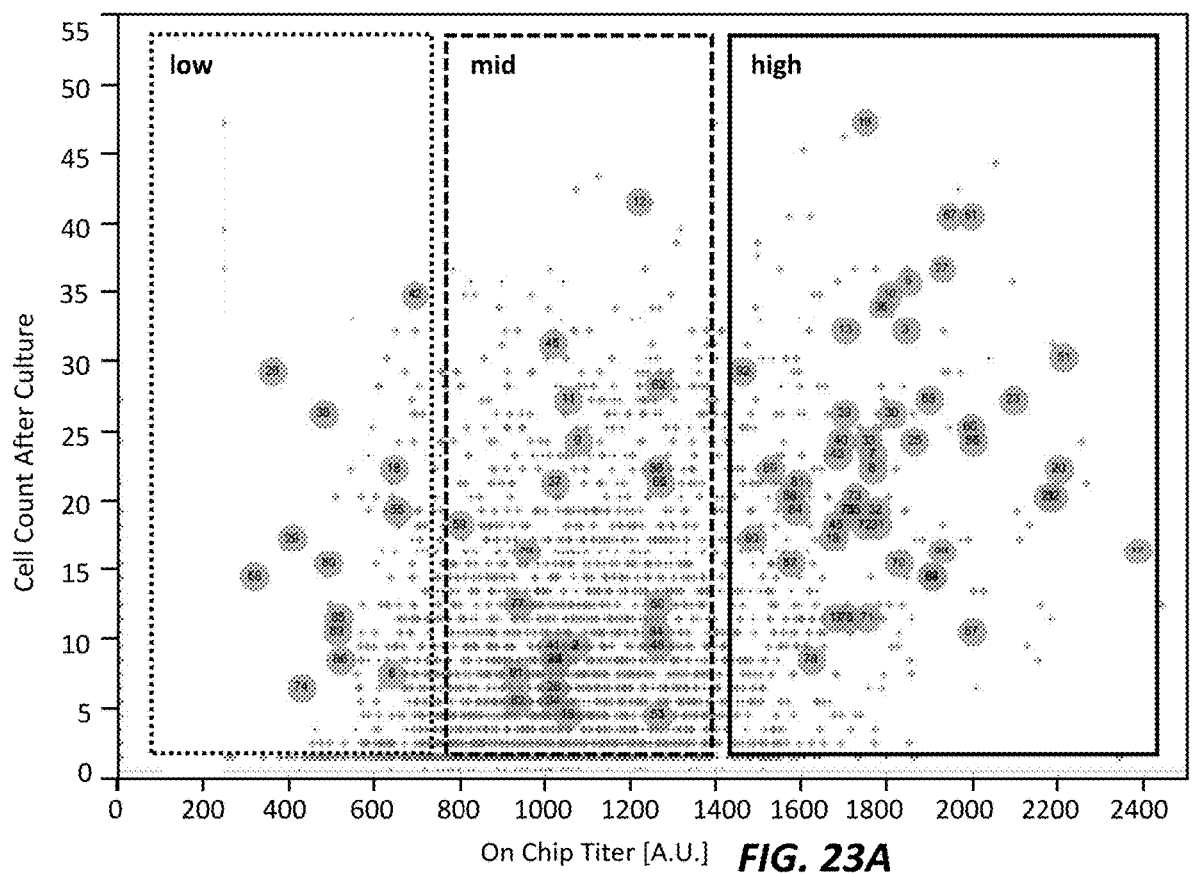
FIGS. 23A-23B are graphical representation of assay values for all the chambers of a microfluidic device according to some embodiments of the disclosure.

Example 2. Correlation of the In-Situ Scoring of Antibody Production with Macroscale Production and Cell Line Development System and device: as above.
Cells: CHO cells as in Experiment 1.
Media: as in Experiment 1.
Reporter molecule: as in Experiment 1.
Culturing was performed for 6 days, and the diffusion based assay using a HiLyte Fluor™ 555 labeled IgG binding peptide having a molecular weight of 2.4 Kd was performed as in Experiment 1. Analysis to assign a score based on the intensities of signal observed within the AOI as defined herein was performed. Scores were assessed for each Nanopen chamber within the OptoSelect device. In FIGS. 22A and 22B, each NanoPen chamber of the OptoSelect device was plotted, where the horizontal axis is the titer obtained on chip (the "score", or in this case, the slope of the median intensity values along the cell position insensitive sub-region (sub-regions 9-13 of 1-20 for the entire AOI)). Each NanoPen chamber was plotted on the y-axis of the graph (FIG. 23A) representing the number of cells counted in the respective NanoPen chamber at the time of assay (obtained from the brightfield image). A first selection was made by selecting three groups of NanoPen chambers having: low (cutoff less than 800 A.U.) scores for secretion of analyte; mid-levels scores for analyte secretion (from just less than 800 A.U. to about 1400 A.U.) and high scores for analyte secretion (from about 1400 to about 2400 A.U.). Within each of these selected groups, there were NanoPen chambers having large, medium and low numbers of cells.

Figure 23B:
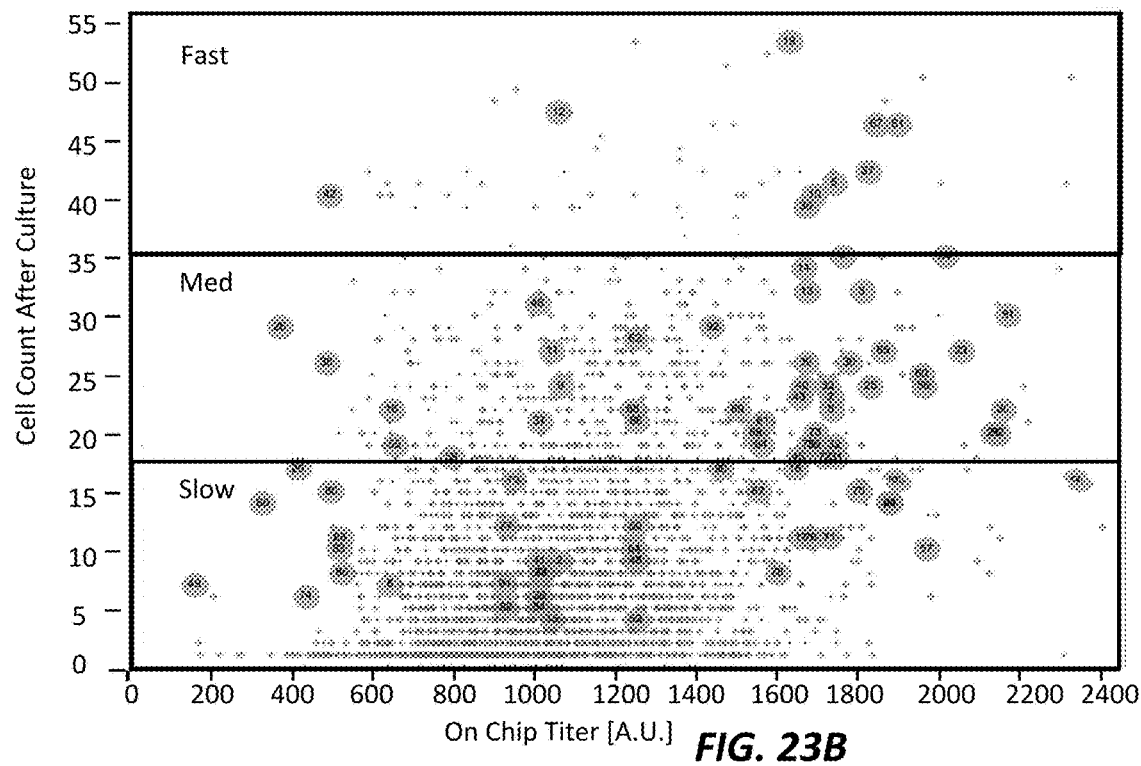

A further selection was included, as shown in FIG. 23B, to select NanoPen chambers having fast growth; chambers showing a medium rate of cell doubling, and a third group was selected to have only slowly expanding numbers of cells. In each of these groups, there were representatives of high, medium and low levels of analyte production (scores range across the entire horizontal axis of FIG. 23B. Selection of individual NanoPen chambers within in one of all nine sub-types of growth/secretion profiles was made and the selected pens (each holding a separate clonal population) was exported individually, first to well plates. Titers were obtained via an ELISA assay to IgG. A further selection of low, medium and highly secreting wells containing clonal populations were introduced to 125 ml shaker flasks and scaled up further.

Figure 16B:
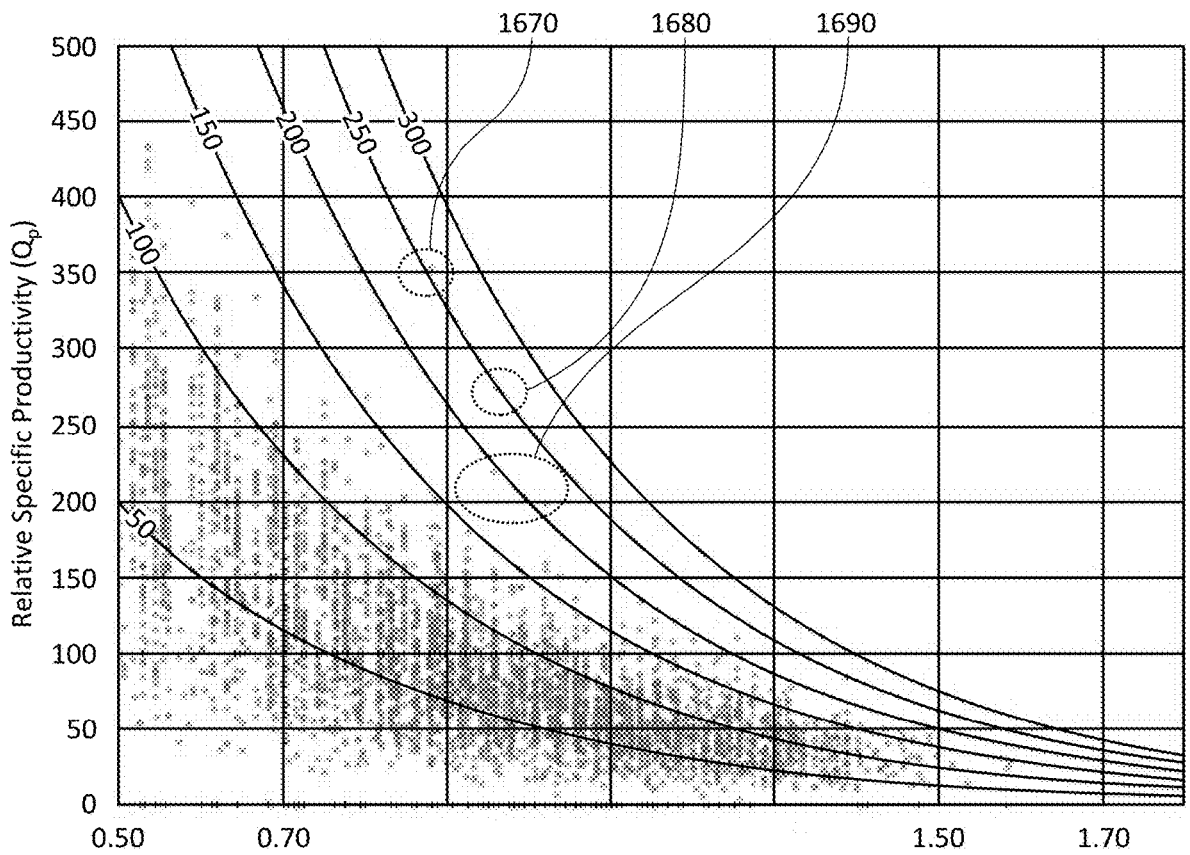
Figure 24:
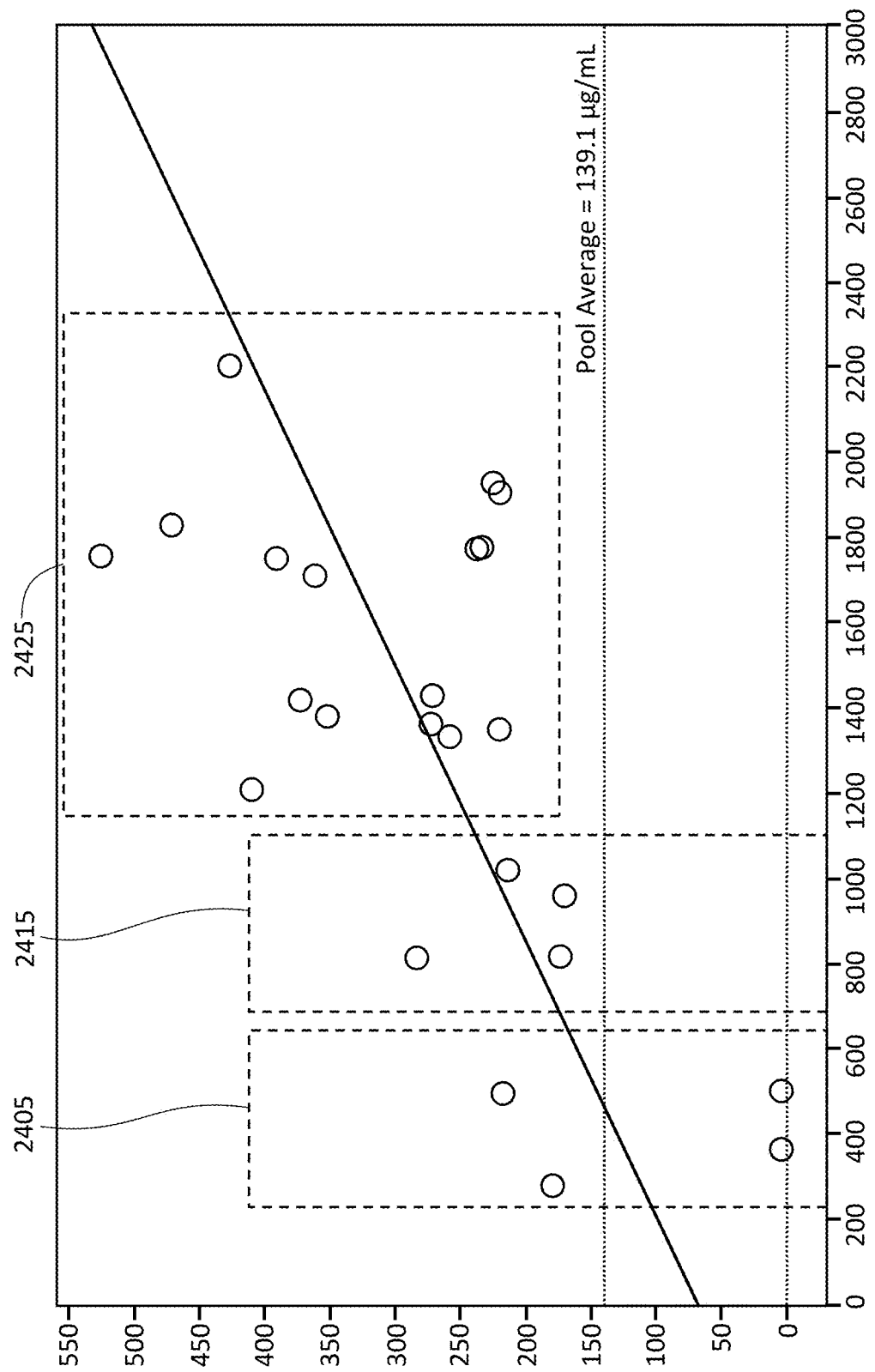
FIG. 24 is a graphical representation of correlation between assay values for clonal populations in selected chambers of a microfluidic device and the respective scaled up clonal population according to some embodiments of the disclosure.

The clonal populations in the scaled up 125 ml shaker flasks were assayed via ELISA assay for IgG. Selected clones are shown in FIG. 24, where the titer of each 125 ml shaker flask is represented on the y-axis and the on chip titer (score in A. U. as obtained in the assay described above) for the respective NanoPen chamber from which the cells originated, is shown on the x-axis. A first group 2405 originated from cells within Nanopen chambers having low on-chip titers (scores). Group 2405 did not include any high producing clones once scaled to 125 ml shaker flask. A second group 2415 originated from cells within Nanopen chambers having a medium range of on-chip titer (score) and demonstrated a mid range of ELISA titer values from the 125 shaker flask. The last group 2425, has high titer values, all being higher than the pool average of 139.1 micrograms/mL, and correlate back to cells from NanoPen chambers having on-chip titers (score in A.U.) that also were high. It was therefore demonstrated that for cells in NanoPen chambers having medium to high on chip titers (scores, or, in a particular embodiment, a slope) there is good correlation to the level of titer obtained in the macroscale population. Therefore, the assay performed within an OptoSelect device as described herein yielded a meaningful approach to more rapidly identify greater numbers of highly productive clones for cell line development. Additionally, as discussed above with regard to FIG. 16B, the ability to screen each clonal population individually affords the ability to identify productive clones that may not grow as rapidly as other non-productive clonal populations. These slower growing, more productive clones would have low probability of being identified under condition of bulk expansion.

Example 3. Assessing the Relative Production of an Antibody Using an Aptamer

System and device: as above.
Cells: CHO cells as in Experiment 1.
Media: as in Experiment 1.
Reporter molecule: Aptamer for human immunoglobulin G, (Apta-Index™, Apt 8, ID #44, a 23-mer, MW. 7.4 Kd, affinity for the Fc domain, Aptagen L.L.C. Sequence: 5'-rGp-rGp-rAp-rGp-rGp-fUp-rGp-fCp-fUp-fCp-fCp-rGp-rAp-rAp-rAp-rGp-rGp-rAp-rAp-fCp-fUp-fCp-fCp-3'. In the sequence notation, a r- prefix indicates a ribonucleotide; f- prefix indicates a 2-Fluoro nucleotide; -p suffix indicates phosphate; and G, A, C, U are standard nucleotide abbreviations. It is labeled with Alexa Fluor® 594 (AF594, ThermoFisher Scientific, Cat. No. A20004 (NHS ester)) MW 819.8, Ex/Em590/617 nm).

Culture medium containing either Alexa Fluor® 594 or Alexa Fluor 594 labelled aptamer at a concentration of 2 micrograms/ml is flowed into the OptoSelect device for 45 min until the fluorescent compound diffuses and achieves an equilibrated distribution between the NanoPen chambers and the microfluidic channel. The Signal Reference image is acquired. The OptoSelect device is then flushed with culture medium having no reporter molecule for 30 min at 0.03 microliters/sec. This period of flushing ensures that the reporter molecules substantially completely diffuse out of the NanoPen chamber.

CHO cells are introduced into the OptoSelect device and selectively placed into the Nanopen chambers using dielectrophoretic forces of the OEP technology of the device. The cells are disposed one cell per NanoPen chamber. Culture medium is perfused as above, for a period of 6 days. Brightfield images are taken daily to record cell expansion within each NanoPen chamber. Assays to detect antibody production are performed each day of day 3, 4, 5 and 6 of the experiment.

Assay Signal Collection. A brightfield image is obtained to correlate cell number and position within each NanoPen chamber. After collection of the brightfield image, fluorescent reporter molecule, Aptamer—AlexaFluor 594, at a concentration of 2 microgram/ml is flowed into the microfluidic channel for a period of 50 min, affording sufficient time for reporter molecule to diffuse fully into each NanoPen chamber. After introduction of the reporter molecule to the NanoPen chamber, flow of culture medium containing no reporter molecule is resumed at 0.03 microliters/sec for a period of 30 minutes, based on the diffusion rate for a molecule of approximately 7 Kd. A fluorescence image is obtained.

An area of interest (AOI) along the axis of diffusion from within the NanoPen chamber is identified within each Nanopen chamber which encompasses an area of about 20 pixels wide and 200 pixels in length, situated as described above in Experiment 1. The width of the AOI is centered along a trajectory of anticipated diffusion from the isolation region of the NanoPen chamber out to the channel of the OptoSelect Device. The AOI is sub-divided into 20 sub-regions (bins or segments), each having a width of 20 pixels and a length along the anticipated diffusion trajectory of 10 pixels. The fluorescent Assay image is normalized/calibrated as described herein using the Dark Reference and the Signal Reference images to reduce system errors, and roll off of signal image due to imperfect illumination of the field of view.

The median intensity for each of the 20 sub-regions is determined by adding the signal intensities for each pixel in the sub-region. A curve of the normalized median intensity values for each sub-region, is generated and a linear regression is performed upon the section of the curve plotting the normalized median intensity values for sub-regions 9-13. The value of the slope obtained from this operation is used as a score, in arbitrary units (A.U.). It is expected that a select number of individual NanoPen chambers of the 3500 total NanoPen chambers of the OptoSelect device have scores greater than 200-250 A.U. and are selected to be exported for expansion and further development.

Although specific embodiments and applications of the disclosure have been described in this specification, these embodiments and applications are exemplary only, and many variations are possible.

RECITATION OF SELECTED EMBODIMENTS

Embodiment 1. A system for determining a quantity of analyte produced by a biological micro-object, comprising: an image acquisition unit, comprising: a microfluidic device holder capable of securing a microfluidic device, wherein the microfluidic device includes a flow region and a plurality of sequestration pens that are fluidically connected to the flow region, wherein each of the plurality of sequestration pens can hold one or more biological micro-objects, and an imaging element configured to capture one or more assay images of the plurality of sequestration pens and the flow region of the microfluidic device; and an image processing unit communicatively connected to the image acquisition unit, comprising: an area of interest determination engine configured to receive each captured assay image and define an area of interest for each sequestration pen depicted in the assay image, wherein the area of interest includes an image area corresponding to an area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region, and a scoring engine configured to analyze at least a portion of the image area within the area of interest of each sequestration pen, to determine scores that are indicative of the quantity of analyte in each sequestration pen.

Embodiment 2. The system of Embodiment 1, further comprising: a calibration engine configured to normalize at least the image area of the area of interest of each sequestration pen for image distortions caused by background noise and/or introduced during assay image capture.

Embodiment 3. The system of Embodiment 1 or 2, wherein the imaging element is further configured to capture one or more corresponding background images and one or more corresponding signal reference images.

Embodiment 4. The system of Embodiment 3, wherein the calibration engine is configured to normalize at least the image area of the area of interest of each sequestration pen for image distortions by subtracting the corresponding background image from the assay image; and/or wherein the calibration engine is configured to normalize at least the image area of the area of interest of each sequestration pen for image distortions by accounting for image acquisition distortions captured in the corresponding signal reference image.

Embodiment 5. The system of any one of Embodiments 2-4, wherein the scoring engine is configured to analyze at least a portion of the normalized image area of the area of interest of each sequestration pen to determine scores that are indicative of the quantity of analyte in each sequestration pen.

Embodiment 6. The system of Embodiment 5, wherein the scoring engine is configured to apply a linear regression analysis to light intensity values over a portion of the normalized image area of the area of interest of each sequestration pen to determine scores that are indicative of the quantity of analyte in each sequestration pen.

Embodiment 7. The system of Embodiment 5, wherein the scoring engine is configured to integrate light intensity values over a portion of the normalized area of interest of each sequestration pen to determine scores that are indicative of the quantity of analyte in each sequestration pen.

Embodiment 8. The system of any one of Embodiments 1 to 7, wherein the image acquisition unit and the image processing unit are separately oriented.

Embodiment 9. The system of any one of Embodiments 1 to 7, wherein the image acquisition unit and the image processing unit are integrated into a single unit.

Embodiment 10. The system of any one of Embodiments 1 to 9, wherein the area of interest is automatically defined by the image processing unit.

Embodiment 11. The system of any one of Embodiments 1 to 10, wherein the microfluidic device is configured to receive a flow of a binding agent that binds to analyte produced by the biological micro-objects and comprises a detectable label, and wherein the scoring engine is configured to determine analyte quantity in each sequestration pen based on an amount of light emitted by the detectable label of the binding agent, as determined from the assay image.

Embodiment 12. A method for determining a quantity of analyte produced by a biological micro-object, comprising: receiving imaging data of a microfluidic device that includes a flow region and a plurality of sequestration pens that are fluidically connected to the flow region, wherein the imaging data includes an analyte assay image and one or both of a background noise image and a signal reference image; defining an area of interest for each sequestration pen, wherein the area of interest includes an image area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region, and determining scores that are indicative of the quantity of analyte in each sequestration pen by analyzing at least a portion of the image area of the area of interest for each sequestration pen.

Embodiment 13. The method of Embodiment 12, wherein the imaging data comprises light emission data determined from light emitted from a reporter molecule that binds to the analyte produced by the biological micro-objects.

Embodiment 14. The method of Embodiment 12 or 13, further comprising: normalizing at least the image area of the area of interest for each of the sequestration pens in the analyte assay image by subtracting out background noise captured in the background noise image; and/or normalizing at least the image area of the area of interest for each of the sequestration pens in the analyte assay image by accounting for image acquisition distortions captured in the signal reference image.

Embodiment 15. The method of Embodiments 14, wherein determining scores that are indicative of the quantity of analyte in each sequestration pen further comprises analyzing at least a portion of the normalized image area of the area of interest for each sequestration pen.

Embodiment 16. The method of Embodiments 14, wherein determining scores that are indicative of the quantity of analyte in each sequestration pen further comprises applying a linear regression analysis to light emission data over at least a portion of the normalized image area of the area of interest of each sequestration pen.

Embodiment 17. The method of Embodiments 14, wherein determining scores that are indicative of the quantity of analyte in each sequestration pen further comprises integrating light emission data over at least a portion of the normalized image area of the area of interest of each sequestration pen.

Embodiment 18. The method of any one of Embodiments 12 to 17, wherein the analyte comprises a protein, a saccharide, a nucleic acid, an organic molecule other than a protein, saccharide or nucleic acid, a vesicle, or a virus.

Embodiment 19. A non-transitory computer-readable medium in which a program is stored for causing a computer to perform an image processing method for determining a quantity of analyte produced by a biological micro-object, the method comprising: receiving imaging data of a microfluidic device that includes a flow region and a plurality of sequestration pens that are fluidically connected to the flow region, wherein the imaging data includes an analyte assay image and one or both of a background noise image and a signal reference image; defining an area of interest for each sequestration pen, wherein the area of interest includes an image area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region, and determining scores that are indicative of the quantity of analyte in each sequestration pen by analyzing at least a portion of the image area of the area of interest for each sequestration pen.

Embodiment 20. The method of Embodiment 19, wherein the imaging data comprises light emission data determined from light emitted from a reporter molecule that binds to from the analyte produced by the biological micro-objects.

Embodiment 21. The method of Embodiment 19 or 20, further comprising: normalizing at least the image area of the area of interest for each of the sequestration pens in the analyte assay image by subtracting out background noise captured in the background noise image; and/or normalizing at least the image area of the area of interest for each of the sequestration pens in the analyte assay image by accounting for image acquisition distortions captured in the signal reference image.

Embodiment 22. The method of Embodiments 21, wherein determining scores that are indicative of the quantity of analyte in each sequestration pen further comprises analyzing at least a portion of the normalized image area of the area of interest for each sequestration pen.

Embodiment 23. The method of Embodiments 21, wherein determining scores that are indicative of the quantity of analyte in each sequestration pen further comprises applying a linear regression analysis to the light emission data from at least a portion of the normalized image area of the area of interest of each sequestration pen.

Embodiment 24. The method of Embodiments 21, wherein determining scores that are indicative of the quantity of analyte in each sequestration pen further comprises integrating light emission data over at least a portion of the normalized image area of the area of interest of each sequestration pen.

Embodiment 25. The method of any one of Embodiments 19 to 24, wherein the analyte comprises a protein, a saccharide, a nucleic acid, an organic molecule other than a protein, saccharide or nucleic acid, a vesicle, or a virus.

Embodiment 26. A method of assessing a level of secretion of an analyte by a biological micro-object, or a population of biological micro-objects generated therefrom, the method comprising: introducing the biological micro-object into a sequestration pen of a microfluidic device, wherein the microfluidic device comprises an enclosure having a flow region, wherein the sequestration pen is fluidically connected to the flow region, and wherein the sequestration pen contains a first fluidic medium; allowing the biological micro-object, or the population of biological micro-objects generated therefrom, to secrete an analyte into the first fluidic medium within the sequestration pen; introducing a second fluidic medium into the flow region for a first period of time, wherein the second fluidic medium comprises a plurality of reporter molecules, and wherein each reporter molecule comprises a binding component configured to bind the secreted analyte and a detectable label; allowing a portion of the plurality of reporter molecules to diffuse into the sequestration pen and bind to the analyte secreted therein, thereby producing a plurality of reporter molecule: secreted analyte (RMSA) complexes; and detecting reporter molecules located within an area of interest within the microfluidic device, wherein the area of interest includes at least a portion of the sequestration pen.

Embodiment 27. The method of embodiment 26, wherein the detectable label comprises a visible, luminescent, phosphorescent, or fluorescent label.

Embodiment 28. The method of embodiment 27, wherein the detectable label of the reporter molecules is a fluorescent label, and wherein said detecting the reporter molecules comprises detecting fluorescence emission from the fluorescent label of the reporter molecules within the area of interest.

Embodiment 29. The method of embodiment 26 or 27 further comprising: exposing, for a second period of time, a portion of the microfluidic device comprising the sequestration pen to electromagnetic radiation comprising a wavelength which is capable of exciting the fluorescent label of the reporter molecules.

Embodiment 30. The method of embodiment 29, wherein: detecting fluorescence emission within the area of interest is performed after the second period of time; detecting fluorescence emission within the area of interest is performed two or more times during a third period of time; and/or detecting fluorescence emission within the area of interest is performed substantially continuously during a third period of time.

Embodiment 31. The method of embodiment 30 further comprising: exposing, for a fourth period of time, a portion of the microfluidic device comprising at least a portion of the sequestration pen to electromagnetic radiation but not the flow region, wherein the fourth period of time is sufficient to photobleach the fluorescent label of any reporter molecules present in the portion of the sequestration pen; and detecting fluorescence emission within the photobleached portion of the sequestration pen.

Embodiment 32. The method of embodiment 31, wherein: detecting fluorescence emission within the photobleached portion of the sequestration pen is performed after the fourth period of time; detecting fluorescence emission within the photobleached portion of the sequestration pen is performed two or more times during a fifth period of time; and/or detecting fluorescence emission within the photobleached portion of the sequestration pen is performed substantially continuously during a fifth period of time.

Embodiment 33. The method of embodiment 31, wherein detecting fluorescence emission within the photobleached portion of the sequestration pen occurs about 5 seconds to about 20 seconds after said exposing for a fourth period of time (e.g., after reporter molecules comprising non-photobleached fluorescent label have diffused into said sequestration pen).

Embodiment 34. The method of any one of embodiments 31 to 33, wherein the photobleached portion of the sequestration pen is comprised by the area of interest.

Embodiment 35. The method of any one of embodiments 31 to 34, wherein said steps of exposing for a fourth period of time and detecting fluorescence emission in the photobleached portion of the sequestration pen are repeated one or more times (e.g., 1, 2, 3, 4, 5, or more times).

Embodiment 36. The method of any one of embodiments 27 to 35, wherein the sequestration pen has an isolation region and a connection region fluidically connecting the isolation region to the flow region, and wherein the isolation region and the connection region are configured such that components of a fluidic medium in the isolation region are exchanged with components of a fluidic medium in the flow region substantially only by diffusion.

Embodiment 37. The method of any one of embodiments 27 to 36, wherein the biological micro-object is a biological cell, and wherein the method further comprises expanding the biological cell within the sequestration pen into a clonal population of biological cells.

Embodiment 38. The method of any one of embodiments 27 to 37 further comprising perfusing the flow region with a culturing medium, wherein the perfusing occurs after introducing the biological micro-object into the sequestration pen and before introducing the second fluidic medium into the flow region.

Embodiment 39. The method of embodiment 38, wherein the culturing medium comprises one or more of a soluble feeder cell component, a defined dissolved oxygen component, defined pH component, an exhausted growth medium component, and/or a soluble stimulatory component.

Embodiment 40. The method of any one of embodiments 27 to 39, wherein the first period of time is about 30 minutes to about 60 minutes.

Embodiment 41. The method of any one of embodiments 27 to 40, further comprising: introducing a third fluidic medium into the flow region, wherein the third fluidic medium does not comprise any of the reporter molecules; and allowing at least a portion of unbound reporter molecules to diffuse out of the sequestration pen, wherein detecting the reporter molecules located within the area of interest occurs at a time selected such that an amount of unbound reporter molecules that have diffused out of the sequestration pen is at least 2× greater than an amount of RMSA complexes that have diffused out of the sequestration pen.

Embodiment 42. The method of embodiment 41, wherein introducing the third fluidic medium into the flow region comprises flowing the third fluidic medium through the flow region for an additional period of time.

Embodiment 43. The method of embodiment 42, wherein the additional period of time is selected based on modelling of diffusion profiles for unbound reporter molecules and RMSA complexes.

Embodiment 44. The method of embodiment 42, wherein the additional period of time is about 20 minutes to about 50 minutes.

Embodiment 45. The method of any one of embodiments 27 to 44, wherein the area of interest comprises at least a portion of the sequestration pen aligned along an axis of diffusion from within the sequestration pen to out into the flow region.

Embodiment 46. The method of any one of embodiments 27 to 45, wherein detecting the reporter molecules located within the area of interest comprises measuring an intensity of a detectable signal coming from the area of interest, wherein at least some of the detectable signal emanates from the detectable label of reporter molecules located within the area of interest.

Embodiment 47. The method of embodiment 46, wherein detecting the reporter molecules located within the area of interest further comprises determining a background-subtracted signal intensity by subtracting an intensity of a background signal from the measured intensity of the detectable signal.

Embodiment 48. The method of embodiment 46 or 47 further comprising measuring an intensity of a background signal within the area of interest, at a time prior to introducing the biological micro-object into the sequestration pen.

Embodiment 49. The method of any one of embodiments 46 to 48, wherein the measured intensity of the detectable signal or the background-subtracted signal intensity is normalized for a number of cells observed within the sequestration pen.

Embodiment 50. The method of any one of embodiments 27 to 49 further comprising quantifying the level of secretion of the analyte.

Embodiment 51. The method of any one of embodiments 27 to 50 further comprising providing a secretion score for the sequestration pen.

Embodiment 52. The method of embodiment 51, wherein the secretion score is determined according to the method of any one of embodiments 12 to 25.

Embodiment 53. The method of any one of embodiments 27 to 52, wherein the secreted analyte has a molecular weight at least twice as great as a molecular weight of the reporter molecules.

Embodiment 54. The method of any one of embodiments 27 to 52, wherein the secreted analyte has a molecular weight at least four times greater than a molecular weight of the reporter molecules.

Embodiment 55. The method of any one of embodiments 27 to 52, wherein the secreted analyte has a molecular weight at least ten times greater than a molecular weight of the reporter molecule.

Embodiment 56. The method of any one of embodiments 27 to 55, wherein the binding component of the reporter molecule comprises at least one amino acid and/or at least one nucleic acid.

Embodiment 57. The method of any one of embodiments 27 to 55, wherein the binding component of the reporter molecule comprises a peptide or protein.

Embodiment 58. The method of embodiment 57, wherein the binding component of the reporter molecule comprises a peptide having the sequence of any one of SEQ ID NOs: 1 to 10.

Embodiment 59. The method of embodiment 57, wherein the binding component of the reporter molecule comprises protein A, protein G, or an IgG-binding fragment of protein A or protein G.

Embodiment 60. The method of any one of embodiments 27 to 55, wherein the binding component of the reporter molecule comprises an aptamer.

Embodiment 61. The method of any one of embodiments 27 to 60, wherein the analyte secreted by the biological micro-object comprises a protein, a saccharide, a nucleic acid, an organic molecule other than a protein, saccharide, or nucleic acid, a vesicle, or a virus.

Embodiment 62. The method of any one of embodiments 27 to 61, wherein the analyte secreted by the biological micro-object is an antibody or, optionally, a glycosylated antibody.

Embodiment 63. The method of any one of embodiments 27 to 61, wherein the analyte secreted by the biological micro-object is a protein other than an antibody which, optionally, is a glycosylated protein.

Embodiment 64. The method of any one of embodiments 27 to 63, wherein the microfluidic device comprises a plurality of sequestration pens, wherein a biological micro-object is introduced into at least two sequestration pens of the plurality, and wherein the remainder of the method is carried out with respect to each of the at least two sequestration pens.

Embodiment 65. The method of embodiment 64, further comprising comparing a level of secretion for sequestration pens of the at least two sequestration pens of the plurality.

Embodiment 66. The method of embodiment 64, further comprising comparing secretion scores of more than one sequestration pen of the plurality of sequestration pens.

Embodiment 67. The method of any one of embodiments 64 to 66, further comprising: selecting one or more of the at least two sequestration pens; and exporting one or more biological micro-objects from each of the selected sequestration pens.

Embodiment 68. The method of embodiment 67, wherein the one or more biological micro-objects from each of the selected sequestration pens are further exported out of the microfluidic device.

Embodiment 69. The method of embodiment 68, wherein the selected sequestration pens are exported individually.

Embodiment 70. The method of any one of embodiments 27 to 69, wherein the area of interest comprises an image area corresponding to an area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region.

Embodiment 71. The method of embodiment 70, wherein the area of interest consists essentially of the image area.

Embodiment 72. The method of any one of embodiments 28 to 71, wherein the method is automated.

Embodiment 73. A method of assessing a level of secretion of an analyte by a biological micro-object, or a population of biological micro-objects generated therefrom, the method comprising: introducing the biological micro-object into a sequestration pen of a microfluidic device, wherein the microfluidic device comprises an enclosure having a flow region, wherein the sequestration pen is fluidically connected to the flow region, and wherein the sequestration pen contains a first fluidic medium; allowing the biological micro-object, or the population of biological micro-objects generated therefrom, to secrete an analyte comprising an exogenous tag into the first fluidic medium within the sequestration pen; introducing a second fluidic medium into the flow region, wherein the second fluidic medium comprises a plurality of reporter molecules, and wherein each reporter molecule comprises a binding component configured to bind the exogenous tag of the secreted analyte and a detectable label; allowing a portion of the plurality of reporter molecules to diffuse into the sequestration pen and bind to the analyte secreted therein, thereby producing a plurality of reporter molecule: secreted analyte (RMSA) complexes; and detecting reporter molecules located within an area of interest within the microfluidic device, wherein the area of interest includes at least a portion of the sequestration pen.

Embodiment 74. The method of embodiment 73, wherein the sequestration pen has an isolation region and a connection region fluidically connecting the isolation region to the flow region, and wherein the isolation region and the connection region are configured such that components of a fluidic medium in the isolation region are exchanged with components of a fluidic medium in the flow region substantially only by diffusion.

Embodiment 75. The method of embodiment 73 or 74, wherein the biological micro-object is a biological cell, and wherein the method further comprises expanding the biological cell within the sequestration pen into a clonal population of biological cells.

Embodiment 76. The method of any one of embodiments 73 to 75 further comprising perfusing the flow region with a culturing medium, wherein the perfusing occurs after introducing the biological micro-object into the sequestration pen and before introducing the second fluidic medium into the flow region.

Embodiment 77. The method of embodiment 76, wherein the culturing medium comprises one or more of a soluble feeder cell component, a defined dissolved oxygen component, defined pH component, an exhausted growth medium component, and/or a soluble stimulatory component.

Embodiment 78. The method of any one of embodiments 73 to 77, wherein introducing the second fluidic medium into the flow region comprises flowing the second fluidic medium through the flow region for a first period of time.

Embodiment 79. The method of embodiment 78, wherein the first period of time is about 30 minutes to about 60 minutes.

Embodiment 80. The method of any one of embodiments 73 to 79, wherein the detectable label comprises a visible, luminescent, phosphorescent, or fluorescent label.

Embodiment 81. The method of embodiment 80, wherein the detectable label of the reporter molecules is a fluorescent label, and wherein said detecting the reporter molecules comprises detecting fluorescence emission from the fluorescent label of the reporter molecules within the area of interest.

Embodiment 82. The method of embodiment 81 further comprising: exposing, for a second period of time, a portion of the microfluidic device comprising the sequestration pen to electromagnetic radiation comprising a wavelength which is capable of exciting the fluorescent label of the reporter molecules.

Embodiment 83. The method of embodiment 82, wherein: detecting fluorescence emission within the area of interest is performed after the second period of time; detecting fluorescence emission within the area of interest is performed two or more times during a third period of time; and/or detecting fluorescence emission within the area of interest is performed substantially continuously during a third period of time.

Embodiment 84. The method of embodiment 83 further comprising: exposing, for a fourth period of time, a portion of the microfluidic device comprising at least a portion of the sequestration pen to electromagnetic radiation but not the flow region, wherein the fourth period of time is sufficient to photobleach the fluorescent label of any reporter molecules present in the portion of the sequestration pen which, optionally, is comprised by the area of interest; and detecting fluorescence emission within the photobleached portion of the sequestration pen.

Embodiment 85. The method of embodiment 84, wherein: detecting fluorescence emission within the photobleached portion of the sequestration pen is performed after the fourth period of time; detecting fluorescence emission within the photobleached portion of the sequestration pen is performed two or more times during a fifth period of time; and/or detecting fluorescence emission within the photobleached portion of the sequestration pen is performed substantially continuously during a fifth period of time.

Embodiment 86. The method of embodiment 85, wherein said detecting fluorescence emission within the photobleached portion of the sequestration pen occurs about 5 seconds to about 20 seconds after said exposing for a fourth period of time (e.g., after reporter molecules comprising non-photobleached fluorescent label have diffused into said sequestration pen).

Embodiment 87. The method of any one of embodiments 84 to 86, wherein said steps of exposing for a fourth period of time and detecting fluorescence emission within the photobleached portion of the sequestration pen are repeated one or more times (e.g., 1, 2, 3, 4, 5, or more times).

Embodiment 88. The method of any one of embodiments 73 to 87, further comprising: introducing a third fluidic medium into the flow region, wherein the third fluidic medium does not comprise any of the reporter molecules; and allowing at least a portion of unbound reporter molecules to diffuse out of the sequestration pen, wherein detecting the reporter molecules located within the area of interest occurs at a time selected such that an amount of unbound reporter molecules that have diffused out of the sequestration pen is at least 2× greater than an amount of RMSA complexes that have diffused out of the sequestration pen.

Embodiment 89. The method of embodiment 77, wherein introducing the third fluidic medium into the flow region comprises flowing the third fluidic medium through the flow region for an additional period of time.

Embodiment 90. The method of embodiment 89, wherein the additional period of time is selected based on modelling of diffusion profiles for unbound reporter molecules and RMSA complexes.

Embodiment 91. The method of embodiment 89, wherein the additional period of time is about 20 minutes to about 50 minutes.

Embodiment 92. The method of any one of embodiments 73 to 91, wherein the area of interest comprises at least a portion of the sequestration pen aligned along an axis of diffusion from within the sequestration pen to out into the flow region.

Embodiment 93. The method of any one of embodiments 73 to 92, wherein detecting the reporter molecules located within the area of interest comprises measuring an intensity of a detectable signal coming from the area of interest, wherein at least some of the detectable signal emanates from the detectable label of reporter molecules located within the area of interest.

Embodiment 94. The method of embodiment 93, wherein detecting the reporter molecules located within the area of interest further comprises determining a background-subtracted signal intensity by subtracting an intensity of a background signal from the measured intensity of the detectable signal.

Embodiment 95. The method of embodiment 93 or 94 further comprising measuring an intensity of a background signal within the area of interest, at a time prior to introducing the biological micro-object into the sequestration pen.

Embodiment 96. The method of any one of embodiments 93 to 95, wherein the measured intensity of the detectable signal or the background-subtracted signal intensity is normalized for a number of cells observed within the sequestration pen.

Embodiment 97. The method of any one of embodiments 73 to 96 further comprising quantifying the level of secretion of the analyte.

Embodiment 98. The method of any one of embodiments 73 to 97 further comprising providing a secretion score for the sequestration pen.

Embodiment 99. The method of embodiment 98, wherein the secretion score is determined according to the method of any one of embodiments 12 to 25.

Embodiment 100. The method of any one of embodiments 73 to 99, wherein the secreted analyte has a molecular weight at least twice as great as a molecular weight of the reporter molecules.

Embodiment 101. The method of any one of embodiments 73 to 99, wherein the secreted analyte has a molecular weight at least four times greater than a molecular weight of the reporter molecules.

Embodiment 102. The method of any one of embodiments 73 to 99, wherein the secreted analyte has a molecular weight at least ten times greater than a molecular weight of the reporter molecule.

Embodiment 103. The method of any one of embodiments 73 to 102, wherein the exogenous tag of the secreted analyte comprises a peptide sequence.

Embodiment 104. The method of embodiment 103, wherein the peptide sequence comprises a FLAG epitope, a polyhistidine sequence, a hemagglutinin (HA) epitope, or a Myc epitope.

Embodiment 105. The method of embodiment 103, wherein the peptide sequence comprises the amino acid sequence (from N-terminal to C-terminal) DYKDDDDK (SEQ ID NO: 11).

Embodiment 106. The method of embodiment 103, wherein the peptide sequence comprises the amino acid sequence (from N-terminal to C-terminal) HHHHHH (SEQ ID NO: 12).

Embodiment 107. The method of any one of embodiments 103 to 106, wherein the binding component of the reporter molecule comprises a protein.

Embodiment 108. The method of embodiment 107, wherein the protein of the binding component is an antibody.

Embodiment 109. The method of embodiment 108, wherein the antibody recognizes a FLAG epitope.

Embodiment 110. The method of embodiment 106, wherein the binding component of the reporter molecule comprises a chelating agent.

Embodiment 111. The method of embodiment 110, wherein the chelating agent comprising nitrilotriacetic acid (NTA).

Embodiment 112. The method of any one of embodiments 73 to 111, wherein the analyte secreted by the biological micro-object comprises a protein.

Embodiment 113. The method of embodiment 112, wherein the analyte secreted by the biological micro-object is an antibody or, optionally, a glycosylated antibody.

Embodiment 114. The method of embodiment 112, wherein the analyte secreted by the biological micro-object is a protein other than an antibody which, optionally, is a glycosylated protein.

Embodiment 115. The method of any one of embodiments 73 to 114, wherein the microfluidic device comprises a plurality of sequestration pens, wherein a biological micro-object is introduced into at least two sequestration pens of the plurality, and wherein the remainder of the method is carried out with respect to each of the at least two sequestration pens.

Embodiment 116. The method of embodiment 115, further comprising comparing a level of secretion for sequestration pens of the at least two sequestration pens of the plurality.

Embodiment 117. The method of embodiment 115, further comprising comparing secretion scores of more than one sequestration pen of the plurality of sequestration pens.

Embodiment 118. The method of any one of embodiments 115 to 117, further comprising: selecting one or more of the at least two sequestration pens; and exporting one or more biological micro-objects from each of the selected sequestration pens.

Embodiment 119. The method of embodiment 118, wherein the one or more biological micro-objects from each of the selected sequestration pens are further exported out of the microfluidic device.

Embodiment 120. The method of embodiment 119, wherein the selected sequestration pens are exported individually.

Embodiment 121. The method of any one of embodiments 73 to 120, wherein the area of interest comprises an image area corresponding to an area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region.

Embodiment 122. The method of embodiment 121, wherein the area of interest consists essentially of the image area.

Embodiment 123. The method of any one of embodiments 73 to 122, wherein the method is automated.

Embodiment 124. A method of assessing a level of secretion of an analyte by a biological micro-object, or a population of biological micro-objects generated therefrom, the method comprising: introducing the biological micro-object into a sequestration pen of a microfluidic device, wherein the microfluidic device comprises an enclosure having a flow region, wherein the sequestration pen is fluidically connected to the flow region, and wherein the sequestration pen contains a first fluidic medium; allowing the biological micro-object, or the population of biological micro-objects generated therefrom, to secrete an analyte into the first fluidic medium within the sequestration pen; introducing a second fluidic medium into the flow region for a first period of time, wherein the second fluidic medium comprises a plurality of reporter complexes, and wherein each reporter complex comprises a first complex component configured to bind the secreted analyte and a second complex component bound to the first complex, wherein the second complex component comprises a detectable label, and wherein binding of the first complex component to the secreted analyte reduces or eliminates binding of the second complex component to the first complex component; allowing a portion of the plurality of reporter complexes to diffuse into the sequestration pen and bind to the analyte secreted therein, thereby producing a plurality of first complex component:secreted analyte (FCCSA) complexes; and detecting second complex components located within an area of interest within the microfluidic device, wherein the area of interest includes at least a portion of the sequestration pen.

Embodiment 125. The method of embodiment 124, wherein the detectable label comprises a visible, luminescent, phosphorescent, or fluorescent label.

Embodiment 126. The method of embodiment 124, wherein the detectable label of the second complex component is a fluorescent label, and wherein said detecting the second complex components comprises detecting fluorescence emission from the fluorescent label of the second complex components within the area of interest.

Embodiment 127. The method of any one of embodiments 124 to 126 further comprising: exposing, for a second period of time, a portion of the microfluidic device comprising the sequestration pen to electromagnetic radiation comprising a wavelength which is capable of exciting the fluorescent label of the second complex components.

Embodiment 128. The method of embodiment 127, wherein: detecting fluorescence emission within the area of interest is performed after the second period of time; detecting fluorescence emission is performed two or more times during a third period of time; and/or detecting fluorescence emission is performed substantially continuously during a third period of time.

Embodiment 129. The method of any one of embodiments 124 to 128, wherein the sequestration pen has an isolation region and a connection region fluidically connecting the isolation region to the flow region, and wherein the isolation region and the connection region are configured such that components of a fluidic medium in the isolation region are exchanged with components of a fluidic medium in the flow region substantially only by diffusion.

Embodiment 130. The method of any one of embodiments 124 to 129, wherein the biological micro-object is a biological cell, and wherein the method further comprises expanding the biological cell within the sequestration pen into a clonal population of biological cells.

Embodiment 131. The method of any one of embodiments 124 to 130 further comprising perfusing the flow region with a culturing medium, wherein the perfusing occurs after introducing the biological micro-object into the sequestration pen and before introducing the second fluidic medium into the flow region.

Embodiment 132. The method of embodiment 131, wherein the culturing medium comprises one or more of a soluble feeder cell component, a defined dissolved oxygen component, defined pH component, an exhausted growth medium component, and/or a soluble stimulatory component.

Embodiment 133. The method of any one of embodiments 124 to 132, wherein introducing the second fluidic medium into the flow region comprises flowing the second fluidic medium through the flow region for a first period of time.

Embodiment 134. The method of embodiment 133, wherein the first period of time is about 30 minutes to about 60 minutes.

Embodiment 135. The method of any one of embodiments 124 to 134, wherein the area of interest comprises at least a portion of the sequestration pen aligned along an axis of diffusion from within the sequestration pen to out into the flow region.

Embodiment 136. The method of any one of embodiments 124 to 135, wherein detecting the second complex components located within the area of interest comprises measuring an intensity of a detectable signal coming from the area of interest, wherein at least some of the detectable signal emanates from the detectable label of second complex components located within the area of interest.

Embodiment 137. The method of embodiment 136, wherein detecting the second complex components located within the area of interest further comprises determining a background-subtracted signal intensity by subtracting an intensity of a background signal from the measured intensity of the detectable signal.

Embodiment 138. The method of embodiment 136 or 137, further comprising measuring an intensity of a background signal within the area of interest, at a time prior to introducing the biological micro-object into the sequestration pen.

Embodiment 139. The method of any one of embodiments 136 to 138, wherein the measured intensity of the detectable signal or the background-subtracted signal intensity is normalized for a number of cells observed within the sequestration pen.

Embodiment 140. The method of any one of embodiments 124 to 139 further comprising quantifying the level of secretion of the analyte.

Embodiment 141. The method of any one of embodiments 124 to 139 further comprising providing a secretion score for the sequestration pen.

Embodiment 142. The method of embodiment 141, wherein the secretion score is determined according to the method of any one of embodiments 12 to 25 (i.e., from the Recitation of Selected Embodiments).

Embodiment 143. The method of any one of embodiments 124 to 142, wherein the secreted analyte has a molecular weight less than 5 kD.

Embodiment 144. The method of any one of embodiments 124 to 142, wherein the secreted analyte has a molecular weight less than 2 kD.

Embodiment 145. The method of any one of embodiments 124 to 142, wherein the secreted analyte has a molecular weight less than 1 kD.

Embodiment 146. The method of any one of embodiments 124 to 145, wherein the first complex component of the reporter complexes comprises at least one amino acid and/or at least one nucleic acid.

Embodiment 147. The method of any one of embodiments 124 to 145, wherein the first complex component of the reporter complexes comprises a peptide or protein.

Embodiment 148. The method of any one of embodiments 124 to 147, wherein the second complex component of the reporter complexes comprises a peptide having the sequence of any one of SEQ ID NOs: 1 to 10.

Embodiment 149. The method of any one of embodiments 124 to 147, wherein the second complex component of the reporter complexes comprises protein A, protein G, or an IgG-binding fragment of protein A or protein G.

Embodiment 150. The method of any one of embodiments 124 to 147, wherein the second complex component of the reporter molecule comprises an aptamer.

Embodiment 151. The method of any one of embodiments 124 to 147, wherein the second complex component of the reporter complexes comprises all or part of the secreted analyte (e.g., a part required for binding of the secreted analyte to the first complex component).

Embodiment 152. The method of any one of embodiments 124 to 151, wherein the secreted analyte competitively inhibits binding of the second complex component to the first complex component.

Embodiment 153. The method of any one of embodiments 124 to 151, wherein the secreted analyte non-competitively inhibits binding of the second complex component to the first complex component.

Embodiment 154. The method of embodiment 153, wherein the secreted analyte inhibits binding of the second complex component to the first complex component by an allosteric mechanism.

Embodiment 155. The method of any one of embodiments 124 to 154, wherein the analyte secreted by the biological micro-object comprises a peptide, a saccharide, an oligonucleotide, or an oligonucleoside.

Embodiment 156. The method of any one of embodiments 124 to 154, wherein the analyte secreted by the biological micro-object is a metabolite or an organic molecule other than a protein, saccharide, or nucleic acid.

Embodiment 157. The method of any one of embodiments 124 to 156, wherein the microfluidic device comprises a plurality of sequestration pens, wherein a biological micro-object is introduced into at least two sequestration pens of the plurality, and wherein the remainder of the method is carried out with respect to each of the at least two sequestration pens.

Embodiment 158. The method of embodiment 157, further comprising comparing a level of secretion for sequestration pens of the at least two sequestration pens of the plurality of sequestration pens.

Embodiment 159. The method of embodiment 157, further comprising comparing secretion scores of more than one sequestration pen of the plurality of sequestration pens.

Embodiment 160. The method of any one of embodiments 157 to 159, further comprising: selecting one or more of the at least two sequestration pens; and exporting one or more biological micro-objects from each of the selected sequestration pens.

Embodiment 161. The method of embodiment 160, wherein the one or more biological micro-objects from each of the selected sequestration pens are further exported out of the microfluidic device.

Embodiment 162. The method of embodiment 161, wherein the selected sequestration pens are exported individually.

Embodiment 163. The method of any one of embodiments 124 to 162, wherein the area of interest comprises an image area corresponding to an area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region.

Embodiment 164. The method of embodiment 163, wherein the area of interest consists essentially of the image area.

Embodiment 165. The method of any one of embodiments 124 to 164, wherein the method is automated.

Embodiment 166. A method of clonal line development, the method comprising: performing the method of any one of embodiments 66, 117, and 159; selecting a set of sequestration pens from the plurality of sequestration pens, wherein each sequestration pen of the set has a score indicating that the biological micro-object, or clonal population, contained therein is a top analyte producer; exporting from the microfluidic device one or more biological micro-objects contained within each sequestration pen of the set of selected sequestration pens; expanding the exported one or more biological micro-objects from each sequestration pen of the set of selected sequestration pens in corresponding reaction vessels; and determining a level of analyte secreted in each corresponding reaction vessel, thereby determining a level of secretion for each biological micro-object or clonal population.

Embodiment 167. The method of embodiment 166, wherein the area of interest comprises an image area corresponding to an area within the sequestration pen that is most sensitive for measuring analyte concentration fluctuations, is least sensitive to the position of biological micro-objects in the sequestration pen when analyte fluctuations are measured, and extends along an axis of diffusion between the sequestration pen and the flow region.

Embodiment 168. The method of embodiment 167, wherein the area of interest consists essentially of the image area.

Embodiment 169. The method of any one of embodiments 166 to 168, wherein the method is automated.

Embodiment 170. A kit for evaluation of levels of an analyte secreted by a biological micro-object, or a population of biological micro-objects generated therefrom, the kit comprising: a microfluidic device comprising an enclosure having a flow region and a plurality of sequestration pens, wherein each sequestration pen is fluidically connected to the flow region, and wherein the flow region and the sequestration pens are configured to contain a fluidic medium; and a reporter complex comprising a first complex component configured to be bind to the secreted analyte and a second complex component configured to bind to the first complex component and comprising a detectable label, wherein binding of the secreted analyte to the first complex component inhibits or prevents binding of the second complex component to the first complex component.

Embodiment 171. The kit of embodiment 170, wherein the first complex component of the reporter complex comprises at least one amino acid and/or at least one nucleic acid.

Embodiment 172. The kit of embodiment 170, wherein the first complex component of the reporter complex comprises a peptide or protein.

Embodiment 173. The kit of any one of embodiments 170 to 172, wherein the second complex component of the reporter complexes comprises a peptide having the sequence of any one of SEQ ID NOs: 1 to 10.

Embodiment 174. The kit of any one of embodiments 170 to 172, wherein the second complex component of the reporter complexes comprises protein A, protein G, or an IgG-binding fragment of protein A or protein G.

Embodiment 175. The kit of any one of embodiments 170 to 172, wherein the second complex component of the reporter molecule comprises an aptamer.

Embodiment 176. The kit of any one of embodiments 170 to 172, wherein the second complex component of the reporter complexes comprises all or part of the secreted analyte (e.g., a part required for binding of the secreted analyte to the first complex component).

Embodiment 177. The kit of any one of embodiment 170 to 176, wherein the secreted analyte competitively inhibits binding of the second complex component to the first complex component.

Embodiment 178. The kit of any one of embodiments 170 to 176, wherein the secreted analyte non-competitively inhibits binding of the second complex component to the first complex component.

Embodiment 179. The kit of embodiment 178, wherein the secreted analyte inhibits binding of the second complex component to the first complex component by an allosteric mechanism.

Embodiment 180. A non-transitory computer-readable medium in which a program is stored for causing a computer to direct a system to perform a method for determining a quantity of analyte produced by a biological micro-object, wherein the method is the method of any one of embodiments 45 to 47.

Embodiment 181. The non-transitory computer-readable medium of embodiment 180, wherein the system is the system of any one of embodiments 1 to 11.

Embodiment 182. A non-transitory computer-readable medium in which a program is stored for causing a computer to direct a system to perform at least part of a method for clonal line development, wherein the method is the method of any one of embodiments 166 to 169, and wherein the system performs at least the steps up until and including exporting from the microfluidic device the one or more biological micro-objects contained within each sequestration pen of the set of selected sequestration pens.

Embodiment 183. The non-transitory computer-readable medium of embodiment 182, wherein the system is the system of any of embodiments 1 to 11.

What is claimed:

1. A method of assessing a level of secretion of an analyte by a biological micro-object, or a population of biological micro-objects generated therefrom, the method comprising:
   introducing the biological micro-object into a sequestration pen of a microfluidic device, wherein the microfluidic device comprises an enclosure having a flow region, wherein the sequestration pen is fluidically connected to the flow region, and wherein the sequestration pen contains a first fluidic medium;
   allowing the biological micro-object, or the population of biological micro-objects generated therefrom, to secrete an analyte comprising an exogenous tag into the first fluidic medium within the sequestration pen;
   introducing a second fluidic medium into the flow region, wherein the second fluidic medium comprises a plurality of reporter molecules, and wherein each reporter molecule comprises:
   a binding component configured to bind the exogenous tag of the secreted analyte; and
   a detectable label;
   allowing a portion of the plurality of reporter molecules to diffuse into the sequestration pen and bind to the analyte secreted therein, thereby producing a plurality of reporter molecule: secreted analyte (RMSA) complexes; and detecting reporter molecules located within an area of interest within the microfluidic device, wherein the area of interest includes at least a portion of the sequestration pen.

2. The method of claim 1, wherein the sequestration pen has an isolation region and a connection region fluidically connecting the isolation region to the flow region, and wherein the isolation region and the connection region are configured such that components of a fluidic medium in the isolation region are exchanged with components of a fluidic medium in the flow region substantially only by diffusion.

3. The method of claim 1, wherein the biological micro-object is a biological cell, and wherein the method further comprises expanding the biological cell within the sequestration pen into a clonal population of biological cells.

4. The method of claim 1, wherein the detectable label comprises a visible, luminescent, phosphorescent, or fluorescent label.

5. The method of claim 4, wherein the detectable label of the reporter molecules is a fluorescent label, and wherein said detecting the reporter molecules comprises detecting fluorescence emission from the fluorescent label of the reporter molecules within the area of interest.

6. The method of claim 5 further comprising:
introducing the second fluidic medium into the flow region by flowing the second fluidic medium through the flow region for a first period of time; and
exposing, for a second period of time, a portion of the microfluidic device comprising the sequestration pen to electromagnetic radiation comprising a wavelength which is capable of exciting the fluorescent label of the reporter molecules.

7. The method of claim 6, wherein:
detecting fluorescence emission within the area of interest is performed after the second period of time;
detecting fluorescence emission within the area of interest is performed two or more times during a third period of time; and/or
detecting fluorescence emission within the area of interest is performed substantially continuously during a third period of time.

8. The method of claim 7 further comprising:
exposing, for a fourth period of time, a portion of the microfluidic device comprising at least a portion of the sequestration pen to electromagnetic radiation but not the flow region, wherein the fourth period of time is sufficient to photobleach the fluorescent label of any reporter molecules present in the portion of the sequestration pen; and
detecting fluorescence emission within the photobleached portion of the sequestration pen.

9. The method of claim 8, wherein:
detecting fluorescence emission within the photobleached portion of the sequestration pen is performed after the fourth period of time;
detecting fluorescence emission within the photobleached portion of the sequestration detecting fluorescence emission within the photobleached portion of the sequestration pen is performed two or more times during a fifth period of time; and/or
detecting fluorescence emission within the photobleached portion of the sequestration detecting fluorescence emission within the photobleached portion of the sequestration pen is performed substantially continuously during a fifth period of time.

10. The method of claim 8, wherein said steps of exposing for a fourth period of time and detecting fluorescence emission within the photobleached portion of the sequestration pen are repeated one or more times.

11. The method of claim 1, further comprising:
introducing a third fluidic medium into the flow region, wherein the third fluidic medium does not comprise any of the reporter molecules; and
allowing at least a portion of unbound reporter molecules to diffuse out of the sequestration pen,
wherein detecting the reporter molecules located within the area of interest occurs at a time selected such that an amount of unbound reporter molecules that have diffused out of the sequestration pen is at least 2× greater than an amount of RMSA complexes that have diffused out of the sequestration pen.

12. The method of claim 1, further comprising quantifying the level of secretion of the analyte and/or providing a secretion score for the sequestration pen.

13. The method of claim 1, wherein the exogenous tag of the secreted analyte comprises a peptide sequence.

14. The method of claim 13, wherein the peptide sequence comprises a FLAG epitope, a polyhistidine sequence, a hemagglutinin (HA) epitope, or a Myc epitope.

15. The method of claim 13, wherein the peptide sequence comprises the amino acid sequence (from N-terminal to C-terminal) DYKDDDDK (SEQ ID NO: 11).

16. The method of claim 13, wherein the peptide sequence comprises the amino acid sequence (from N-terminal to C-terminal) HHHHHH (SEQ ID NO: 12).

17. The method of claim 13, wherein the binding component of the reporter molecule is an antibody.

18. The method of claim 16, wherein the binding component of the reporter molecule comprises a chelating agent.

19. The method of claim 1, wherein the analyte secreted by the biological micro-object comprises a protein.

20. The method of claim 19, wherein the analyte secreted by the biological micro-object is an antibody.

21. The method of claim 1, wherein the microfluidic device comprises a plurality of sequestration pens, wherein a biological micro-object is introduced into at least two sequestration pens of the plurality, and wherein the remainder of the method is carried out with respect to each of the at least two sequestration pens.

22. The method of claim 21, further comprising comparing a level of secretion for sequestration pens of the at least two sequestration pens of the plurality.

23. The method of claim 21, further comprising:
selecting one or more of the at least two sequestration pens; and
exporting one or more biological micro-objects from each of the selected sequestration pens out of the microfluidic device.

* * * * *